(12) United States Patent
Garsha et al.

(10) Patent No.: US 10,598,548 B2
(45) Date of Patent: Mar. 24, 2020

(54) SYSTEMS AND METHODS FOR CALIBRATING, CONFIGURING AND VALIDATING AN IMAGING DEVICE OR SYSTEM FOR MULTIPLEX TISSUE ASSAYS

(71) Applicant: Ventana Medical Systems, Inc., Tucson, AZ (US)

(72) Inventors: Karl Garsha, Sahuarita, AZ (US); Michael Otter, Tucson, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 0 days.

(21) Appl. No.: 16/004,244

(22) Filed: Jun. 8, 2018

(65) Prior Publication Data

US 2018/0292260 A1 Oct. 11, 2018

Related U.S. Application Data

(62) Division of application No. 14/764,918, filed as application No. PCT/EP2014/051920 on Jan. 31, 2014, now Pat. No. 10,012,537.

(Continued)

(51) Int. Cl.
*G06K 9/00* (2006.01)
*G01J 3/02* (2006.01)
(Continued)

(52) U.S. Cl.
CPC ............ *G01J 3/0297* (2013.01); *G01J 3/10* (2013.01); *G01J 3/28* (2013.01); *G01J 3/2823* (2013.01);
(Continued)

(58) Field of Classification Search
CPC .... G01J 2003/2826; G01J 3/0297; G01J 3/10; G01J 3/28; G01J 3/2823; G01J 3/44;
(Continued)

(56) References Cited

U.S. PATENT DOCUMENTS 7,262,842 B2  8/2007  Ermantraut et al.
7,403,336 B2  7/2008  Golberg et al.
(Continued)

FOREIGN PATENT DOCUMENTS

JP   2003298913 A   10/2003
JP   2011022044 A   2/2011
(Continued)

OTHER PUBLICATIONS

Gammon, Seth T., et al. "Spectral unmixing of multicolored bioluminescence emitted from heterogeneous biological sources." Analytical chemistry 78.5 (2006): 1520-1527. (Year: 2006).*
(Continued)

*Primary Examiner* — Nirav G Patel
(74) *Attorney, Agent, or Firm* — Kilpatrick Townsend & Stockton LLP

(57) ABSTRACT

A system and method for characterization and/or calibration of performance of a multispectral imaging (MSI) system equipping the MSI system for use with a multitude of different fluorescent specimens while being independent on optical characteristics of a specified specimen and providing an integrated system level test for the MSI system. A system and method are adapted to additionally evaluate and express operational parameters performance of the MSI system in terms of standardized units and/or to determine the acceptable detection range of the MSI system.

20 Claims, 44 Drawing Sheets

Related U.S. Application Data

(60) Provisional application No. 61/759,262, filed on Jan. 31, 2013.

(51) Int. Cl.
    *G06T 7/80*     (2017.01)
    *G01J 3/28*     (2006.01)
    *G01J 3/44*     (2006.01)
    *G01N 21/27*     (2006.01)
    *G02B 21/36*     (2006.01)
    *G01J 3/10*     (2006.01)

(52) U.S. Cl.
    CPC .............. *G01J 3/44* (2013.01); *G01J 3/4406* (2013.01); *G01N 21/274* (2013.01); *G02B 21/365* (2013.01); *G06K 9/0014* (2013.01); *G06T 7/80* (2017.01); *G01J 2003/2826* (2013.01)

(58) Field of Classification Search
    CPC ... G01J 3/4406; G01N 21/274; G02B 21/365; G06K 9/0014; G06T 7/80
    See application file for complete search history.

(56) References Cited

U.S. PATENT DOCUMENTS

| | | | |
|---|---|---|---|
| 8,055,035 | B2 | 11/2011 | Okugawa et al. |
| 8,081,311 | B2 | 12/2011 | Themelis |
| 8,699,023 | B2 | 4/2014 | Ohtsuka et al. |
| 2010/0056928 | A1 | 3/2010 | Zuzak et al. |
| 2012/0081532 | A1 | 4/2012 | Kumai |
| 2014/0193050 | A1 | 7/2014 | Miller |

FOREIGN PATENT DOCUMENTS

| | | | |
|---|---|---|---|
| JP | 2011069735 | A | 4/2011 |
| JP | 2011089895 | A | 5/2011 |
| JP | 201263321 | A | 3/2012 |
| WO | 200250518 | A2 | 6/2002 |

OTHER PUBLICATIONS

Akinyemi et al, Chromatism and Confocality in Confocal Microscopes, Scanning, 1992, pp. 136-143, vol. 14.
Browne et al, Confocal Surface Profiling Utilizing Chromatic Aberration, Scanning, 1992, pp. 145-153, vol. 14.
Dickinson et al, Multi-Spectral Imaging and Linear Unmixing Add a Whole New Dimension to Laser Scanning Fluorescence Microscopy, BioTechniques, 2001, pp. 1272-1278, vol. 31, No. 6.
Gammon et al, Spectral Unmixing of Multicolored Bioluminescence Emitted from Heterogeneous Biological Sources, Anal. Chem., 2006, pp. 1520-1527, vol. 78.
Garini et al, Signal to Noise Analysis of Multiple Color Fluorescence Imaging Microscopy, Cytometry, 1999, pp. 214-226, vol. 35.
Garini et al, Spectral Imaging: Principles and Applications, Cytometry Part A, 2006, pp. 735-747, vol. 69A.
Garsha, Karl, Quantitative Fluorescence Microscopy: Considerations and Controls, Springer Series on Fluorescence, 2008, pp. 55-88, vol. 6.
Hibbs et al, 36: Practical Confocal Microscopy, Handbook of Biological Confocal Microscopy, 2006, pp. 650-671, Third Edition.
ISR and WO for PCT/EP2014/051920 dated Aug. 27, 2014, 8 pages.
Janesick, J.R., Scientific Charge-Coupled Devices, Scientific Charge-Coupled Devices, 2001, pp. 95-166, SPIE Press.
Lansford et al, Resolution of multiple green fluorescent protein color variants and dyes using two-photon microscopy and imaging spectroscopy, Journal of Biomedical Optics, Jul. 2001, pp. 311-318, vol. 6, No. 3.
Lerner et al, Calibration and Validation of Confocal Spectral Imaging Systems, Cytometry Part A, 2004, pp. 8-34, vol. 62A.
Model et al, A Standard for Calibration and Shading Correction of a Fluorescence Microscope, Cytometry, 2001, pp. 309-316, vol. 44.
Mortara et al, Evaluations of charge-coupled device (CCD) performance for astronomical use, SPIE: Solid State Imagers for Astronomy, 1981, pp. 28-33, vol. 290.
Neher et al, Optimizing imaging parameters for the separation of multiple labels in a fluorescence image, Journal of Microscopy, Jan. 2004, pp. 46-62, vol. 213, Pt. 1.
Pawley, J.B., Sources of Noise in Three-Dimensional Microscopical Data Sets, Three-Dimensional Confocal Microscopy: Volume Investigation of Biological Specimens, 1994, pp. 47-93, Chapter 3.
Pawley, Jim, The 39 Steps: A Cautionary Tale of Quantitative 3-D Fluorescence Microscopy, BioTechniques, 2000, pp. 884-886, vol. 28, No. 5.
Resch-Genger et al, Standardization of Fluorescence Measurements: Criteria for the Choice of Suitable Standards and Approaches to Fit-for-Purpose Calibration Tools, Annals of the New York Academy of Sciences, 2008, pp. 35-43, vol. 1130.
Resch-Genger et al, Traceability in Fluorometry, Part II: Spectral Fluorescence Standards, Journal of Fluorescence, May 2005, pp. 315-336, vol. 15, No. 3.
Scalettar et al, Dispersion, aberration and deconvolution in multi-wavelength fluorescence images, Journal of Microscopy, Apr. 1996, pp. 50-60, vol. 182, Pt. 1.
Sourchier et al, Data reproducibility in fluorescence image analysis, Methods in Cell Science, 2004, pp. 195-200, vol. 25.
Spiclin et al, Geometric calibration of a hyperspectral imaging system, Applied Optics, 2010, pp. 1-6, vol. 49.
Stark et al, Fluorescent resolution target for super-resolution microscopy, Journal of Microscopy, Dec. 2003, pp. 307-310, vol. 212, Pt. 3.
Tran, Phong, CCD Cameras for Fluorescence Imaging of Living Cells, Live Cell Imaging: A Laboratory Manual, 2005, pp. 87-100, Chapter 6, Cold Spring Harbor Laboratory Press.
Van Den Doel et al, Quantitative evaluation of light microscopes based on image processing techniques, Bioimaging, 1998, pp. 138-149, vol. 6.
Written Opinion of the ISA for Application No. PCT/EP2014/051920, 22 pages.
Young, Matt, 7.3: Impulse Response and Transfer Function, Optics and Lasers Including Fibers and Optical Waveguides, 2000, pp. 181-192.
Zucker et al, Evaluation of Confocal Microscopy System Performance, Cytometry, 2001, pp. 273-294, vol. 44.
Zucker et al, Practical Confocal Microscopy and the Evaluation of System Performance, Methods, 1999, pp. 447-458, vol. 18.
Zucker et al, Statistical Evaluation of Confocal Microscopy Images, Cytometry, 2001, pp. 295-308, vol. 44.

\* cited by examiner

600

- 602 — Ensure even illumination is transmitted to the camera and acquire and correct 2 images in the manner outlined in FIG.5D
- 603 — Calculate a difference image by subtracting the first image from the second
- 604 — Determine the standard deviation and/or variance of pixel values in the resulting difference image at every wavelength
- 605 — Calculate the mode pixel value of the difference image
- 606 — Determine the Standarized Unit from: $\frac{variance}{mode} = $ e–per grey–scale level

- 802 — Determine the grey-scale to standard unit conversion per method 580 (FIG.5E)
- 803 — Calculate the camera noise level at every wavelegth per method 600 (FIG.5F)
- 804 — Determine the maximum grey-scale value for the sensor and convert to standard units
- 805 — Express the useful dynamic range (in standard units) as ratio $$\frac{noise+conversion}{noise+conversion} : \frac{maximum\ value\ possible}{noise+conversion}$$

FIG.5G

| Specounter Unmixed Channels | | | | Actual |
|---|---|---|---|---|
| Standard | Average Intensity | 3td. Dev. | % Total | |
| Peak 1 | 16107 | 489 | 12.4% | 6% |
| Peak 2 | 44460 | 2035 | 34.2% | 26% |
| Peak 3 | 818 | 150 | 0.6% | 1% |
| Peak 4 | 911 | 137 | 0.7% | 1% |
| Peak 5 | 5106.5 | 1293 | 3.0% | 1% |
| Peak 6 | 62673 | 1141 | 48.2% | 58% |
| | 130075.5 | | | |

FIG.20C

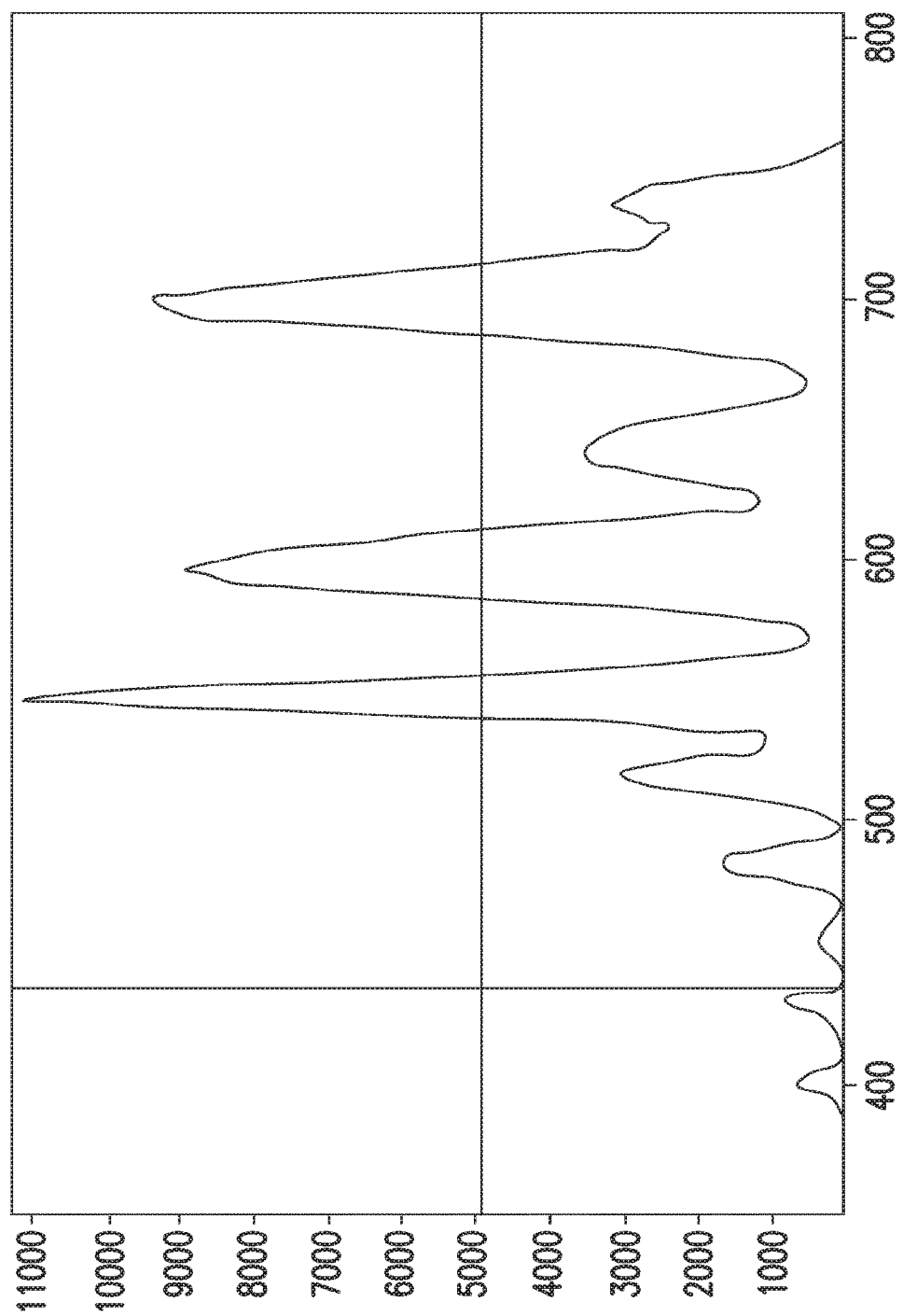

| Spectral Band | Mean Value | StdDev | Mode | CV | SpectraView Unmix | Measured Value | Specounter Unmix |
|---|---|---|---|---|---|---|---|
| Ref_400 | 2764.199 | 439.961 | 2805.901 | 15.92% | 1.56% | 0.60% | 2.55% |
| Ref_430 | 3016.567 | 436.524 | 3015.429 | 14.47% | 1.68% | 0.80% | 2.22% |
| Trans_455 | 1733.771 | 519.315 | 1709.698 | 29.95% | 0.95% | 0.50% | 1.21% |
| Ref_483 | 6797.309 | 585.718 | 6911.142 | 8.62% | 3.85% | 2.40% | 3.21% |
| Trans_517 | 13824.951 | 1234.099 | 12719.092 | 8.93% | 7.09% | 5.60% | 6.42% |
| Ref_54 | 40473.368 | 1901.704 | 42446.034 | 4.70% | 23.66% | 18.40% | 19.31% |
| Trans_598 | 49746.924 | 2592.364 | 46958.254 | 5.21% | 26.66% | 26.30% | 25.57% |
| Ref_641 | 15856.347 | 1393.133 | 14766.372 | 8.79% | 8.23% | 10.10% | 9.32% |
| Trans_698 | 50009.173 | 2841.358 | 48081.802 | 5.68% | 26.80% | 36.20% | 31.25% |
| Total | | Total Signal 179413.724 | | 102.26% | 99.99% | 100.90% | 101.06% |

FIG. 21B-2

SYSTEMS AND METHODS FOR CALIBRATING, CONFIGURING AND VALIDATING AN IMAGING DEVICE OR SYSTEM FOR MULTIPLEX TISSUE ASSAYS

RELATED APPLICATIONS

This patent application is a divisional application of U.S. patent application Ser. No. 14/764,918, filed Jul. 30, 2015, which is the U.S. National Stage filing of International Patent Application No. PCT/EP2014/051920, filed Jan. 31, 2014, which claims priority to and the benefit of U.S. Provisional Application No. 61/759,262, filed Jan. 31, 2013. Each of the above patent applications is incorporated herein by reference as if set forth in its entirety.

TECHNICAL FIELD

The present invention relates to systems and methods for calibration of imaging devices. More specifically, the present invention involves calibrating a multispectral imaging system and/or components thereof. The present invention also involves configuring operational parameters of the imaging system

SUMMARY OF THE INVENTION

Embodiments of the invention provide for a method for assessing the quality of a multispectral imaging (MSI) system that includes a processor programmed to govern an operation of said imaging. Embodiments of the invention also include computer-implemented methods for calibrating, characterizing, and configuring an MSI. Such method comprises collecting data, during a first spectral scan of the MSI system across at least at least a portion of a spectral range of the MSI system, and at an output of a detector of the MSI system and with no exposure of said detector to ambient light, such as to form a first set of spectral data representing output of said detector at chosen wavelengths. The method additionally includes determining presence of stray light in the MSI system by comparing subsets of said acquired spectral data; and optically adjusting the imaging system when the presence of stray light is positively determined.

During a second spectral scan of the MSI system across said at least a portion of a spectral range of said MSI system, receiving, at the detector, light from a first light source that has standardized output power and a spectrum of a calibrated light standard to form a second set of spectral data representing output of the detector at the chosen wavelengths. Moreover, the method further includes a step of receiving, at the detector and during a third spectral scan of the MSI system across said at least a portion of a spectral range of the MSI system, light from the first light source to form a second set of spectral data representing output of said detector at the chosen wavelengths.

Alternatively or in addition, the method involves determining operational characteristics of the MSI system in terms of standardized units. Such determination may involve one or more of determining a slope of a curve representing a mode intensity of an image acquired with the MSI system on an intensity variance of said image at one or more single wavelengths or narrow bandwidths; calculating noise figure associated with data acquisition by the MSI system; and determining a wavelength-dependent response of the MSI with the use of incident light having a spectrum containing multiple spectral bandwidths of substantially equal widths centered at wavelengths corresponding to emission wavelengths of a known spectral marker. The known spectral marker optionally includes at least one of a chosen analyte and a quantum dot.

Embodiments of the invention further provide a system for calibrating and determining the performance of a multispectral imaging (MSI) system. In one implementation, such system includes (i) at least one light source configured to operate with substantially fixed operational characteristics and including an optical filter having a transmission spectrum that corresponds to a spectrum of a calibrated light standard and (ii) a geometrical standard characterized by distribution of reflectivity that is spatially-periodic. The operational characteristics of the light source include at least temperature and electrical operational characteristics, and the light source is adapted to produce light output with spectrum including multiple spectral bands centered at respectively corresponding central wavelengths. The MSI system additionally includes an optical system configured (a) to receive said light output from the used or active light source, (b) to deliver light from said received light output to said geometrical standard, and (c) to redirect light that has interacted with said geometrical standard to said MSI system. The optical system is optionally configured to redirect light that has reflected from said geometrical standard. Light power delivered from the light source to the geometrical standard can, optionally, be varied independently from variation of the transmission spectrum. Furthermore, in one embodiment the light source is configured to deliver, to the geometrical standard, a first beam of light that transmits through said geometrical standard and a second beam of light that reflects from the geometrical standard such that spectral bands associated with the first light and spectral bands associated with the second light substantially overlap.

In one embodiment, the system for calibration is configured such as to permit adjustment of light power, in a given spectral band selected from multiple spectral bands, that is directed to the MSI system without substantially affecting spectral content of the other spectral bands. The system for calibration may be further configured such as to permit measurement of light power, in a first spectral band selected from the multiple spectral bands, substantially independently from measuring of light power in a second spectral band selected from the multiple spectral bands.

Embodiments of the invention additionally provide a system for calibration of performance of a multispectral imaging (MSI) system that has an object plane and a field of view (FOV). Such system for calibration includes at least one light source adapted to produce light output having a spectrum with multiple bands such that amount of light in one or more of the multiple bands is adjustable substantially without affecting a remaining spectral band, while each of the multiple bands is centered at a corresponding central wavelength. The system for calibration further includes an optical system defining multiple optical paths for illumination of the object plane and configured to deliver light from the object plane, to the MSI system. Such system for calibration is adapted to permit determination of light power in a first spectral band, selected from the multiple spectral bands, substantially independently from determination of light power in a second spectral band selected from the multiple spectral bands. The optical system of the system for calibration is configured, in one embodiment, to gather light that has interacted with the geometrical standard in both reflection and transmission.

In a specific embodiment, the system for calibration additionally contains a reference sample configured, when placed at the object plane, to spatially separate light in a spectral-band dependent fashion such as to permit spatial calibration of optical performance of the MSI system across the FOV. The system for calibration may further include a processor, programmed to form a set of data representing amount of light carried in each of the multiple spectral bands, and tangible non-transitory computer-readable medium operably connected to the processor and adapted to store such set of data.

Embodiments of the invention also provide a method for determining accuracy and precision of a computational algorithm for spectral unmixing of a multispectral (MS) image. The method includes (i) acquiring, with a detector, image of a reference sample evenly illuminated or substantially evenly illuminated with light from a light source having spectral output with multiple spectral bands; (ii) correcting the acquired image for the baseline intensity offset of pixel values or 'bias' to form a bias-corrected MS image; and (iii) determining an integrated intensity value based on an averaged intensity profile corresponding to said bias-corrected acquired image.

In one implementation, the determining of an integrated intensity value includes averaging a spectral profile of intensity of the bias-corrected MS image over chosen pixels of the detector such as to form an averaged intensity profile. Alternatively, or in addition, the step of acquiring may include acquiring an image of a reference sample illuminated with light from a light source, which light source contains an optical filter having a transmission spectrum corresponding to a spectrum of a calibrated light standard. Alternatively or in addition, the step of inquiring may include (a) receiving, with the detector, a first beam of light that has transmitted through the reference sample and a second beam of light that has reflected off of the reference sample, where each of said first and second light has a corresponding multiband spectrum; and (b) determining a contribution, to light received with the detector, of light in a first spectral band of the first beam of light, where the such determination is carried out independently from the determination of a corresponding contribution of light in the second spectral band of the second beam of light.

In a specific implementation, the method may include a step of varying relative contributions of light from different spectral bands to image acquired with the detector, where such process of varying is performed substantially without changing spectral content of light received with the detector. In addition, the method may include defining relative contributions of light from different spectral bands of an output of the calibrated light source; and individually normalizing averaged intensity profiles corresponding to the multiple spectral bands to define normalized individual reference spectra respectively corresponding to the multiple spectral bands. The method optionally also includes a step of determination of differences between results of the computational spectral unmixing algorithm and the defined relative contributions of light.

Embodiments of the invention alternatively provide a method for determining a wavelength dependence of operation of a multispectral imaging (MSI) system, which method includes the steps of (i) acquiring, with a detector of the MSI system, first image data representing an image of an object illuminated with first wavelength or narrow bandwidth of light from a light source that has output spectrum with multiple spectral bands; (ii) acquiring, with the detector, second image data representing an image of the object illuminated with second wavelength or narrow bandwidth from the light source, such that the first and second light correspond to different first and second spectral bands of the multiple spectral bands and have respectively corresponding first and second power; and (iii) determining normalized quantum efficiency at different wavelengths for the detector. The method may further include a step of (iv) collecting third image data, representing an image of the object illuminated with third wavelength or narrow bandwidth from the light source, with the use of the determined normalized quantum efficiency, such that the third light corresponds to a third spectral band of said multiple spectral bands, and the third spectral band is different from the first spectral band.

Embodiments of the invention also include a method of calibrating a spectral camera of a multispectral imaging (MSI) system comprising: illuminating a substrate with a light source of a first predetermined intensity level and/or power a first time; collecting a first set of spectral image data of the substrate via a sensor of the MSI system; illuminating the substrate with the light source at the first predetermined intensity level a second time; collecting a second set of spectral image data of the substrate via a sensor of the MSI system at the first predetermined intensity level; and subtracting or adjusting the first set of spectral image data from the second set of spectral image data, and generating first difference image data; collecting a third set of spectral imaging data at a second predetermined intensity level and a fourth set of spectral imaging data at the second predetermined intensity level; subtracting the third set of spectral image data from the fourth set of spectral image data, and generating second difference image data; calculating at least one of the mode and the mean of the first difference image data; determining at least one of variance and standard deviation of pixel values of the first difference image data, based on the at least one of the mode and the mean of the first difference image data at every wavelength of the first difference image data, generating first resulting image data; calculating at least one of the mode and the mean of the second difference image data; determining at least one of variance and standard deviation of pixel values of the second difference image data, based on the at least one of the mode and the mean of the second difference image data at every wavelength of the second difference image data, generating second resulting image data; generating a conversion value, for each wavelength, based on the first resulting image data, the second resulting image data, the at least one of the mode and the mean of the first difference image data, and the at least one of the mode and the mean of the second difference image data, wherein the conversion value is representative of an approximate number of electrons recorded at each pixel per grey level. The conversion value is determined by generating a slope or approximate slope between (1) a set of data corresponding to the first resulting image data as a function of the at least one of a mode and the mean of the first difference image data and (2) a set of data corresponding to the second resulting image data as a function of the at least one of a mode and the mean of the second difference image data. The conversion value for each wavelength is compared to the other conversion values for each wavelength, and wherein differences between the values are utilized to calibrate the MSI system.

Embodiments of the invention also include a method for generating a corrected image for a multispectral imaging system, comprising: A method for generating a corrected image for a multispectral imaging system, comprising: acquiring a first spectral image via a sensor when the exposure time of a first spectrum source of the system is zero, and generating first spectral image data at a plurality of wavelengths; determining a modal pixel intensity value for each wavelength of the plurality of wavelengths of the first spectral image, wherein the modal pixel intensity value at each wavelength of the plurality of wavelengths of the first spectral image corresponds to a pixel intensity offset value at each wavelength of the plurality of wavelengths of the first spectral image;
acquiring a second spectral image by the first spectrum source, and wherein the exposure time of the first spectrum source is greater than zero, and generating second spectral image data of a plurality of wavelengths; and subtracting the pixel intensity offset value at each wavelength of the plurality of wavelengths of the first spectral image from a value of each of a plurality of pixels at each corresponding wavelength of the second spectral image data.

In exemplary embodiments of the present invention, mean values may be replaced by modal values, or other suitable values.

Embodiments of the present invention may also involve a method of calibrating a spectral camera of a multispectral imaging (MSI) system, said method comprising: illuminating a substrate with a light source of a first predetermined intensity level a first time; collecting a first set of spectral image data of the substrate via at least one of a sensor of the MSI system and the spectral camera; illuminating the substrate with the light source at the first predetermined intensity level a second time; collecting a second set of spectral image data of the substrate via the at least of a sensor of the MSI system and the spectral camera; and subtracting the first set of spectral image data from the second set of spectral image data, and generating first difference image data; collecting a third set of spectral imaging data via the at least of the sensor of the MSI system and the spectral camera at a second predetermined intensity level; collecting a fourth set of spectral imaging data at the second predetermined intensity level; subtracting the third set of spectral image data from the fourth set of spectral image data, and generating second difference image data; calculating at least one of the mode and the mean of the first difference image data; determining at least one of variance and standard deviation of pixel values of the first difference image data at every wavelength of the first difference image data, based on the at least one of the mode and the mean of the first difference image data, and generating first resulting image data; calculating at least one of the mode and the mean of the second difference image data; determining at least one of variance and standard deviation of pixel values of the second difference image data at every wavelength of the second difference image data, based on the at least one of the mode and the mean of the second difference image data, and generating second resulting image data; generating a conversion value for each wavelength of the second difference image data based on the first resulting image data, the second resulting image data, the at least one of the mode and the mean of the first difference image data, and the at least one of the mode and the mean of the second difference image data, wherein the conversion value is representative of an approximate number of electrons recorded at each pixel per grey level in at least one of the first, second, third, and fourth spectral image data.

In exemplary embodiments of the present invention, the light source, may be replaced by another spectrum source, and the light or spectrum source may also remain activated or on, such that, for example, when two sets of spectral image data are captured at the same predetermined intensity level or power, the substrate is illuminated once, and thus, there is no need to illuminate the substrate a second time.

Embodiments of the invention also include a computer program product which, when loaded on a non-transitory tangible computer-readable, and optionally programmable, medium, is configured to program a computer processor to effectuate steps of the disclosed invention, including the above-mentioned methods and operation of the above-mentioned systems.

BRIEF DESCRIPTION OF THE DRAWINGS

The invention will be more fully understood by referring to the following Detailed Description in conjunction with the Drawings, which are generally drawn not to scale and of which:

FIG. 5E is a flow chart illustrating method 600 for determining a standardized conversion (mean/variance calculation) of spectral images from arbitrary grey-scale units to standardized intensity units (e−).

FIG. 5G is a flow chart illustrating method 800 for evaluating the dynamic range of a spectral imaging sensor.

FIGS. 20A, 20B, and 20C provide an illustration to a system-level test of a measurement system that is assumed to have been pre-calibrated.

FIGS. 21A-1 through 21A-3 and 21B-1 through 21B-3 provide plots and related data illustrating a spectral unmixing of 9 spectral features

DETAILED DESCRIPTION

Embodiments of the present invention may be employed with an imaging system such as a multispectral imaging (MSI) system (for example, an imaging spectrometer, a fluorescent microscopy system, a pathology imaging system). MSI systems, generally, facilitate the analysis of pathology specimens, including tissue samples. MSI systems typically include, for example, computerized microscope-based imaging systems equipped with spectrometers, spectroscopes, spectrographs, spectral cameras, charge couple devices (CCDs), light sensors, optical detectors, and/or imaging spectrometers etc.). MSI systems and/or devices are able to capture the spectral distribution of an image at a pixel level, and provide the ability to acquire multispectral data representing a two-dimensional (2D) spatial field of view, with data sets representing light intensity as a function of wavelength at each pixel of an image recorded by an optical detector.

Figure 1A:
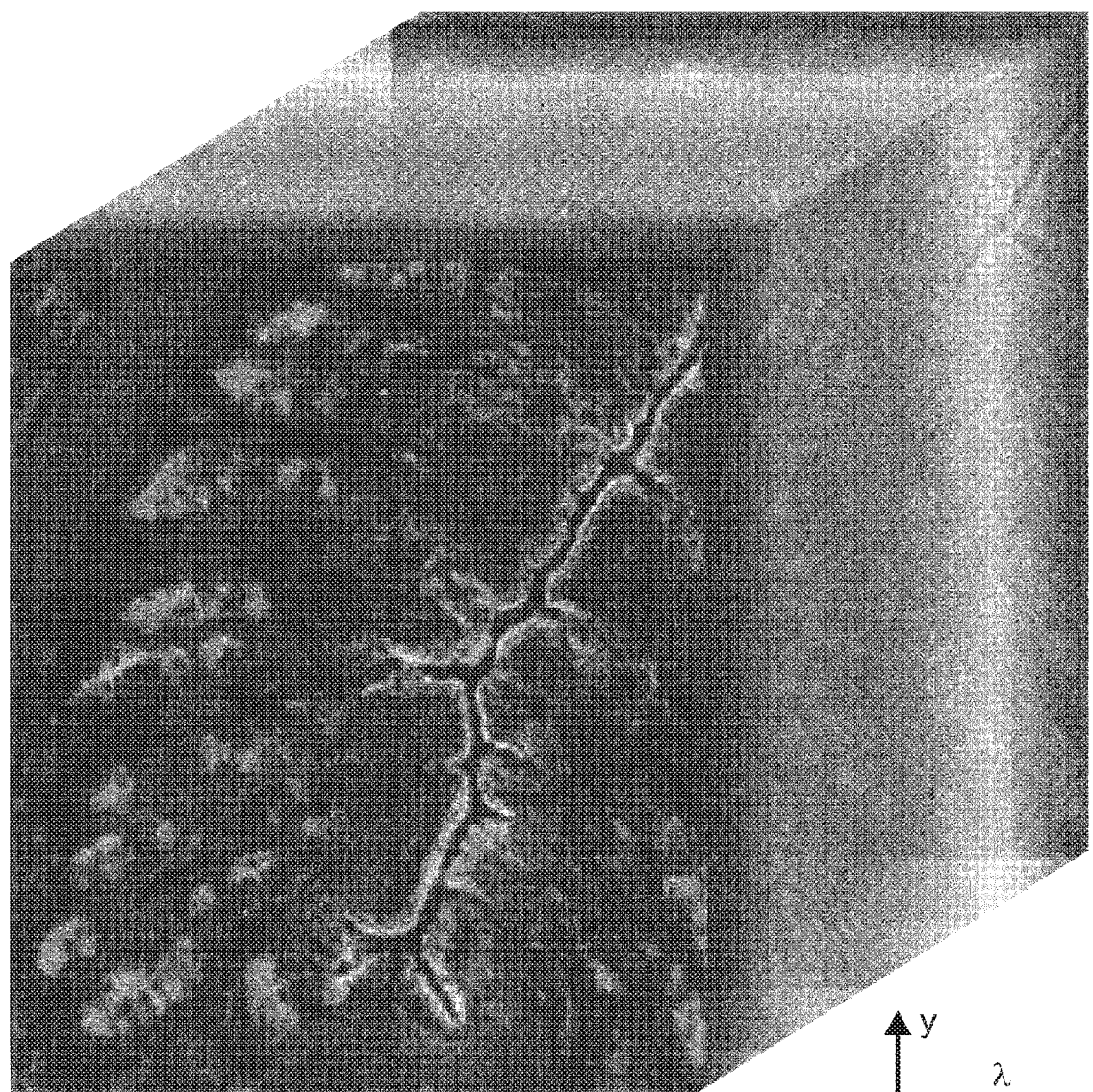
FIG. 1A is an example of a multispectral image acquired with a typical multispectral imaging (MSI) system.

While there are various multispectral imaging systems, an operational aspect that is common to all MSI systems is a capability to form a multispectral image such as that schematically presented in FIG. 1A, for example A multispectral image is one that contains image data captured at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

Figure 1B:
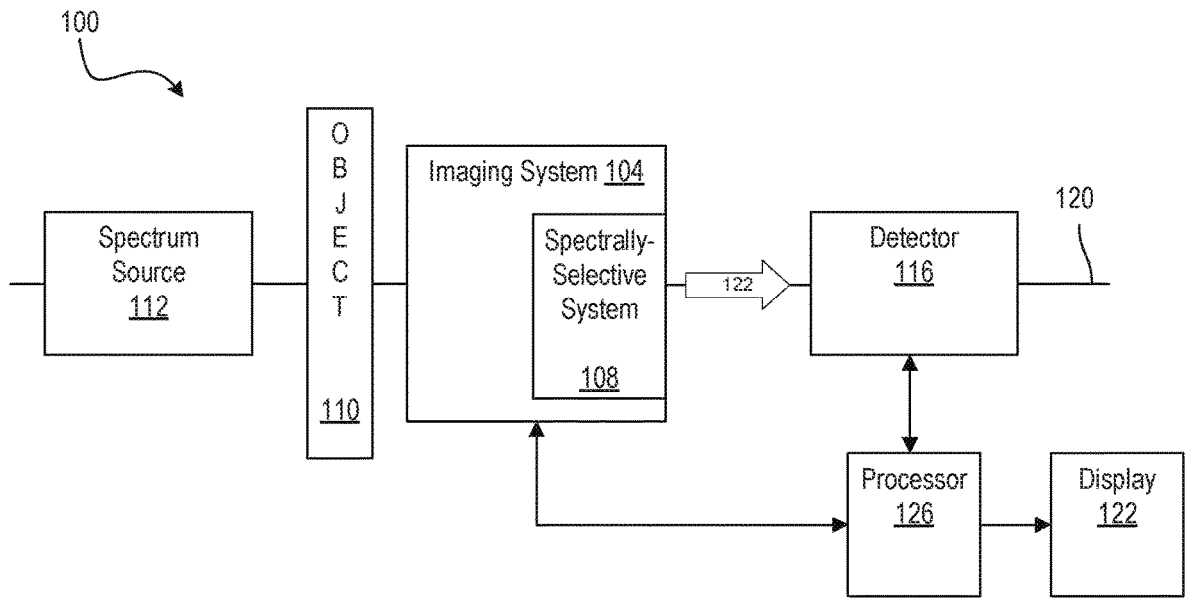
FIGS. 1B and 1C are schematic illustrations of typical MSI systems.
Figure 1C:
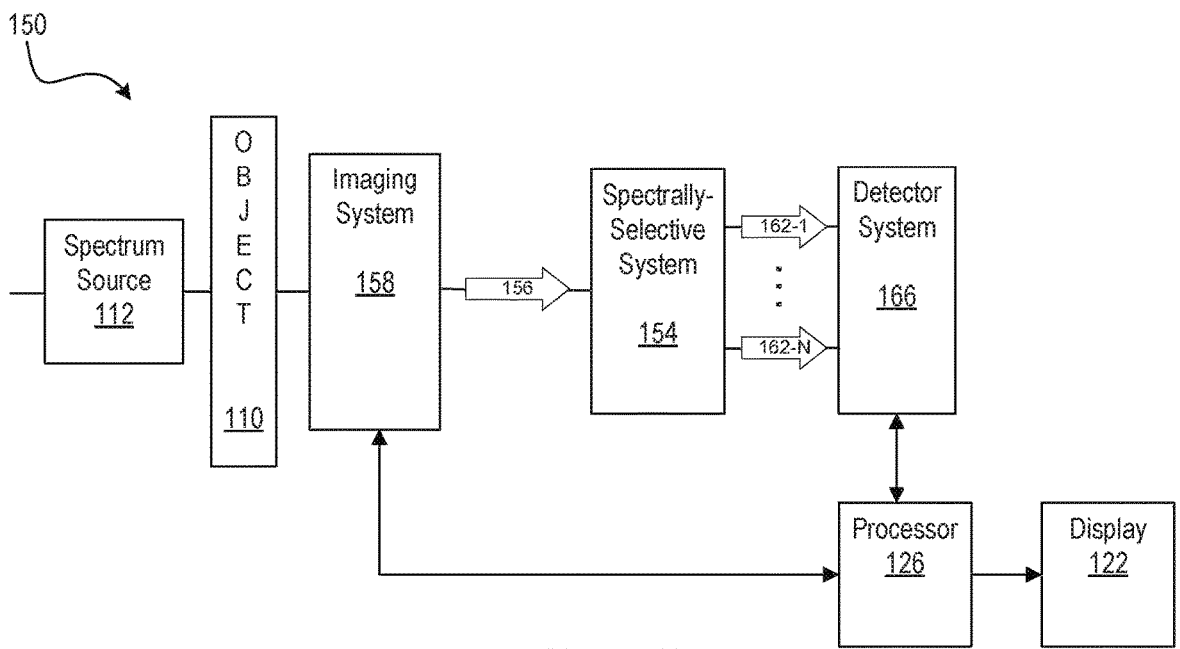
Figure 2A:
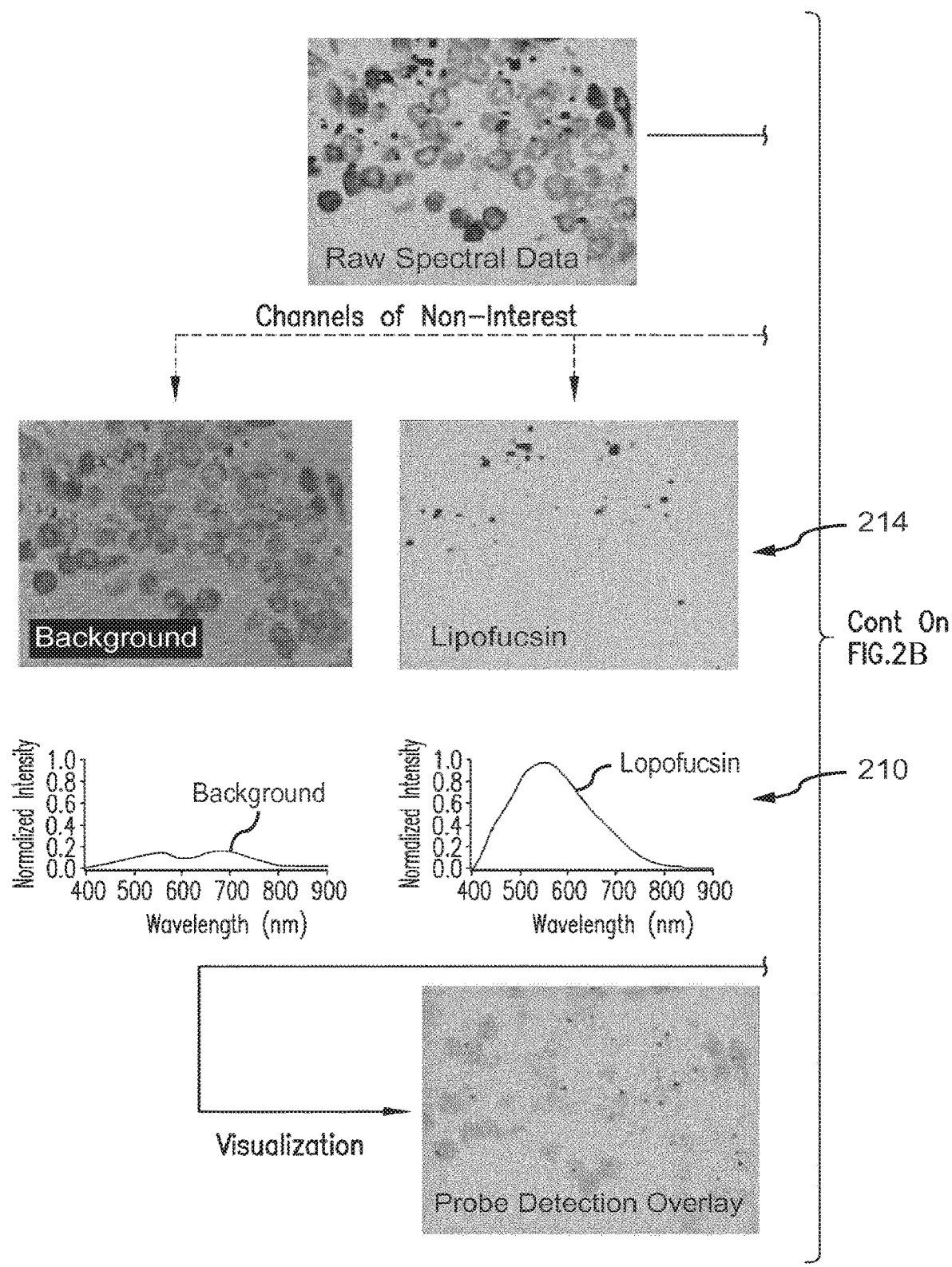
FIGS. 2A-2C are block-schemes illustrating the principle of linear unmixing.
Figure 2B:
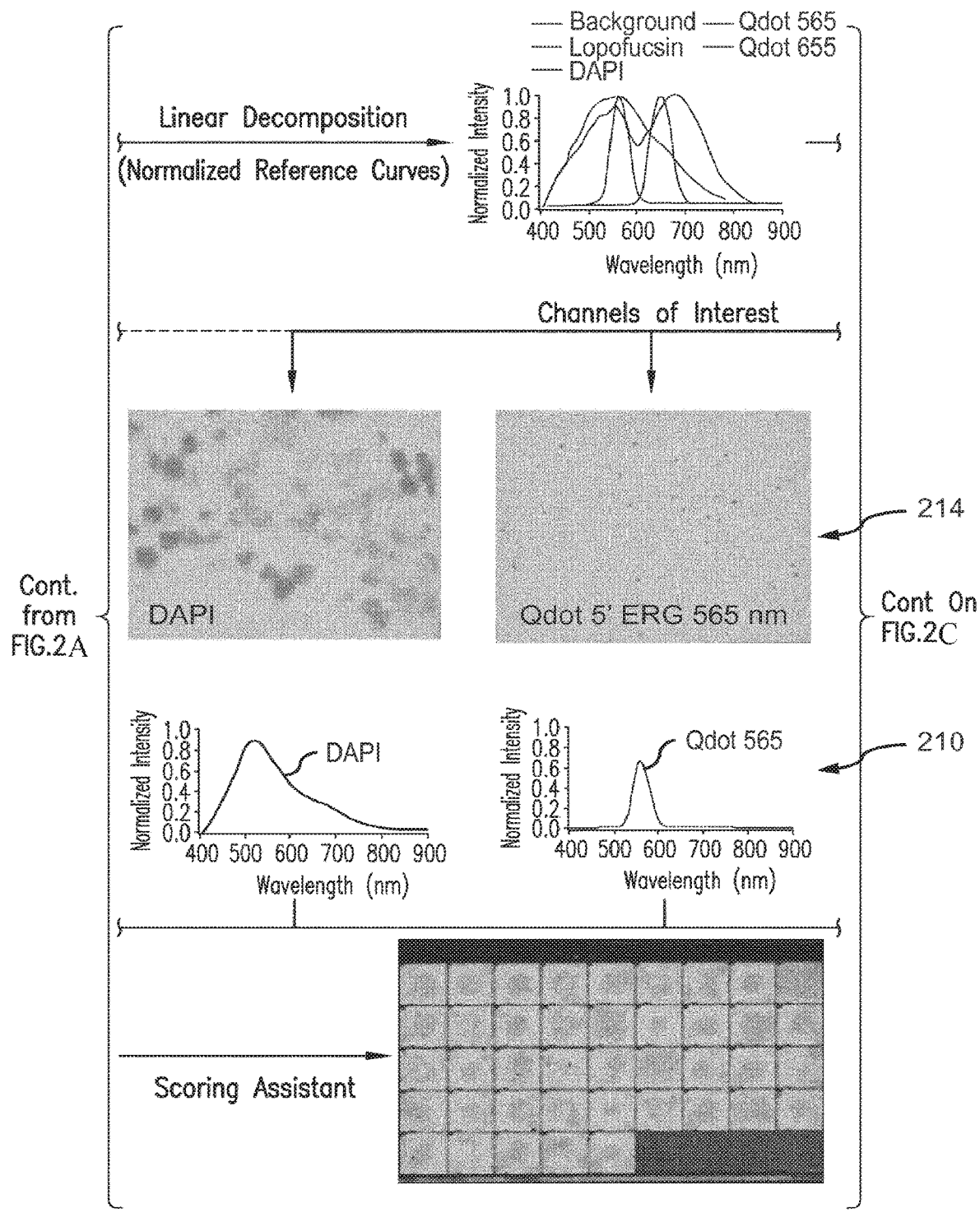
Figure 2C:
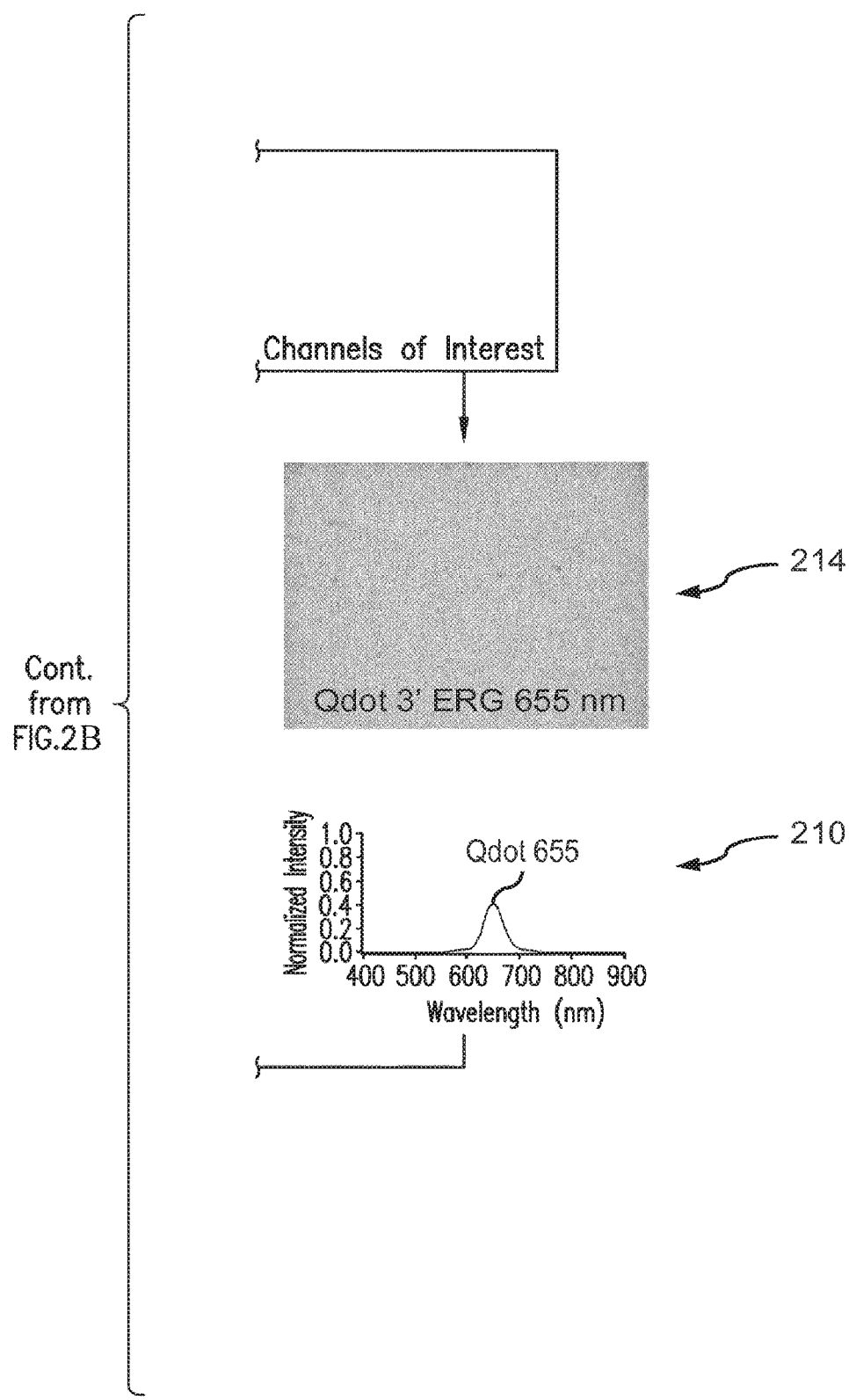

Two common types of MSI systems facilitating the acquisition of images of a specimen are schematically and generally illustrated in FIGS. 1B and 1C. FIG. 1B shows a system 100 including an imaging system 104, for example an optical imaging system, a portion 108 of which contains a spectrally-selective system that is tunable to define a pre-determined number N of discrete optical bands. The imaging system 104 is adapted to image an object, for example, a tissue sample 110, transmitting, absorbing or reflecting illumination from a spectrum source 112, such as a broadband light source or other source of radiation onto a detector 116 (e.g., optical detectors, light sensors, image sensors, CCDs, photodetectors, photosensors, spectral camera, etc.). In an exemplary embodiment, the detector 116 is included in the imaging system 104. As shown, in FIG. 1B, the imaging system 104, which in one embodiment may include a magnifying system such as, for example, a microscope having a single optical axis 120 generally spatially aligned with an optical output 122 of the imaging system 104. The imaging system 104 forms images of the object 110, for example, a sequence of images of the object 110 as the spectrally-selective system 108 is being adjusted or tuned (for example with a computer processor 126) such as to assure that images are acquired in different discrete spectral bands. The system 100 may additionally contain a display 122 in which appears at least one visually-perceivable image of the tissue from the sequence of acquired images. Alternatively, the display 122 is a touch screen display. The spectrally-selective system 108 may include an optically-dispersive element such as a diffractive grating, a collection of optical filters such as thin-film interference filters or any other system adapted to select, in response to either a user input or a command of a processor 126 (which may be a pre-programmed processor), a particular pass-band from the spectrum transmitted from the spectrum source 112 through the object 110 towards the detector 116.

An alternative implementation 150 of a system adapted to simultaneously take a multiplicity of spectrally-discrete optical images in several spectral bands is shown in FIG. 1C. Here, the spectrally-selective system 154 defines several optical outputs corresponding to N discrete spectral bands. The system 154 intakes the transmitted light output 156 from the imaging system 158, (e.g., an optical system) and spatially redirects at least a portion of this light output, simultaneously, along N spatially different optical paths 162-1 through 162-N in such a way as to image the sample 110 in an identified spectral band onto a detector system 166 along an optical path corresponding to this identified spectral band. It is appreciated that another alternative embodiment (not shown) may combine features of the embodiments 100 and 150. The use of such spectral imaging devices for fluorescence microscopy enables high-value diagnostics of various samples (for example, biological tissues) using fluorophores, such as multiplexed nucleic acid and protein markers.

Figures 1, 21A:
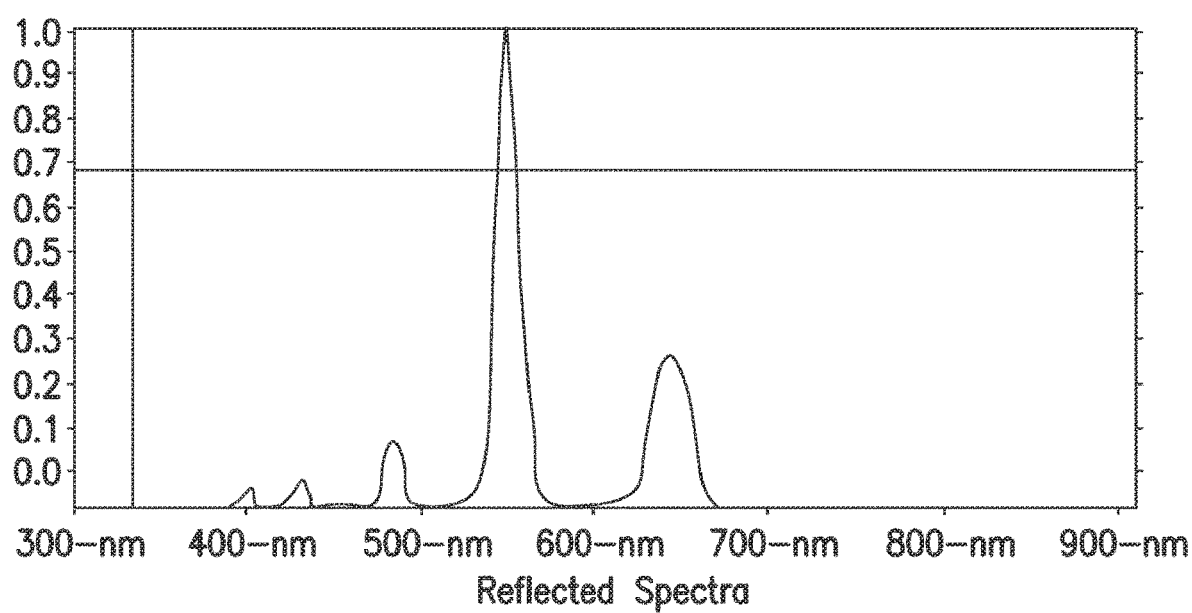
Figures 2, 21A:
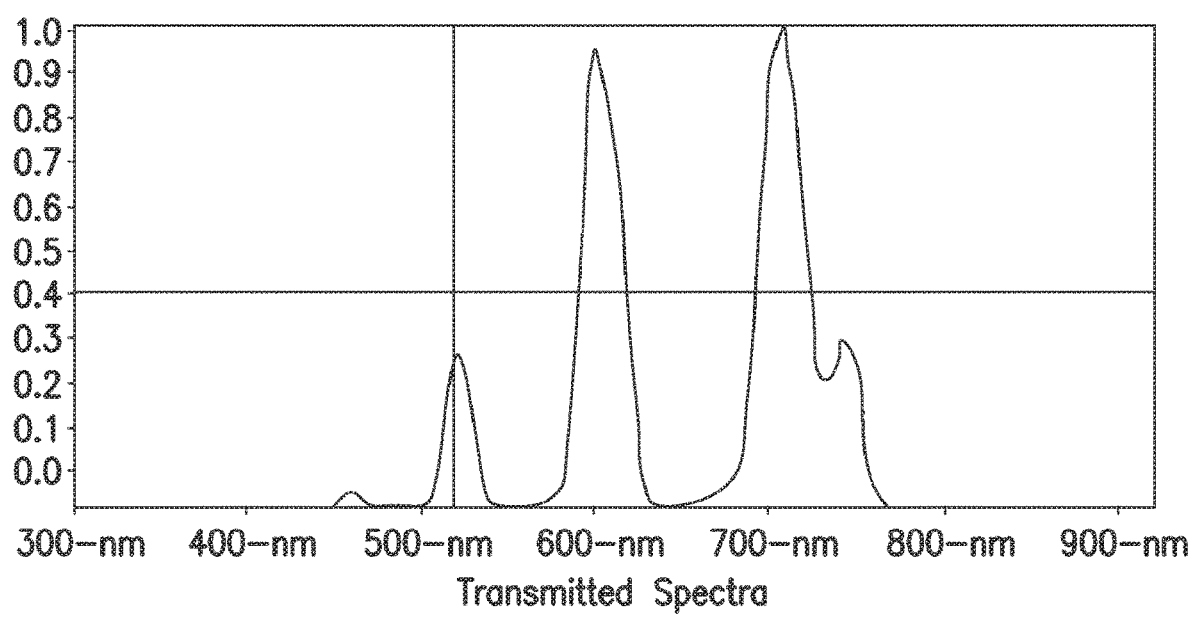
Figures 3, 21A:
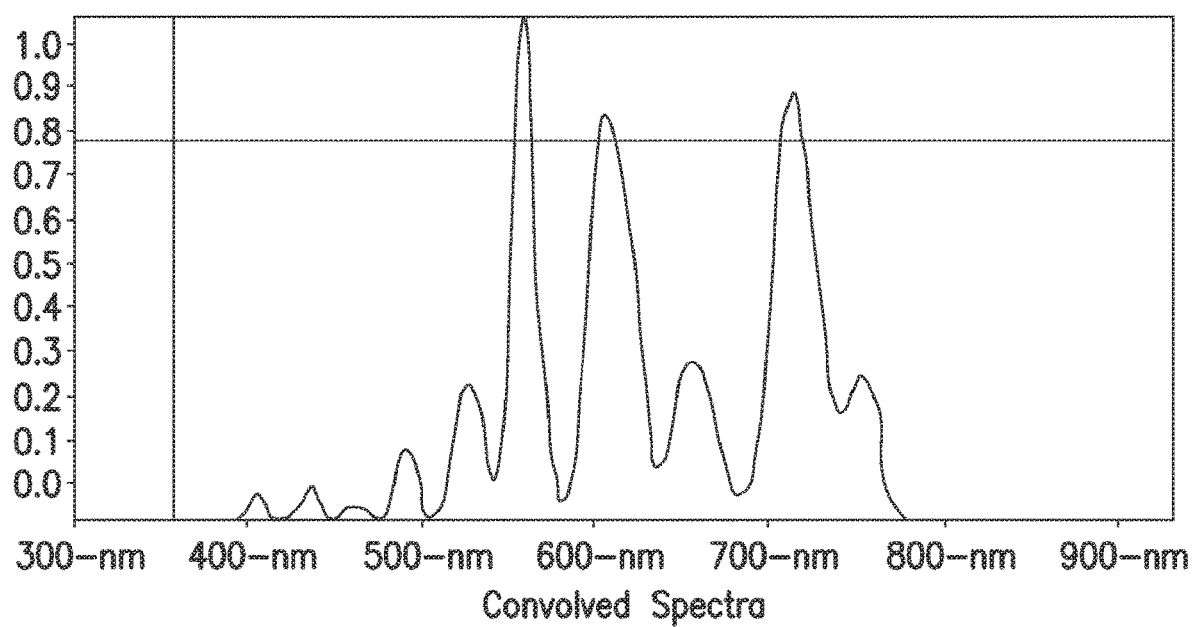

As shown schematically in FIG. 2, the spectral data produced by such instrumentation can be decomposed into different acquisition portions or "analyte channels" 210 that represent the relative contributions of different analytes or fluorophores 214 used with the sample to the acquired overall emission spectrum. FIG. 2 provides illustration to the principle of linear unmixing (also sometimes termed "spectral deconvolution" or "spectral decomposition"). According to this principle, the spectral data of the original spectral data cube such as that of FIG. 1A is computationally compared to known reference spectra of, for example a particular analyte; and then the linear unmixing algorithm is used to separate the known spectral components into 'channels' that represent the intensity contribution (e.g., the net intensity) of each analyte at each pixel. Such analyte-specific information is useful, for example, for interrogating relative analyte concentrations and can provide a new depth of information for diagnosis and/or prognosis of a particular disease and its status by a physician. The useful result of interrogation comes from separation of spectral data representing molecules and/or markers of interest from that caused by background light such as background and/or noise fluorescence (for example, from fluorescent metabolic byproducts) and backscattered light. Accordingly, the abilities to acquire high-resolution spectral image data, and unmix or deconvolve mixed spectral contributions to such data caused by different sources of light, is also important for removing contributions of constitutive autofluorescence. The increased signal to noise ratio afforded by spectral imaging better enables accurate determination of localization of a source of light or spectrum of interest in space (referred to as signal localization) that relates to determination of the anatomy of the tissue at hand.

Figure 3:
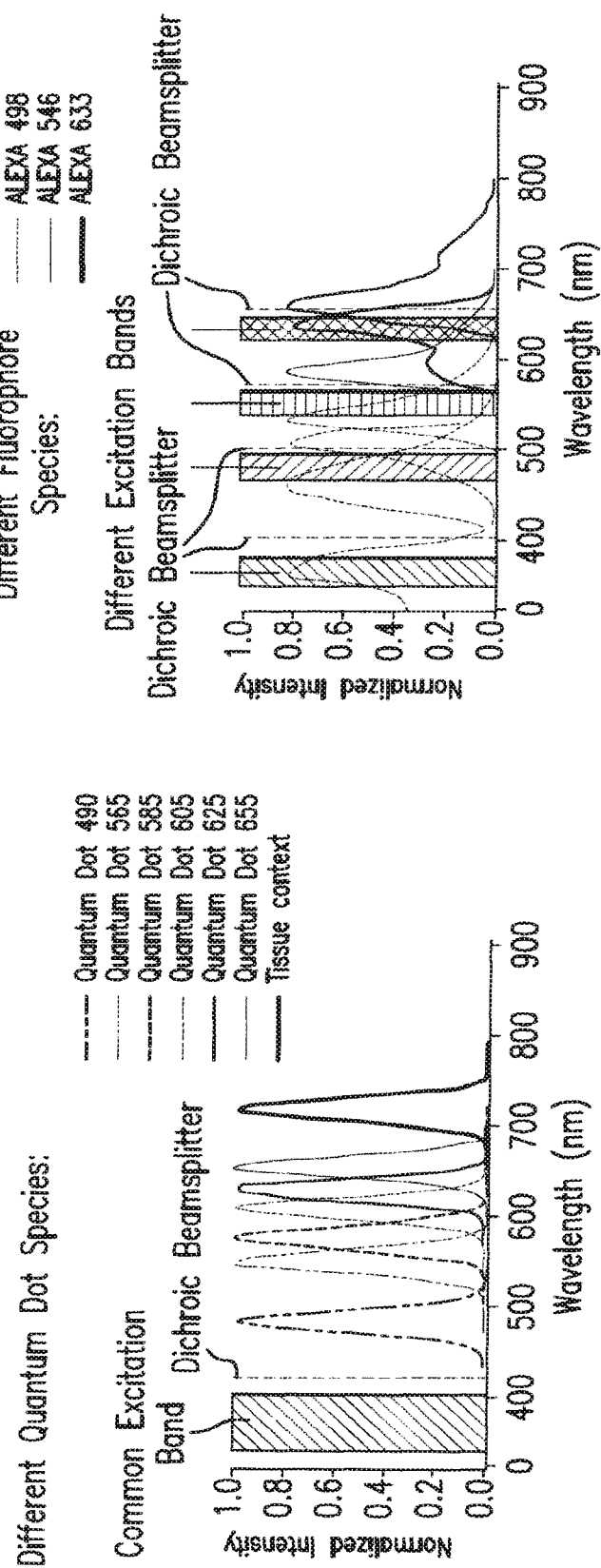
FIG. 3 is a graphical scheme showing comparison of advantages and disadvantages of using quantum dots and chemical fluorophores as markers for quantitative multiplexing.

The use of quantum dots spectral markers offers a number of advantages for multiplex assay technology (FIG. 3). The emission spectra of quantum dots are well approximated with narrow spectral distributions having substantially symmetric intensity profiles. This property facilitates the process of spectral distinction of the quantum dots from other sources of light used as emitting probes or markers. Selections of a multitude of quantum dot species that emit in different spectral ranges across the visible spectrum can be used for multiplexed tissue diagnostics. The emission spectrum of a given quantum dot species is typically defined by physical size of the quantum dot. Because emission spectrum is determined by physical size of the quantum dot, the emission spectrum will not be susceptible to wavelength shifts due to changes, for example, in the chemical or solvent environment in the tissue with which the quantum dots are associated. The excitation spectrum of a quantum dot is rather broad for the majority of the quantum dot emission species and extends well into the UV range. As a result, multiple quantum dot species have overlapping excitation spectra. The resulting possibility of excitation of multiple quantum dot species with radiation within the region of overlapping excitation spectra, for example, with a narrow-band light (substantially a single wavelength that is well separable from the emission spectra of the same quantum dot species), is advantageous because it enables straightforward control of the quantum dot-excitation procedure. Specifically, it allows ensuring that substantially the same amount of excitation light is delivered all to analytes of the sample. Quantum dots are also known as substantially photostable species.

The abovementioned excitation characteristic of quantum dots differs from that of chemical fluorophores. In contrast to quantum dots, different chemical fluorophores emitting at different wavelengths typically require excitation at different wavelengths of the visible spectrum. For that reason, using chemical fluorophores as markers with biological tissue may complicate the excitation process. In particular, the use of multiple chemical fluorophores associated, as markers, with the tissue requires a multi wavelength excitation scheme. In addition, it becomes non-trivial to ensure that contributions of different multiple chemical fluorophores to the overall multiplexed emission spectrum accurately reflect relative concentrations of chemical fluorophores used with the tissue as spectral markers.

A schematic comparison of specific characteristics of spectral detection involving quantum dots and chemical fluorophores/dyes is provided in FIG. 3. Spectral properties of chemical dyes, such as broad emission bands, narrow absorption spectra, and susceptibility to photobleaching are drastically different from those of the quantum dots, which have narrow emission bands, broad absorption spectra, and strong resistance to photobleaching. As a result, methods of calibration of image-acquiring instrumentation designed for quantum dot quantum dot-based imaging are poorly adapted to image acquisition based on chemical dye fluorescent standards with the use of the same equipment. In practice, confirmation of accuracy of the measurement is difficult to achieve because such accuracy depends on the use of samples with analytes 1) of know concentrations; 2) that are photostable; and/or 3) have properties consistent with the experimental samples.

Commercially available fluorescent standards for calibration of image-acquisition equipment are typically associated with and/or adsorbed to beads designed for use with flow cytometry. For example, depending on a system of optical filters used with an image-acquisition system, results of the spectral unmixing analysis of the emission spectrum obtained with the use of such chemical markers may often become simply irreconcilable with standard calibration specifications of the system. The use of beads may, in some cases, complicate obtaining a large sample size per field (which would otherwise increase the signal-to-noise ratio, SNR, in the measurements). Large beads may produce a lens-like effect due to their curved geometry and/or contribute to the same image from different object planes.

Therefore, in order to precisely and reliably use standards in multi-analyte spectroscopy, and to ensure consistent and accurate data acquisition from the tissue specimen, and to permit accurate assessment of relative contributions of the analytes to the overall emission data, such calibration of the multi-analyte MSI system at a system level is required that is not currently provided for. The unmet need arises, in part, because of the lack of appropriate calibration standards. In addition, parameters of computational spectral deconvolution or unmixing algorithms used to process the image data acquired with such MSI system must also be properly configured and confirmed to produce results that reflect actual spectral distributions. Thus, it is important to specify, for example, dynamic ranges for the development of both a measurement system and staining assay(s).

This also calls for development of methods for reliable verification of the results of a spectral unmixing image-data processing. The unsolved problem that this application is addressing is, therefore, at least four-fold: (i) to devise system(s) and method(s) for characterization and/or calibration of performance of such imaging system that permit(s) the use of the system with a multitude of different fluorescent specimens (i.e., to effectively decouple the performance of the imaging system from being linked to the use of a specified specimen); (ii) to provide a test of the spectral performance of the whole MSI system (an integrated system level test); and (iii) to evaluate and express operational parameters performance of the MSI system in terms of standardized units and (iv) to determine the acceptable staining detection range that must be met to ensure performance according to specifications.

The integrated system level tests are important, for example, in 1) validating unmixing performance of an algorithm, for example, an image analysis algorithm and/or a system involving multiplexed quantum dot reporters, and 2) may be tailored to reflect quantum dot emission wavelengths for a plurality (for example, 6 or 7 or 8 or more) analytes across the visible spectrum and into the IR range. The systems and methods proposed below, unlike conventional testing methods that express relative intensities as arbitrary units, facilitate interpretation of the analyte channel and raw data intensity information in terms of standardized intensity units (SIU) and, therefore, permit meaningful comparisons of intensity data from different instruments. The ability to express both signal and noise (or other operational characteristics) in terms of standardized units permits meaningful specification and comparison of SNRs of imaging data acquired with the use of different MSI systems under standardized conditions and enables the comparison of operational performance of different instruments. This advance provides, for example, the ability to define the dynamic range limitations in defined measures of instrument performance, and to isolate instrument dynamic range from the dynamic range of fluorescent signaling technology.

Figure 4A:
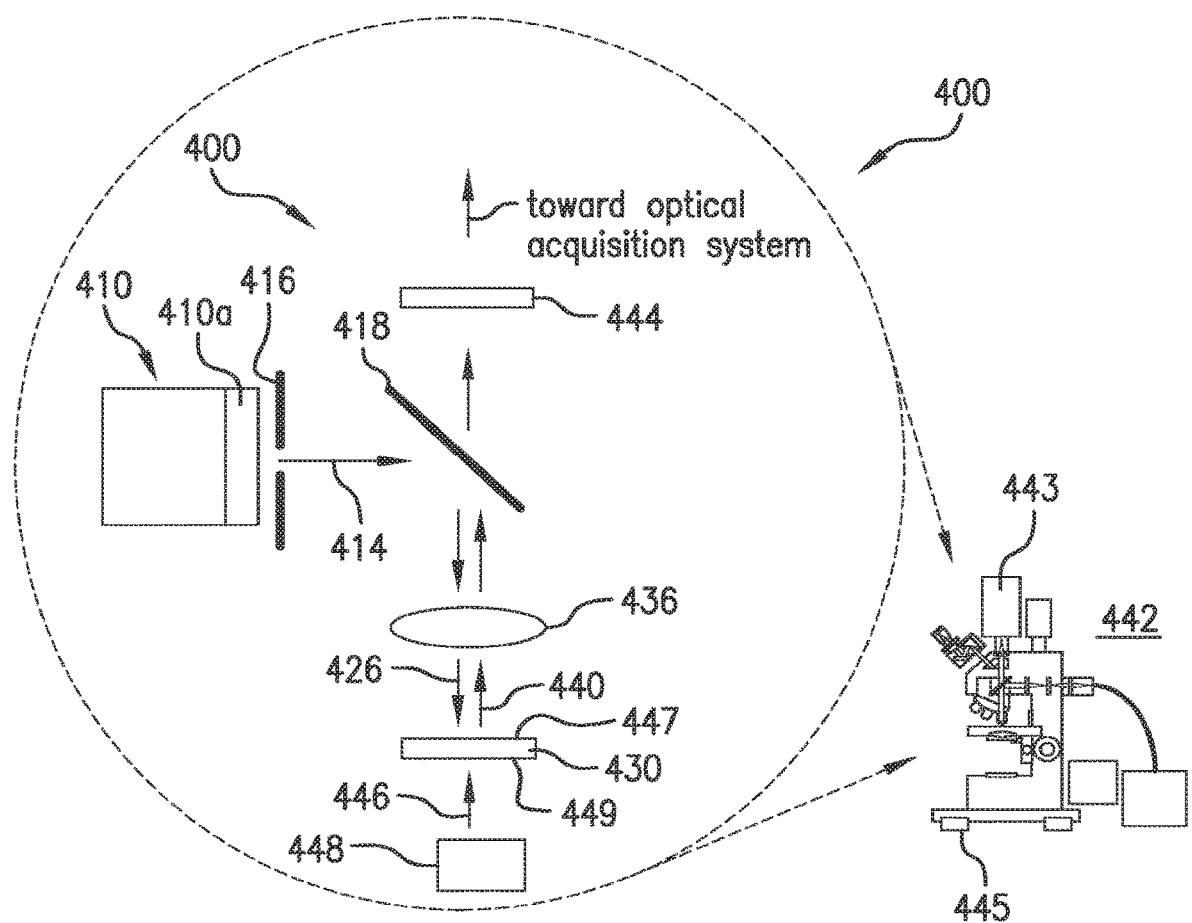
FIG. 4A is a schematic of an embodiment of an illumination channel of a MSI system containing a first calibration source of light including a calibrated light emitter and a calibration optical filter.

Components of an exemplary embodiment of an image acquisition system 400 in accordance with the present invention are shown in FIG. 4A. The exemplary image acquisition system 400 includes a spectrum source 410, for example, a light source. In an exemplary embodiment of the present invention, the spectrum source 410 is configured to include a spectrum emitter, having well-defined spectral properties (e.g., an Hg-lamp, xenon or other arc lamp, laser lines, luminescent radioactive standards, chemiluminescent standards, phosphors, and/or LEDs) The power and temperature of the spectrum source 410 may be stabilized and monitored with closed loop electronic circuitry and/or a multi-bandpass filter 410a. The multi band-pass filter 410a has n predefined pass-bands and is positioned in front of the spectrum source 410. In exemplary embodiments of the present invention, a spectrum acquisition system 442, for example, a microscope based light acquisition device, includes or is coupled to a spectral camera 443. The spectrum acquisition device 442 includes a scanning platform 445 that moves along an axis, for example, along an x and/or y axis, and is utilized to scan an object (which may be placed on a platform), such as slide and/or biological specimen, such that an image of the object can be captured.

According to an embodiment of the invention shown in FIG. 4A, the image acquisition system 400 includes a first spectrum source 410, that is configured to provide spectrum, for example, excitation light, having spectral characteristics defined by the spectrum source 410. In exemplary embodiments of the present invention the spectrum source 410 is a broadband light source (for example, having an emission spectra between 350-nm_and 700-nm) used for fluorescent imaging applications. In an exemplary embodiment of the present invention, the spectrum source 410 a self-calibrating light source, and the power and temperature of the light source is stabilized and monitored with a closed-loop electronic feedback circuitry.

Figure 4B:
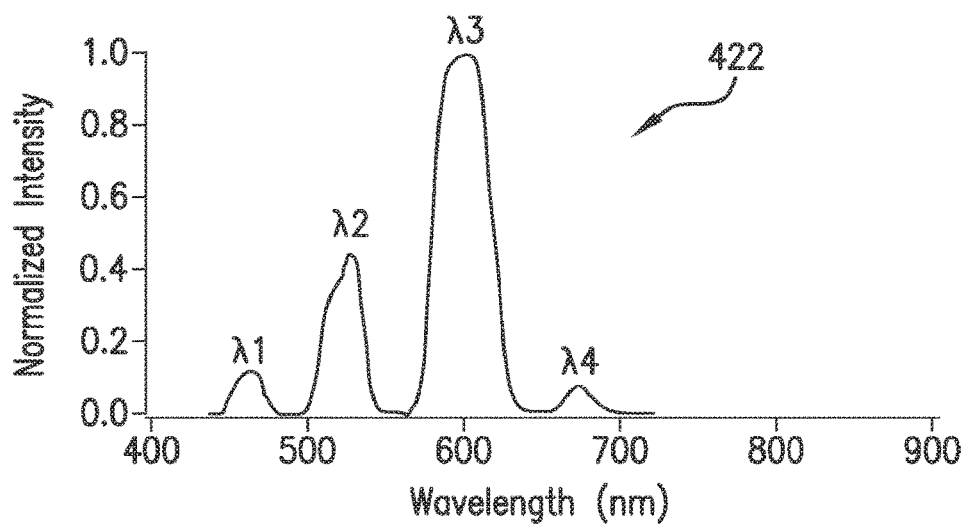
FIG. 4B is a graph representing spectral distribution of intensity of the first calibration source of light of FIG. 4A.

The image acquisition system 400 also includes a spectrally selective system 410a, (e.g., a multi-bandpass filter 410a which has n predefined pass-bands and is positioned in front of the spectrum source 410). In one embodiment, the spectrally selective system 410 is configured to ensure that transmission of light between any two of its adjacent pass-bands is substantially blocked (for example, reduced by at least 3 orders of magnitude as compared to the highest transmission level of the filter). Consequently, light 414, which that is produced by the source 410, may pass through a chromatically neutral mechanism 416, for example, an iris diaphragm 416 of the spectrum source 410, and impinge onto the beamsplitter 418 (such as, for example, a 50/50 beamsplitter), and has a predetermined calibration spectrum 422, as shown in FIG. 4B. By utilizing, for example, the spectrally selective system 410a, the spectral properties and power of the spectrum (e.g., light) 414, such as the intensity and wavelength of the spectrum 414 that will impinge on the sample 430, can be determined before the sample/object 430 is placed in the path of the radiation or illumination. In exemplary embodiments of the present invention, the iris diaphragm 416, located at the pupil plane, is opened or closed, to various degrees, to vary the spectrum 414 output from the spectrum source 410.

A portion of light 414 passes through an optical system 436 (such as a lens system having at least one lens) and forms an incident beam 426. Incident beam 426 then reaches a first side 447 of the object 430, for example, a partially reflective and partially transmissive (i.e., transflective) substrate, such as, a microscope slide, after passing through the optical system 436.

Light 440 reflected from the object 430 is received and detected by a component of the MSI system (for example, the spectral camera 443) after traversing a filter 444, such as a neutral density filter. In an exemplary embodiment of the present invention, the filter is an ND3 filter, identified as part no.XB27/25R and manufactured by Omega Optical of Vermont. The filter 444 is utilized to attenuate intensity of measured light to reduce it to levels comparable to the intensity levels consistent with fluorescent samples. In a related embodiment, the image acquisition system 400 may have a second spectrum source 448, on the opposite side of the object 430, for example a transmissive light source that generates a beam 446 having its own spectrum, that is incident onto a second side 449 of the object/sample 430, such that the spectrum from the second spectrum source 448 passes through the object/sample 430 towards the spectrum acquisition device 442. The second spectrum source 448 may be an alternative to the spectrum source 410, or may be provided as an additional spectrum source.

Figure 5A:
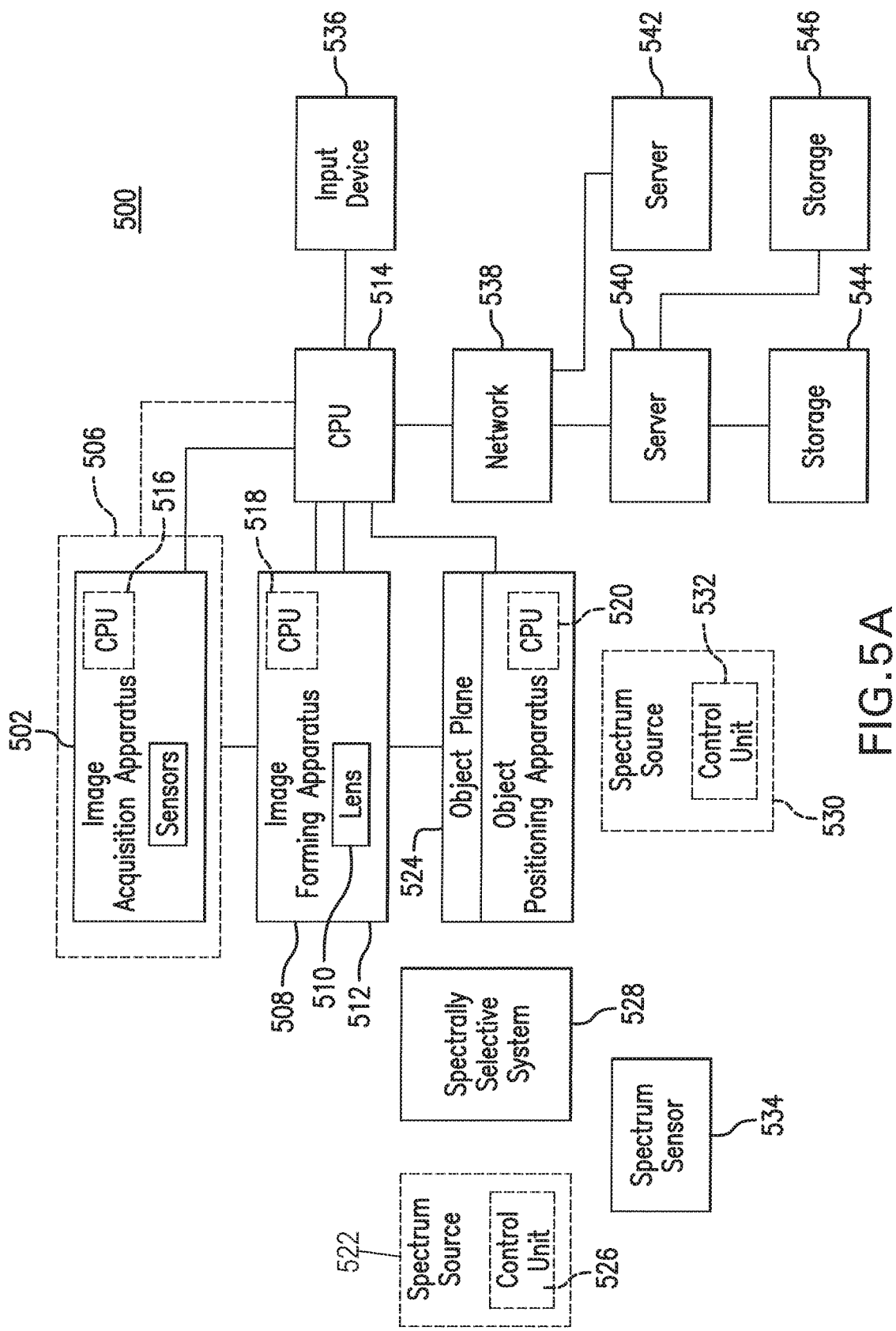
FIG. 5A is a block diagram of an exemplary embodiment of an imaging system, in accordance with the present invention.

Shown in FIG. 5A, is a block diagram of another exemplary embodiment of an imaging system 500, in accordance with the present invention. In an exemplary embodiment of the present invention, the imaging system 500 is a spectral imaging system that includes an image acquisition apparatus 502, such as a spectral camera having sensors 504 that receive light. In an exemplary embodiment of the present invention, the image acquisition apparatus 502 is included in a scanner 506. The system 500 includes an image forming apparatus 508 coupled to the image acquisition apparatus 502. In exemplary embodiments of the system 500, the image forming apparatus 508, for example, (1) includes at least one lens 510; (2) is an optical train; and/or (3) is a microscope. An object positioning apparatus 512 is coupled to the image forming apparatus 508. In exemplary embodiments of the present invention, the object positioning apparatus 512 is utilized to position an object, for example, a slide, for obtaining single images or scanned images. In an exemplary embodiment of the present invention, the object positioning apparatus 512 is, for example, a microscope stage that is part of a microscope. In exemplary embodiments of the present invention, the object positioning apparatus 510 may move in at least one of an x-direction, y-direction, a z-direction, a rotational direction, and an angular direction.

The system 500 and/or each of the systems' components (e.g., image acquisition apparatus 502, the image forming apparatus 508, and the object positioning apparatus 512 may be controlled by a single CPU 514. It should be understood by one skilled in the art that a CPU 516, 518, 520 may, alternatively or additionally, be included in or coupled to any one of the components of the image acquisition apparatus 502, the image forming apparatus 508, and/or the object positioning apparatus 512, respectively.

A first spectrum source 522 provides spectrum, such as light, for the system 500, and, in an exemplary embodiment of the present invention, delivers spectrum to a plane 524 of the object positioning apparatus 512. In an exemplary embodiment of the present invention, the spectrum source 522 may include a control unit 526 that is utilized to control, select or enter the desired spectrum output wavelength or wavelength range of the spectrum source 522. In an exemplary embodiment of the present invention, the first spectrum source 522 is a self-calibrating source (i.e., a source having its own sensor that monitors and helps to regulate the spectrum output), such as a self-calibrating light source identified as part number P010-00201R, manufactured by Lumen Dynamics of Ontario, Calif. (city and state). In an exemplary embodiment of the present invention the spectrum source 520 is coupled to the image acquisition apparatus 502. In an exemplary embodiment of the present invention, a spectrally selective system, such as spectrally selective system 528, may be placed in the path of the spectrum source 522. The system 500 may also include a second spectrum source 530, for example, a transmission light source that illuminates a side of an object, which is placed on the object positioning apparatus 512, on a side opposite to the side of the object receiving incident spectrum from the first spectrum source 522. In an exemplary embodiment of the present invention, a spectrally selective system, such as spectrally selective system 528, may be placed in the path of the spectrum source 530. In an exemplary embodiment of the present invention, the second spectrum source 530 may include a control unit 532 that is utilized to control, select or enter the desired spectrum output wavelength or wavelength range of the spectrum source 530. In an embodiment of the present invention, the spectrum control unit 526,532 is any device or method that regulates the output of the spectrum source 410, and may include filters. In an exemplary embodiment of the present invention, the spectrally selective system 528 may be external to the spectrum source 522,530. In an exemplary embodiment of the present invention a spectrum control unit 526,532 includes a meter or sensor. In an exemplary embodiment of the present invention, the spectrum control unit 526,532 regulates the output of spectrum from the spectrum source 522, 530 before it traverses the imaging system 500, or components thereof (such as, the image forming apparatus 508 (e.g., optical train)). A sensor or meter 534 is utilized to sense, measure and/or characterize spectrum provided to the system 500, by the first and/or second spectrum sources 526, 530, at any point in the system 500. In an exemplary embodiment of the present invention, the sensor or meter may be coupled to any computer or CPU that is internal or external to the system 500, e.g., CPUs 514, 516, 518, and 520.

An input device 536 is coupled to the CPU 512. In an exemplary embodiment of the invention, the input device 536 is a keyboard, mouse, touch pad, or other input device. In exemplary embodiments of the present invention, any or all of the CPUs 514, 516, 518,520 may be connected to a network 538. One or more servers 540,542 and/or storage devices 544,546 may be connected to the network 538 and/or any one or more of the CPUs 514, 516, 518,520. While the devices, apparatuses and/or components of the system 500 are described as part of the system 500, the apparatuses, devices and/or components of system 500 may stand alone or be coupled to the system 500 by a wireline or wireless connection.

Figure 5B:
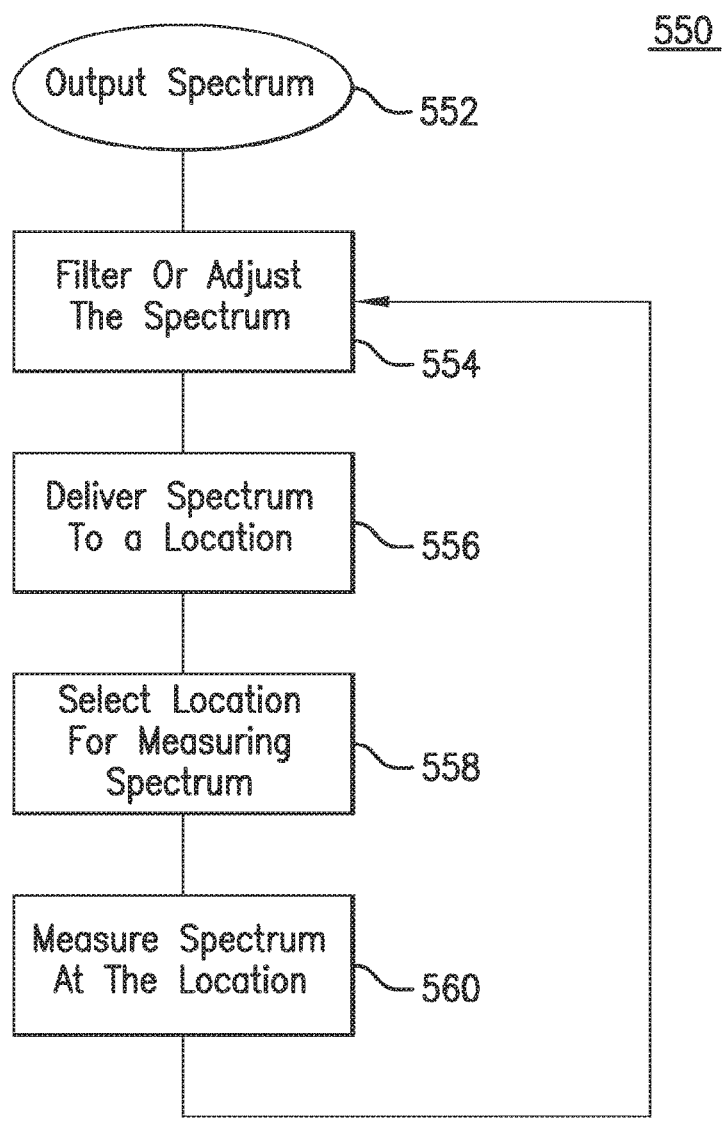
FIG. 5B illustrates one embodiment of a method for measuring the intensity of light transmitted at locations within an imaging system, in accordance with the present invention.

Referring now to FIGS. 5A and 5B we now describe methods of calibrating a system in accordance with the present invention, for example, the imaging system 500 and/or components of the system 500. Calibration of system 500 may involve, for example, measuring an amount of spectrum intensity, at any location in the system 500 for example, measuring illumination, at or near the object plane 524. The intensity of spectrum output by the spectrum source 522,530 may not match, for example, the amount of spectrum incident at the object plane 524. By ascertaining the amount of spectrum incident at the object plane 524, one can repeatedly deliver that same amount of spectrum (e.g., light) to the object plane 524 (e.g., the site of a tissue sample on a slide). Thus, by identifying the amount of illumination that reaches the object plane 524, an operator of the system 500 is able to standardize an amount of spectrum, for example light, delivered to one or more objects, such as biological specimens, placed at or near the object positioning apparatus 512.

FIG. 5B illustrates one embodiment 550 of a method for identifying the intensity of spectrum at locations within the system 500. This method may be performed for every desired spectrum output, for example, excitation light wavelength output range by the spectrum source 522. The method 550 starts with step 552 in which the spectrum source 522 is turned on, such that spectrum is output from the spectrum source 522. In step 554, spectrum output may be filtered and/or adjusted (e.g., by the spectrally selective system 528 or control unit 526, such that the spectrum output correlates to a particular wavelength or band, and filtered and/or adjusted spectrum output is generated.

Steps 554 through 560 may be repeated to measure a characteristic of spectrum of a second and/or different wavelength or band generated by the spectrum source 522. In another embodiment of the invention, steps 554 through 560 may be repeated to measure a characteristic of spectrum of a second wavelength or band generated from a second spectrum source 530. The spectrum wavelength or band of the second spectrum source may be adjusted or filtered to a same or a different wavelength or band as adjusted or filtered for the first spectrum source 522. The steps of method 550 may be continuously repeated for spectrum output of various wavelengths. Thus, for example, the intensity of spectrum attributed to one or more wavelengths at a location in the system 500 is identified, and may be used to standardize or calibrate the system 500 to a known or expected level of performance.

In an exemplary embodiment of the present invention, a spectrally selective system 528, is placed within the spectrum source 522 or is placed in the path of the spectrum source 522, and a spectrum amount is measured at or near the output of the spectrum source and/or the spectrally selective system 528, to determine the performance of spectrum source or another component of the system 500 before the spectrum reaches for example, the image forming apparatus 508. Thus, for example if the intensity or power of spectrum is not what it is expected to be at the object plane 524, then the component that may be causing the unexpected delivered spectrum intensity at the particular location in the system 500 may be more readily identified (e.g., a lens of an the image forming apparatus may not be meeting its expected performance standards.

Calibration of the system 500, shown in FIG. 5A, may also involve determining the dynamic range, i.e., an approximate minimum and an approximate maximum of the sensing capabilities of the image acquisition apparatus 502, for example, a spectral camera, scanner, or components thereof, such as the camera's sensors. In an exemplary embodiment of the present invention, minimum of the dynamic range is the smallest spectral signal that is sensed by the camera that is measurably above the total noise identified.

Figure 5C:
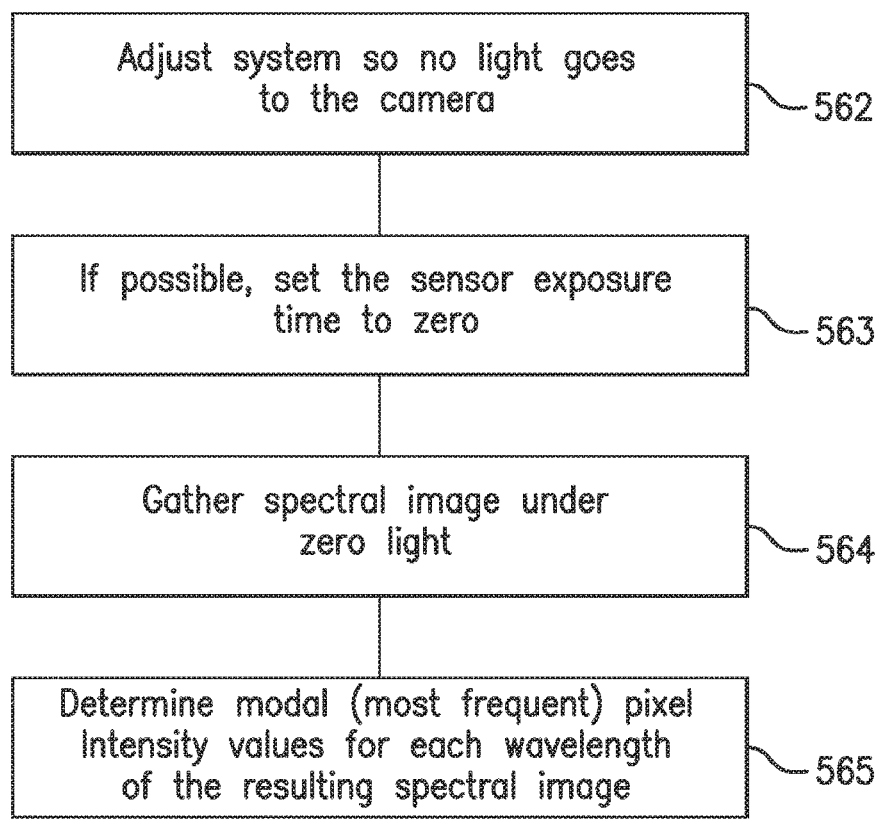
FIG. 5C is a flow chart representing a method for determining the spectral image offset correction data and/or image.

The dynamic range is determined by first ascertaining an intensity offset corrected image and/or pixel offset corrected image data (sometimes referred to a bias image and/or bias image data) without any input from the first or second spectrum source, which will be used to calibrate any images taken subsequent to calibration. FIG. 5C is a flow chart that represents a method 560 for determining the offset value to be applied to all image data to correct the offset of the intensity values due to the camera electronics. In step 562, the system is configured so that light is blocked from transmitting to the image sensor. In step 563, the sensor or camera of the system is set to acquire images with zero exposure time to ensure that no stray light is accumulated while determining the offset value. In step 564, a spectral image is acquired with these settings (this is effectively an image of 'nothing', therefore any intensities that do show up are due to electronics of the camera). From the image acquired in step 564, the modal pixel value is calculated at each wavelength image to ascertain the offset of pixel values above zero. This information can be used to subtract this offset, at each wavelength, from all the pixels in subsequent images. The end result is that pixels that do not receive light are set to a value of zero. The modal pixel intensity value of the images captured with no input from the spectrum source is sometimes referred to the bias image, bias image data, bias offset image, pixel offset image, pixel offset value, or pixel offset image data, as it is the pixel offset image, data, and/or value. In exemplary embodiments of the present invention, the offset correction value may be expressed in units of grey-scale value, or electrons (e−) or Coulombs (C), for example. The offset value is applied to images (e.g. spectral images) or spectral image data (e.g., multispectral image data) when an image is later taken of an illuminated field or object (e.g., a biological specimen on a slide) using the system 500.

Figure 5D:
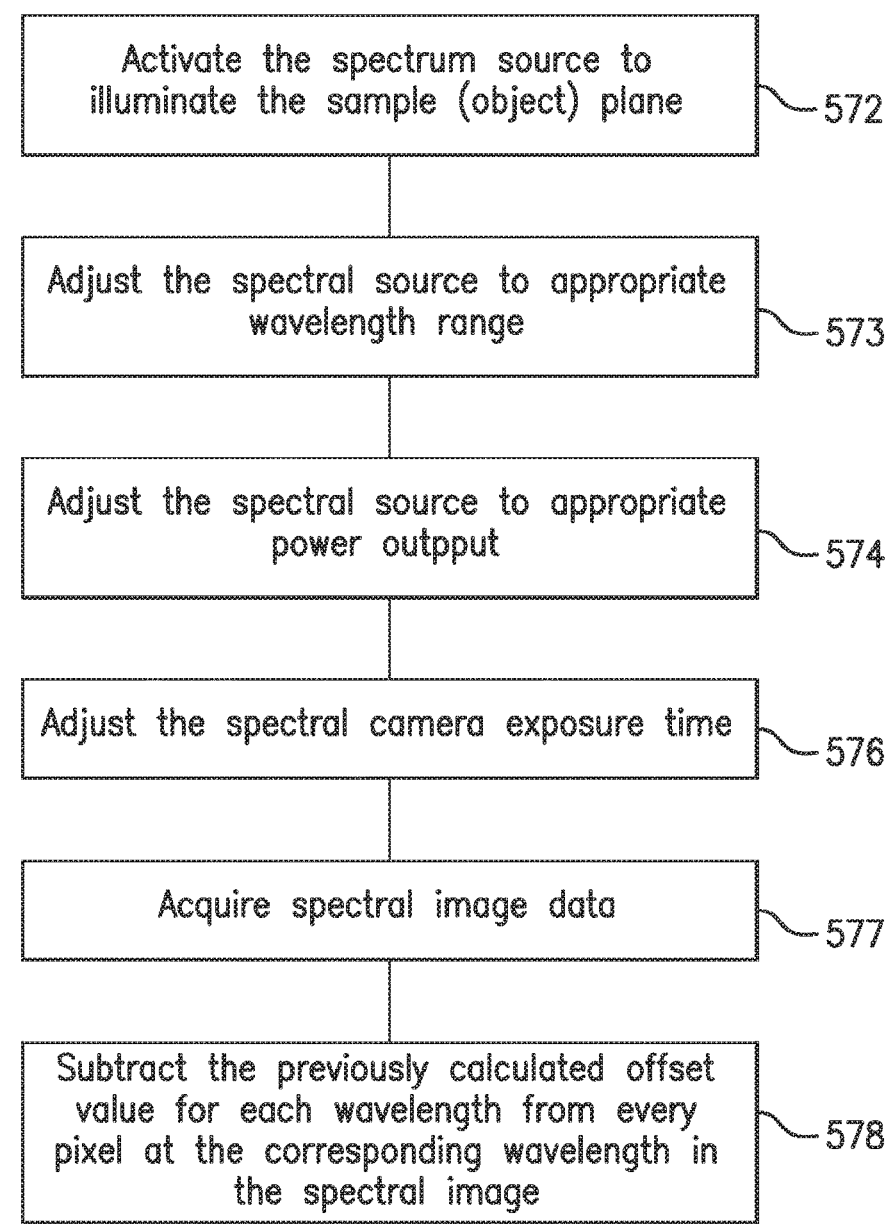
FIG. 5D is a flow chart illustrating a method for correcting spectral images for intensity offset, in accordance with an embodiment of the present invention.

FIG. 5D is a flow chart representing a method 570 for determining a corrected image and/or corrected image data, based on pixel offset correction data and/or image. In step 572, a spectrum source is activated. In step 573, the spectrum output is filtered or adjusted to a specific wavelength or bandwidth. In step 574, the spectral source is adjusted to an appropriate standardized power output for the image acquisition. In step 576, the camera exposure time is adjusted to an appropriate value for the intensity level of the light reaching the camera. In step 577, a first image of an evenly illuminated field is captured by the image acquisition apparatus 502. In step 578, the offset value for each wavelength (previously derived in method 560 outlined above) is subtracted from every pixel, at each corresponding wavelength, of the acquired spectral image. Steps 573 through 577 may be repeated using the same settings to derive a pair of images from which inter-pixel intensity variance can be calculated, and this process may be repeated for various wavelengths, wavelength bands, and/or exposure times.

Determining the dynamic range may also involve the method 600, shown in FIG. 5E, for determining a standard intensity unit conversion for the greyscale values reported by a noise (which includes determining mean and variance multi-spectral camera and this value will be used later for expressing the electronic noise image data) of the imaging system 500, or components thereof (for example the sensors of the spectral camera). In step 602, the spectrum source 522 is activated. In an exemplary embodiment of the present invention, the system 500 is configured, such that the illumination that the imaging acquisition apparatus 502 receives is even or substantially even (e.g., the illumination across the sensors of a spectral camera is even). The intensity level is for each data acquisition to follow is calibrated using a sample plane sensor temporarily placed in the object plane to measure the illumination level and adjust to the desired output at a given wavelength. In step 602, a first image (e.g., spectral/multispectral image) is captured with the image acquisition apparatus 502 while the one or more spectrum sources (e.g., broadband light source or light sources) are turned on. In step 602, a second image is captured by the image acquisition apparatus 502. In step 602 the offset correction value, image, and/or data as identified by the method 570 above, is subtracted from the pixel value at each wavelength of the zero exposure image from each of the first and second images and/or first and second image data to generate a first corrected image and/or first corrected image data (e.g., an image cube of data, such as the spectrum intensity values for each x, y, λ captured) and a second corrected image and/or second corrected image data (e.g., an image cube of data).

In step 603, a resultant difference image data is generated from subtracting the corresponding offset-corrected spectrum intensity values of first and second images and/or first and second sets of corrected image data, respectively. In step 604, spatial characteristics, for example, a standard deviation of the pixel intensity values, for each wavelength/band in the resultant corrected image data and is further used in determining variance values associated with the pixel intensity values at each wavelength or band. In step 604, a variance is determined (e.g., based on the standard deviation, such as by dividing the multispectral standard deviation image data by 2) for each wavelength/band of the resultant difference image data. It should be appreciated by one of ordinary skill in the art that the variance may be determined before the standard deviation is determined. It should be understood by one of ordinary skill in the art that while the methods are described by determining, for example, the standard deviation, variance, and mean, the aforementioned (standard deviation, variance, and mean) are related and thus, may suffice to determine and/or replace one as an alternative for another in the steps of the methods of the present invention. Further, the steps of the present invention, involving, for example, determining the standard deviation, variance, and mean may not necessarily need to be performed in the order described in the methods of the present invention.

In step 605, the mode pixel intensity value at each wavelength of at least one of the first and second corrected image data is generated, determined, or received, and divided into the variance determined in step 604 for the corresponding wavelength/band of the resultant corrected image to generate a conversion value for each wavelength. The resulting conversion value is representative of for example, the number or an approximate number of electrons recorded at each pixel by a CCD sensor in the spectral camera per grey level. As a result, for example, a level of brightness of an image (e.g., a spectral image) is reflected in a standardized unit of measurement (SIU), for example electrons (e). A conversion to the SIUs facilitates the expression of the SNR and dynamic range of the camera in terms of standardized units (as a result of standardized conditions), as well as objective comparison of measurements and/or measurement results between or among different analytical and imaging systems. Standardized conditions are those conditions where, to a highest degree possible, factors that may influence the measurement are controlled and reported such that the measurement conditions can be reliably reproduced and/or modeled.

Figure 5F:
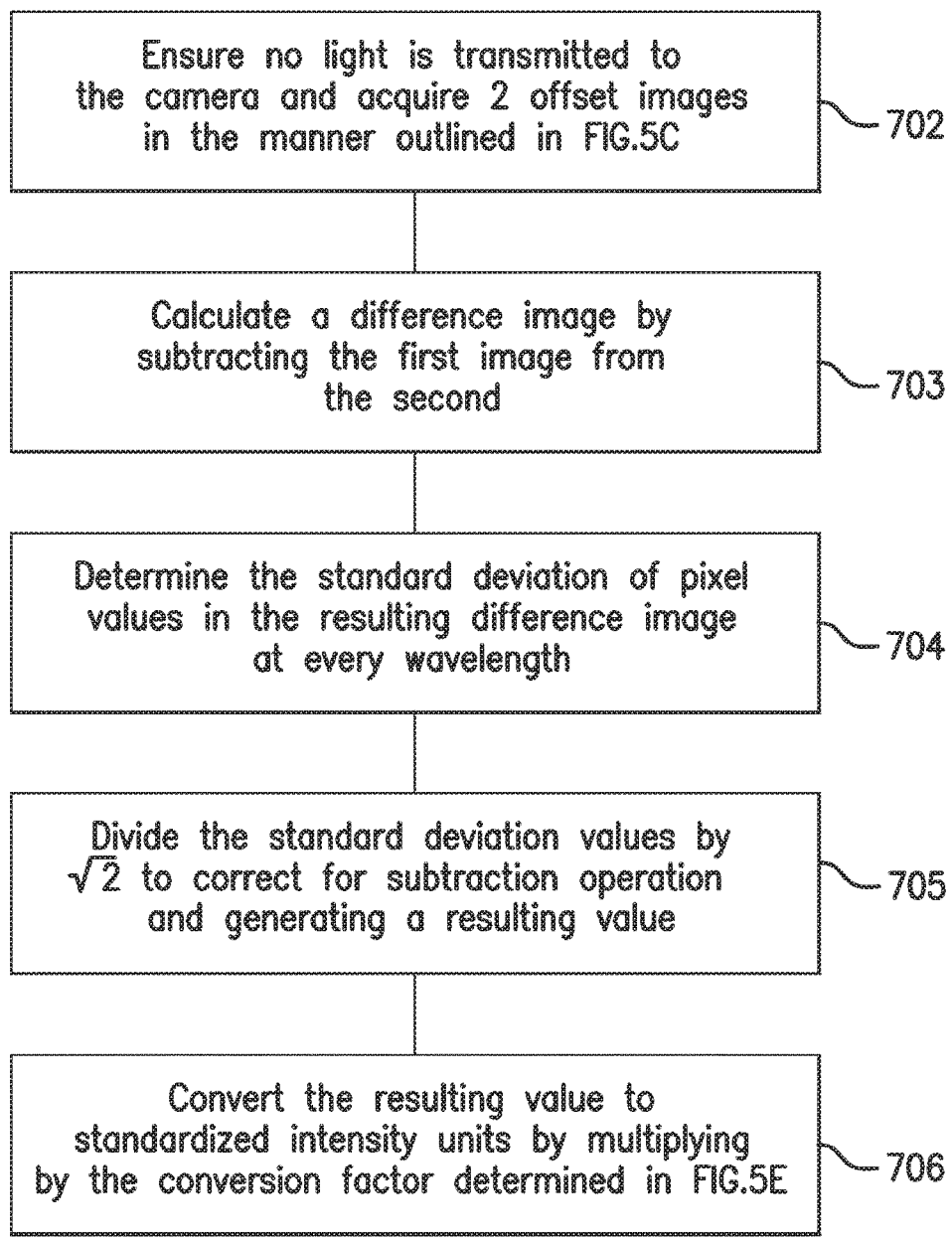
FIG. 5F is a flow chart illustrating method 700 for determining the electronic noise associated with spectral data acquisition in terms of standardized intensity units.

In an exemplary embodiment of the present invention, the noise associated with sensor electronics of a data acquisition system is generally a primary factor limiting the dynamic range of an MSI system employing the CCD technology. According to an embodiment of the invention, the determination of image-acquisition noise involves the following steps illustrated in method 700 (FIG. 5F):

In step 702, first and second spectral offset (or bias) images are acquired, without any light of the system being activated, as similarily performed in steps 562 through 564 (FIG. 5C).

In step 703, a difference image is generated by subtracting the first offset image from the second offset image. The difference image represents the isolated noise from sensor electronics during data acquisition;

In step 704, the standard deviation of the difference image is calculated;

In step 705, the adjusted value of the standard deviation (for the increase in variability due to subtracting the two images) is corrected or adjusted by dividing the adjusted value by the square root of two, and generating a resulting value.

In step 706, the resulting value is converted to standardized intensity units by multiplying the resulting value by the conversion factor determined in step 606 of FIG. 5E. The resulting value and the converted resulting value correspond to a determined measure of the acquisition noise of the imaging system that may be utilized to develop noise specifications.

The dynamic range is sometimes expressed as a ratio of the maximum and minimum light intensity values that the imaging acquisition apparatus can for example, digitize (i.e., sense and convert the analog signal to a digital signal). In an exemplary embodiment of the present invention, the maximum limit of range is determined by multiply the highest grey level for a particular bit depth (for example, an image having a depth of 8 bits has a highest greyscale level of 255) by the conversion value. The minimum value is at or near the noise floor is or is approximately the conversion value (e.g., the electron conversion value) added to the noise calculated. FIG. 5G illustrates the flow for determining dynamic range at every wavelength for a spectral imaging system at standard illumination and exposure settings.

Figure 6A:
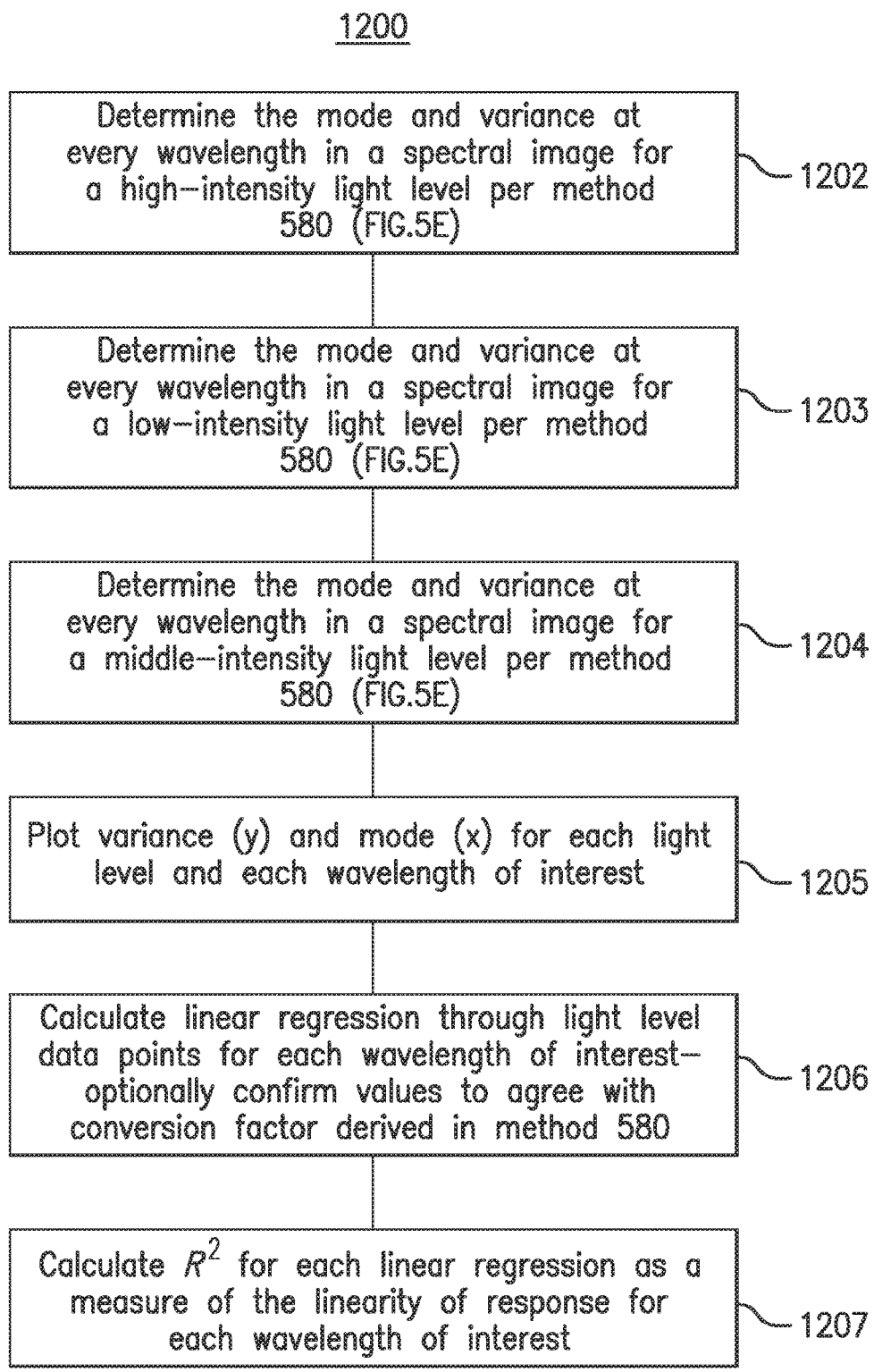
FIG. 6A is a flow chart illustrating method 1200 for determining the linear response of the spectral imaging apparatus to linear increases in illumination

In calibrating the system, the linearity of the sensor response may also be determined. Shown in FIG. 6A is a method 1200 for determining the linearity of the system 500, or components thereof (e.g., the linearity of the response of the imaging apparatus acquisition apparatus 502, such as a digital camera, spectral camera, or the camera's sensors to spectrum (e.g., light)). The linearity is determined to ascertain whether the signal output from, for example, the imaging acquisition apparatus 502 is proportional to the amount of spectrum (e.g., light) received. In an exemplary embodiment of the present invention, the imaging acquisition apparatus 502 is a digital or spectral camera having charge-coupled device (CCD) sensors. One of the functions of the CCD sensors is to convert photons carrying image information (i.e., an analog signal) into an electronic signal (i.e., digital signal). Ideally, the signal output from the imaging apparatus and/or components thereof should be linearly proportional to the amount of light incident on the sensors. In an exemplary embodiment of the present invention, the amount of light incident on the sensors is relative to an amount of exposure time to spectrum (e.g., light).

Figure 6B:
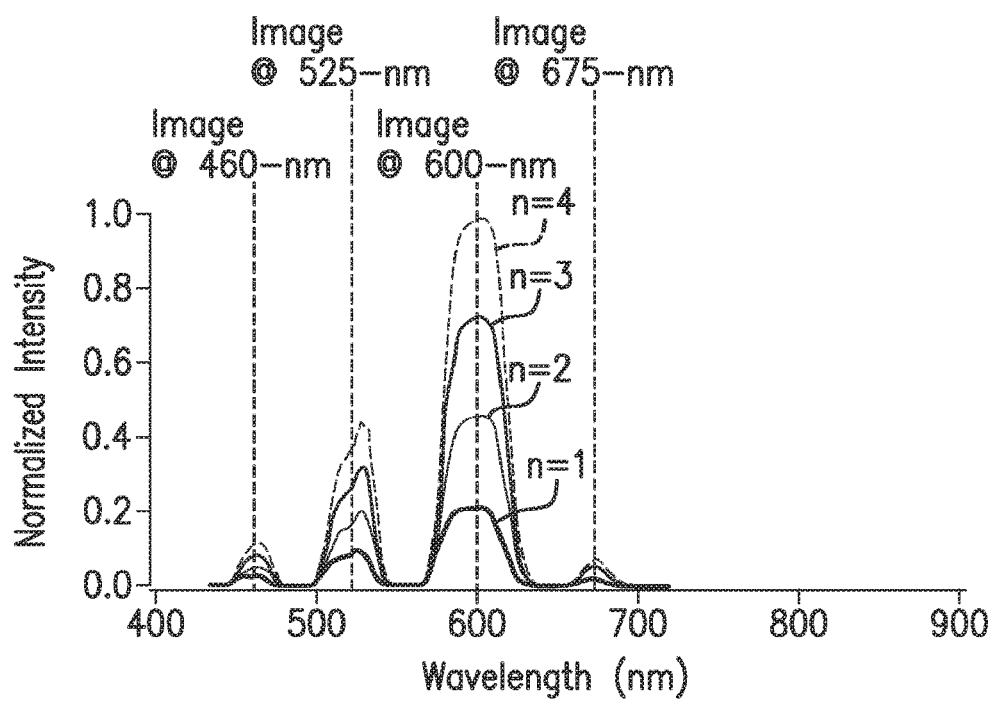
FIG. 6B is a plot representing spatially averaged spectral data imaged of a calibration illumination source acquired at 4 light levels

FIG. 6A illustrates the method 1200 for determining the linearity of an imaging apparatus and/or components thereof (e.g., a spectral camera and/or the camera's sensors). In an exemplary embodiment of the present invention, each image is acquired using a pre-determined exposure time (e.g., 20 ms) at multiple wavelengths (as shown in FIG. 6B, n=4) and pre-determined light levels appropriately distributed across a large part of the dynamic range of the system 500 (e.g. at 10 mW, 40 mW, 70 mW, 100 mW) to obtain spectral data cubes corresponding to different levels of incident light, as shown in FIG. 6B. The spectral data is, generally, obtained at wavelength chosen to mimic wavelengths of fluorescence of chosen markers. In FIG. 6A, step 1202, a a first set of image data is captured using method 600 of an uniformly illuminated field (e.g., a substrate, such as a slide that is partially reflective) and a mode and variance of the pixel intensity values of the first set of image data is determined. The light level captured by the imaging acquisition apparatus 502 should be set at or near the maximum of the dynamic range of the sensor at a set exposure time. In step 1203, a second image and/or a second set of image data is captured of an object (e.g., a substrate, such as a slide that is partially reflective) at or near the minimum of the dynamic range and a mean and variance of the pixel intensity values of the second image and or second set of image data is determined. In step 1204, a third image and/or a third set of image data is captured of an object (e.g., a substrate, such as a slide that is partially reflective), by the imaging acquisition apparatus 502, somewhere in between the minimum and maximum of the dynamic range and a mode and variance of the pixel intensity values of the third image and or third set of image data is determined. In step 1205, the variance value is plotted on the abscissa and the mode value is plotted on the ordinate of a graph for each of the three (or optionally more) points. The slope of a straight line fitted to the points represents the conversion value and should ideally be in agreement with the value calculated in method 580 (at the given wavelength being evaluated). The measure of 'goodness of fit' for a straight line to the data points is a measure of the sensor's linearity of response (at this given wavelength).

In step 1207, the linear regression is determined for each of the sets of mean and variance data associated with the first, second, and third images and/or set of data at a given wavelength. In an exemplary, embodiment of the present invention, the mean and variance data associated with the first, second, and third images and/or set of data may be plotted on a graph. In an exemplary embodiment of the present invention, the linear regression may be determined via a least-squares calculation:

$$\text{Min}Q(variance_{noise}, \text{slope}) = \sum_{i=1}^{n} (variance_i - variance_{noise} - slope_i)^2$$

Where i represents a given light level, $variance_{noise}$ represents the variance calculated for offset images (no light), and the $slope_i$ represents the slope at the variance/mode datapoint for a given light level. The equation above yields the slope for a line originating at the value of variance calculated for offset images (no light):

$$variance_{estimate} = slope * mode_i + variance_{noise}$$

In step 1207, the $R^2$ value is determined or identified:

$$SS_{err} = \sum_i (variance_i - variance_{predicted})^2$$

$$SS_{total} = \sum_i (variance_i - variance_{mean\ of\ all\ values})^2$$

$$R^2 = 1 - \frac{SS_{err}}{SS_{total}}$$

Where $variance_{predicted}$ is the variance value predicted by the line equation at a given light level and $variances_{mean\ of\ all\ values}$ is the mean value for the variance values gathered at different light levels. $SS_{err}$ represents the 'residual sum of squares' and $SS_{total}$ represents the 'total sum of squares' to evaluate the 'goodness of fit' for the datapoints to the line calculated through the datapoints.

Figure 6C:
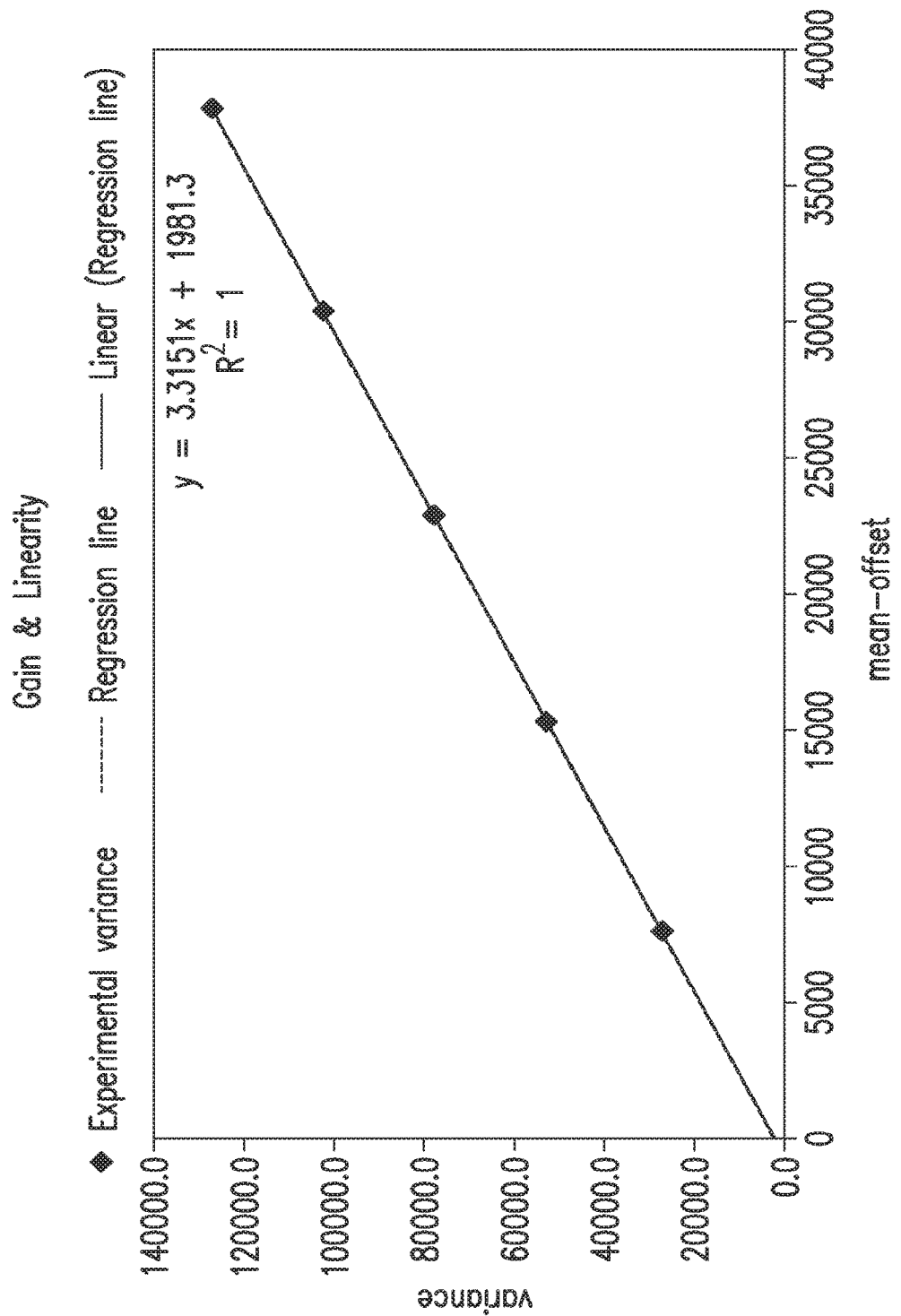
FIG. 6C is a graph representing gain and linearity characteristics of the MSI system determined at a single spectral wavelength from a dataset according to the embodiment of the method of FIG. 6.

The $R^2$ value is indicative of the linearity of the image acquisition apparatus 502, or component thereof (e.g., the sensors of a spectral camera). For example, if the $R^2$ value is equal to one (1), then the system may be regarded as highly linear and ideal for quantitation. In step 1206, a slope is determined from the equation of a line fit to the mean and variance data associated with each of the first, second, and third images and/or data sets. Ideally, the slope of this fitted line will not vary greatly wavelength to wavelength. Steps 1204 through 1222 is repeated for various wavelengths/bandwidths in the dataset. FIG. 6C shows the mean intensity vs. variance dependence of a nearly perfect linearity, assessed using the embodiment 600. The value of standardized intensity unit per unit grey level, is determined from the slope to be about 3.3 e for the wavelength $\lambda_k$. A linear regression fitting curve through the acquired points of the dependence yields $R^2$ value for the chosen wavelength $\lambda_k$. The $R^2$ value reflect a degree of linearity of the MSI system's (spectrometer's) response, with $R^2=1$ indicating ideal linearity.

The determination of the imaging system's standard unit conversion, dynamic range, and linearity of its performance provides calibration foundation for interpreting acquired image intensity information in terms of standardized units of $e^-$, the range of detectable values that the instrument is capable of recording, and the relationship between intensity values and the intensity of the sample. The use of these basic metrics for spectral imaging instruments permits meaningful comparisons of the intensity data obtained with different instruments.

Spectral Accuracy and Resolution

According to an embodiment of the invention, the evaluation of the ability of the system to resolve spectral features of an acquired image should be established prior to the use of spectral unmixing algorithms. The method for such evaluation uses a long-wavelength pass filter with a predetermined cut-off (for example a filter with a cut-off at about 409-nm for collection of light between about 409 nm and 900 nm). Preferably, the determination of spectral accuracy and resolution is carried out with the use of a temperature-controlled source of light, because the temperature variations may affect the spectral positions of elemental spectral lines.

Figure 7A:
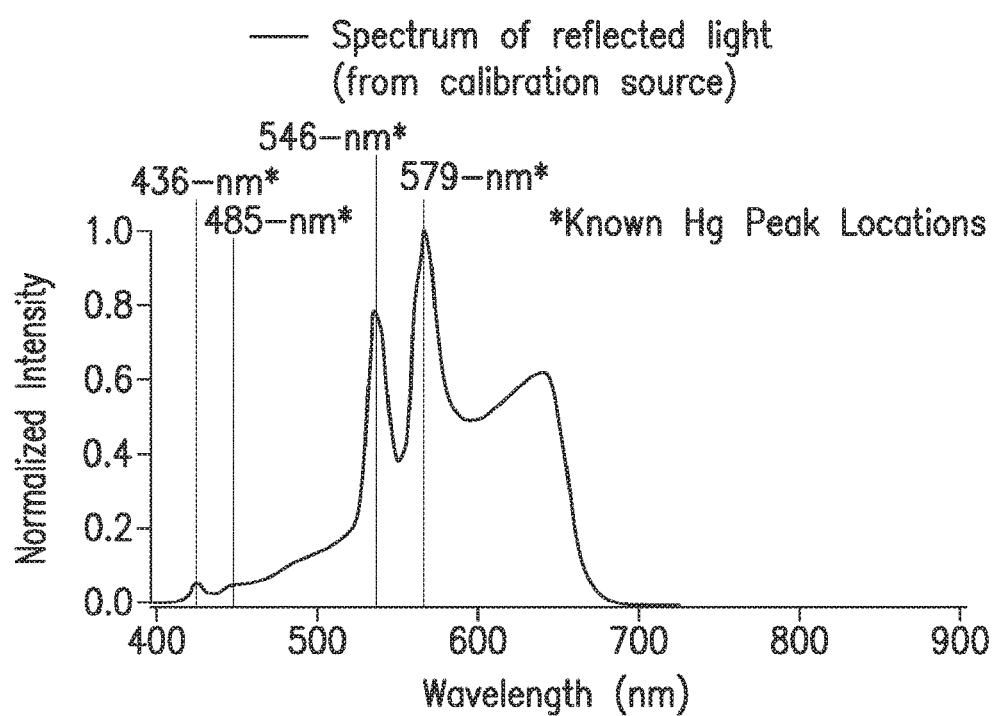
FIG. 7A is a spectral distribution of intensity of light generated by the calibrated light emitter of the source of light of FIG. 4A illustrating the location of Hg elemental peaks in the spectra.

A spectral data set (a multispectral image cube similar to that of FIG. 1A) is acquired using standardized exposure time and levels of illumination at high (spectral) resolution settings of the imaging spectrometer using illumination distributed to evenly cover the area captured by, for example, a 2D camera array. Such illumination may be provided from a closed-loop stabilized Hg metal-halide lamp, in reflection from the chosen surface (for example, with the use of a setup similar to that of FIG. 4A). An example of the acquired spectrum from such an Hg-doped, metal-halide lamp technology is shown in FIG. 7A. Spectral positions of the elemental spectral peaks of the Hg-lamp are known (436 nm, 546 nm, and 578 nm).

Figure 7B:
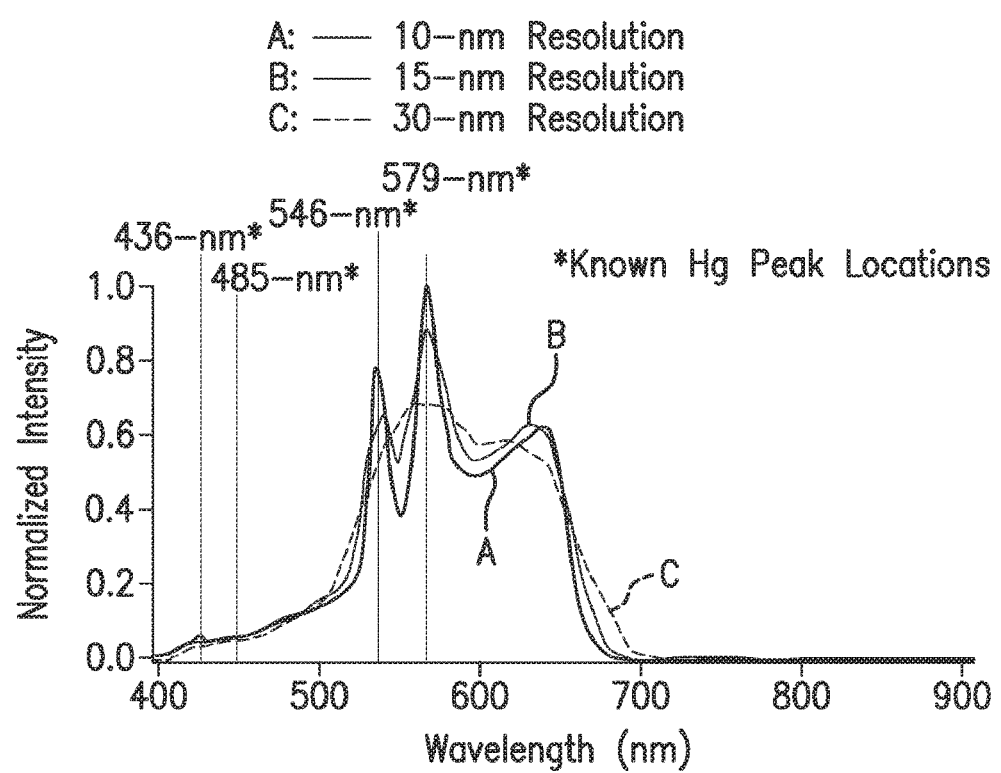
FIG. 7B is a graph showing traces of the normalized spectral distribution of FIG. 7A acquired with different spectral resolution.
Figure 7C:
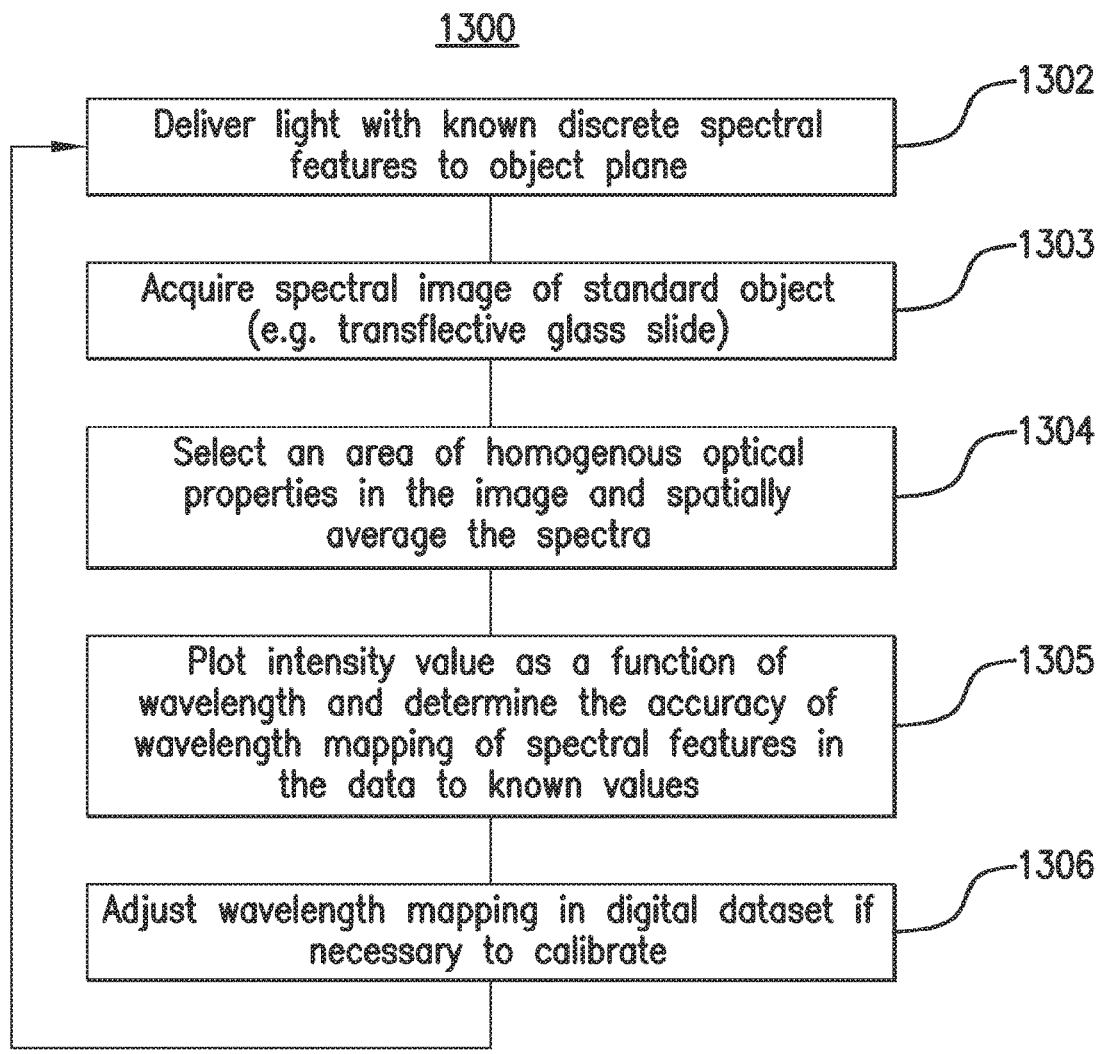
FIG. 7C is a method, in accordance with an embodiment of the present invention, for characterizing the spectral features of an image or image data to a known set of spectral features associated with an object.

In accordance with a method 1300 of the present invention, shown in FIG. 7C, the spectral features of an image data set are compared to an expected set of spectral features for an image data set of a known object, for example a partially reflective slide. This method of characterization employs spectral peaks of a known standard to determine if the imaging spectrometer recognizes or detects the peak locations at the wavelengths known to correspond to these elemental spectral peaks. Because the used elemental spectral peaks are known to be very narrow (due to the elemental luminescence properties) and, therefore, can be considered approximately spectrally distinct or discreet, the peaks can be used to determine the ability of the measurement equipment to resolve closely spaced peaks based on a chosen resolution criteria. (Such determination is based on the assumption that standards such as elemental peaks have much narrower spectral features than the resolution of the used spectrometer.) Therefore it can be deduced that the peak shape produced by the imaging spectrometer represents the limits of the spectrometer resolving power under the conditions of the test.

In step 1302, a spectrum source with known spectral features is activated, for example, a light source, and spectrum is output (e.g., illumination). In step 1303, an image is acquired of the object. In step 1304, we average the spectral information (trace), for areas known to be homogenous in spectral properties in order to minimize the impact of noise on the spectra measured. In step 1305, the location of the spectral peaks is identified and/or measured from a plot of intensity as a function of wavelength, and compared to known values of where those peaks should occur based on knowledge of the spectral features, (for instance elemental properties of the illumination standard). If the peaks are offset from the expected locations, then the instrument may need adjustment or service, for example, by adjusting the hardware and/or software associated with the system 500. In an exemplary embodiment of the present invention, adjustment of the system 500, in response to the offset spectral peaks, involves adjustment of wavelength mapping to recorded intensity values by altering constants used in the spectral image processing and analysis software.

In reference to FIG. 7B, the location of each spectral peak can be described as the wavelength value half-way between rising and falling intensity values at half of maximum above baseline; this convention for determination of a spectral peak location is used to reduce potential for misstating the peak location due to aliasing error introduced by the location of spectral intensity sample points across the spectral capture range.

Figure 7D:
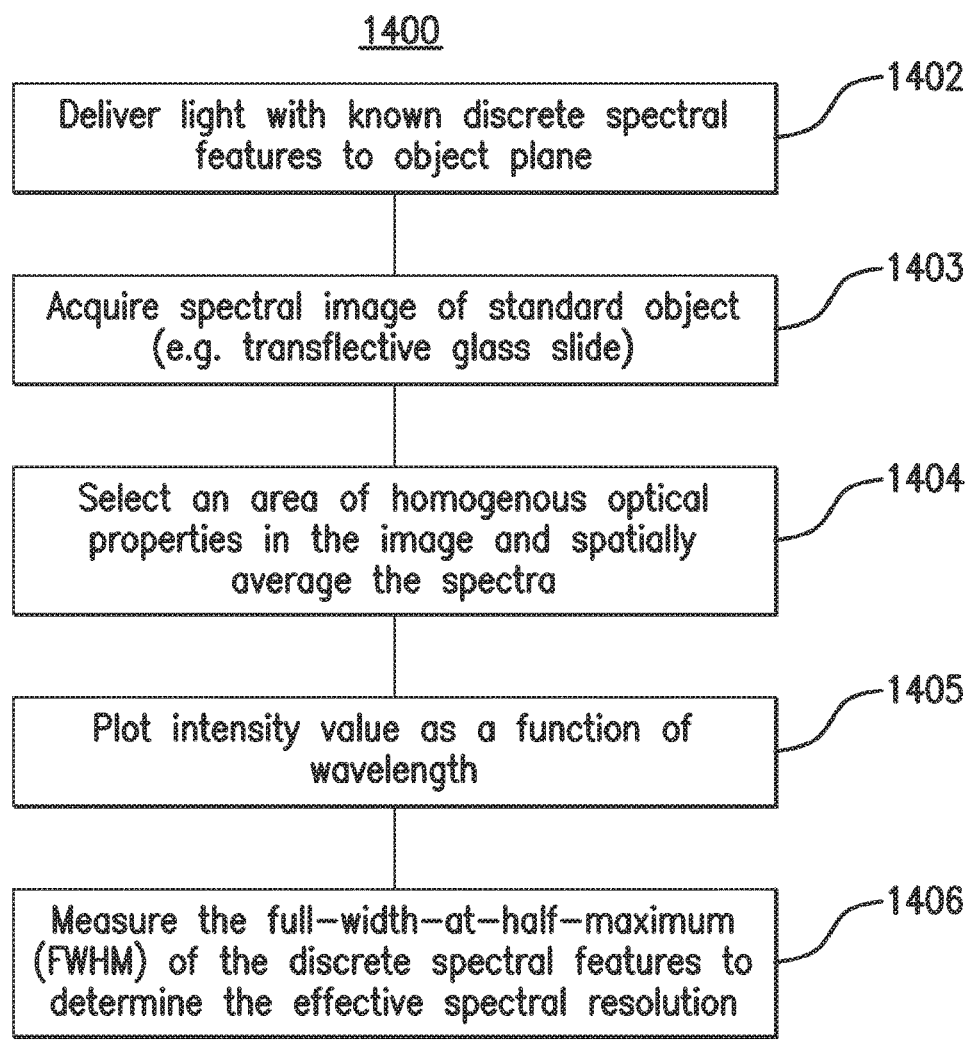
FIG. 7D is a method 1400 for verifying spectral resolution, in accordance with an embodiment of the present invention.

In an exemplary embodiment of the present invention, the resultant spectral data (recorded intensity as a function of wavelength) is identified, via, for example a plot, and the width of the spectral peaks is identified and/or measured via the plot. In an exemplary embodiment the measurement is taken approximately halfway between the baseline of the peak and the top of each peak. Typically the spectral features of the chosen calibration standard (e.g. Hg elemental peaks) are much narrower that the limited resolution of the spectral imaging device. Accordingly, the recorded width of the spectral peaks is identified, and such width corresponds to the spectral resolution for a particular part of the wavelength range. Shown in FIG. 7D is a method 1400 for verifying spectral resolution at each wavelength is according to specification for particular instrument. In step 1402, a spectrum source with discrete features or narrow peaks is activated (for example, a light source with elemental peaks), and spectrum is output onto an object (e.g., a transflective slide). FIG. 7B depicts the spectra acquired with three resolution settings, plotted and measured using the steps 1404-1406 of method 1400. Since the Full Width at Half Maximum (FWHM) of at least some of the spectral peaks of the used calibrated source of spectrum (an Hg-lamp in this case) is known to be narrower than the resolution of the instrument, the acquired spectra are indicative of how the resolution setting compares with the known FWHM of the peaks. For example, the corresponding FWHM values for peaks centered at about 546 nm and 578 nm of can be considered.).

Referring further to FIG. 7B, in a 30 nm resolution spectrum (trace C), the Hg-lamp spectral peaks at 546-nm and 578-nm are not resolved, and the peak intensities are averaged. In a 15 nm resolution spectrum (trace B), the peaks are resolved but defined rather bluntly. In a 10 nm resolution spectrum (trace A), the peaks are well resolved and the relative contribution of each of the peak to the overall spectrum is more easily discerned through direct inspection of the spectra. This example illustrates the impact that spectral resolution settings can have on the representation of a sample in the data, and spectral resolution requirements may be measured and specified for instrumentation using this method.

Figure 8A:
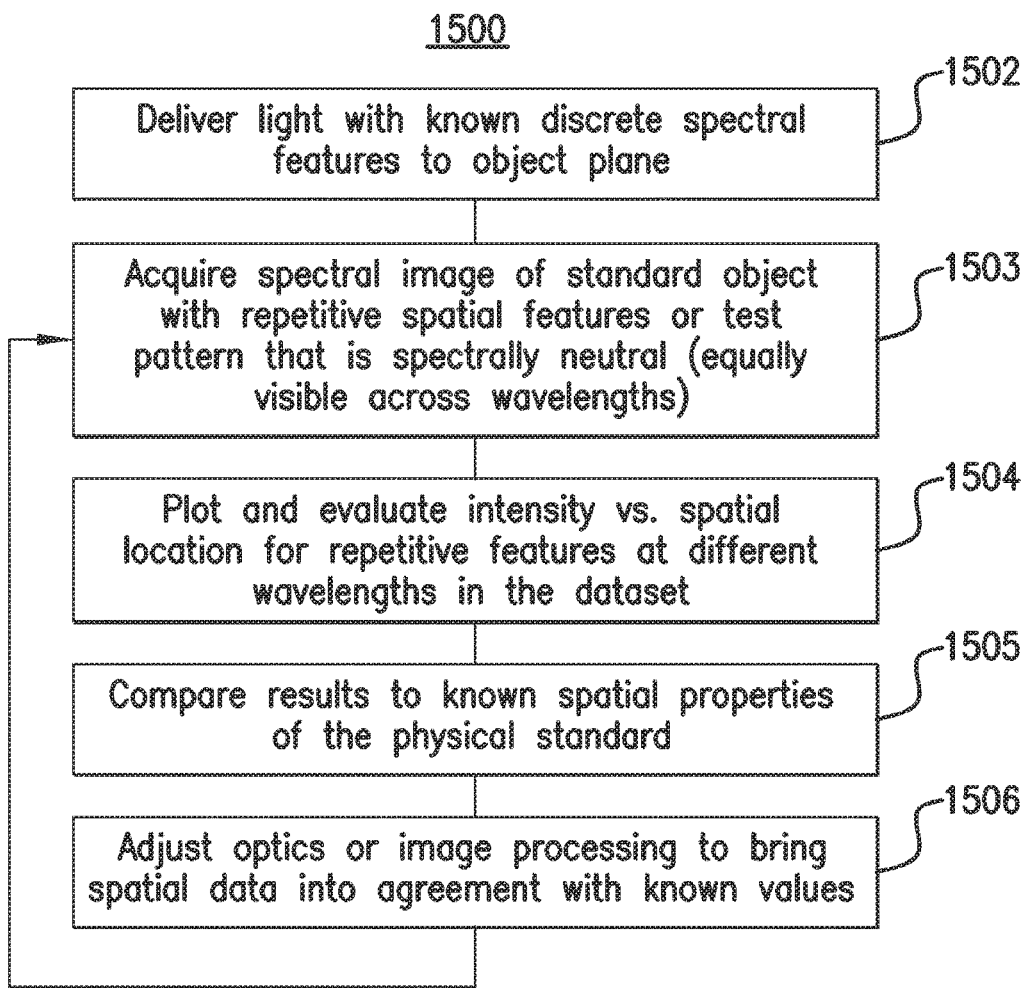
FIG. 8A is a method 1500 utilized to assess spectral-spatial coordinate accuracy, in accordance with an embodiment of the present invention.

Spatial Accuracy and Precision/Lateral and Axial Chromatic Aberrations Testing of Optics Shown in FIG. 8A is a method 1500 utilized to assess imaging of spatial coordinates, for example, location, and focus quality, of spectral images taken across a large spectral range. In step 1502, a spectrum source is activated and spectrum is output to an object, for example a slide with sort of geometric grid (such as a calibration slide having a regular repeating pattern). In an exemplary embodiment of the present invention, the spectrum source is a broadband spectrum source, or any source that generates illumination at wavelengths covering the spectral detection range. According to an embodiment of the invention, the spatial accuracy and precision of the image acquisition system 502, for example, a spectral microscope or slide digitization instrument, is evaluated using a precision standard judiciously designed for this purpose. For example, a reflective pattern standard can be used providing that the test pattern is equally visible at all wavelengths that are important to a given application (such as multiplex tissue imaging applications). The standard is adapted to produce a set of regular image features revealing lateral distortions and focal shifts that the imaging system may introduce at different wavelengths. In step 1503, the image acquisition device 502 is utilized to acquire an image and/or image data (e.g., a spectral image and/or spectral image data) of the slide or object. In step 1504, intensity data from one or more rows or selections of pixels is identified for each single wavelength or bandwidth in the dataset. In an exemplary embodiment of the present invention, the intensity from a single row or column of pixels across an image, at a single wavelength, e.g., blue, is plotted as a function of spatial position, next another wavelength e.g. green is plotted on the same graph. This process continues until all of the wavelengths of interest are plotted for comparison. Step 1504 may be repeated for a plurality of spatial regions. Periodic spatial features imaged across a field of view at one wavelength may be compared to the same periodic features at another wavelength. Alternatively, the periodic changes may be compared to the expected performance of the object (e.g., tolerances of the calibration slide). Alternatively, pixel intensities at a plurality of wavelengths may be iteratively evaluated in the axial (z) axis by taking an average intensity value at a given illumination wavelength, adjusting the physical focus of the instrument, and re-evaluating average intensity values at multiple focal positions. This procedure may be used to determine if there are axial chromatic focal shifts that occur at different wavelengths by finding the focal position of highest intensity value for a given wavelength (indicating the focus for the given wavelength and differences in the focal position between wavelengths).

Figure 8B:
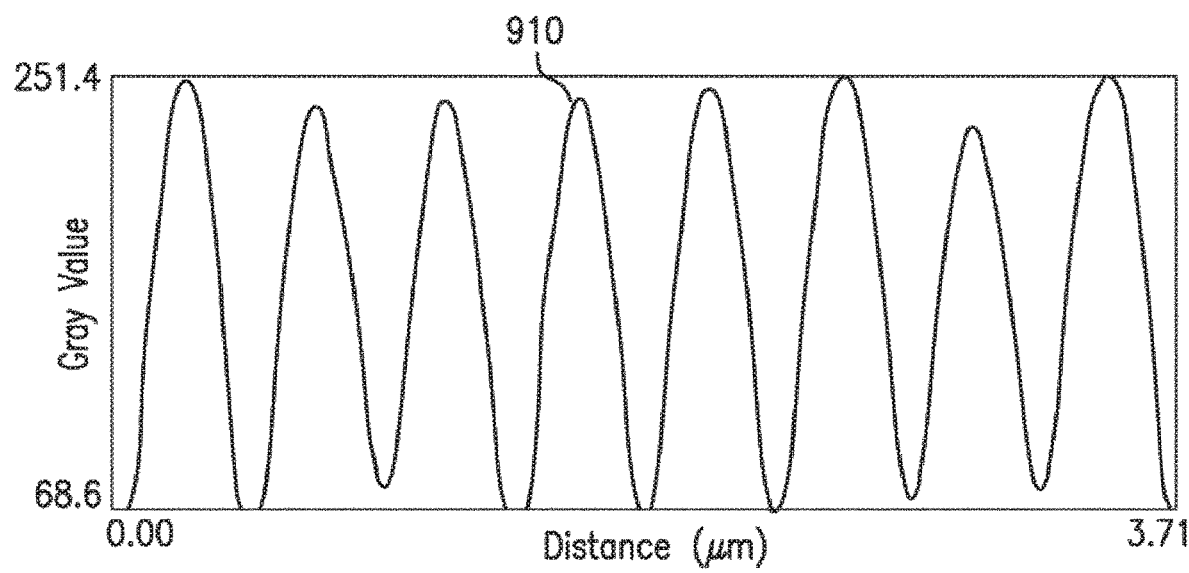
FIGS. 8B and 8C show the respective intensity profile and image of a sample precision standard used with an embodiment of the invention to determine spatial accuracy and precision of imaging provided by a MSI system.
Figure 8C:
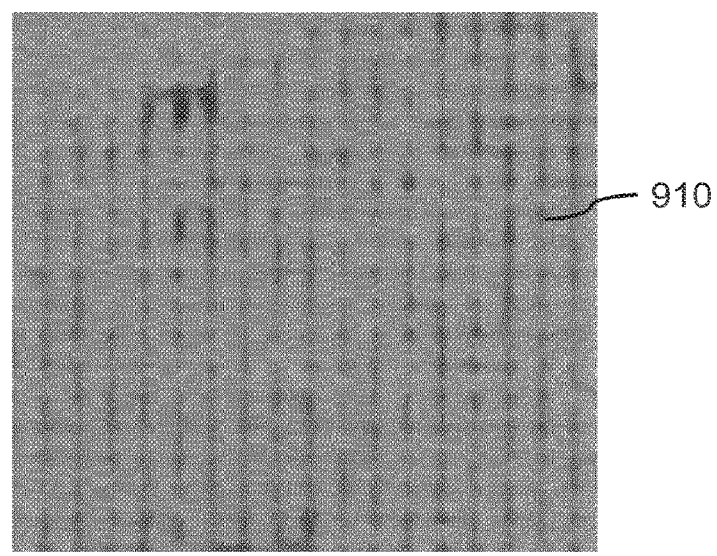

FIG. 8B is a one-dimensional (1D) plot 906 of a distribution of intensity vs. position across the reflective standard 910 of FIG. 8B, acquired at $\lambda_3$. In the examples of FIGS. 8B, 8C the reflective standard 910 was a carbon film replica standard conventionally used in electron microscopy. The intensity values corresponding to edges of the periodic features of the reflective pattern produced by the standard 910 are representative of the lateral spatial resolution of the imaging system for in-focus features at a single wavelength from a spectral dataset.

If the reflective standard 910 is placed with a deviation from the "ideal" focus of the optical system 436, the resulting image of such standard has decreased image contrast (as acquired from the plot 906) and the spatial resolution of the imaging system determined in reliance on such image contrast according to a defined criterion (for example, a rate of intensity change) will be erroneous. The percent deviation of the positioning of the reflective standard 910 from the ideal focus at other wavelengths can be approximated by percent reduction in resolution at the edges of the periodic features of the reflective standard pattern as compared to the spatial resolution determined at the chosen reference wavelength, for example $\lambda_3$. The lateral resolution of the MSI system (in this example, the spectrometer or spectral cameral) is further determined by measuring the relative positions of a half-maximum point at the curve and the maximum intensity point at the curve and comparing the wavelengths corresponding to these points. Descriptive metrics, such as the spatial regularity of image fringes in the plot 906 across the field-of-view can be determined with appropriate image data processing.

Distortions (such as lateral chromatic distortions, for example) within the imaging field can also be determined. A pseudo-color overlay of the wavelength-band images of a spatial calibration pattern should reveal good alignment for all the wavelength components and the spacing between regular features should be consistent across the field. Such spatial/spectral evaluations are necessary to characterize and optimize the wavelength-dependent performance of an imaging system for assay applications. For instance, if it becomes clear that there are lateral spatial distortions at some wavelengths, the root cause can be identified and corrective measures implemented if necessary. If the distortion situation is not analyzed and/or characterized, the spatial localization results for diagnostic applications may be different for different wavelengths recorded in a spectroscopic image and this would be a source of possible error or misinterpretation of molecular-marker localization.

Quantum Efficiency, a Wavelength-Dependent Response

The quantum efficiency (QE) of the image acquisition apparatus 502 (e.g., a photosensitive device, charge-coupled device (CCD) or spectral camera) may also be determined. Relative quantum efficiency measures the image acquisition apparatus's 502 sensitivity to light at different wavelengths. Quantum efficiency refers to the amount of incident photons that are converted to electrons and may be represented by a ratio (e.g., the IPCE ratio). The IPCE ratio correlates to the percentage of photons hitting the photoreactive surface of the image acquisition device 502 that produces charge carriers. The IPCE ratio, correlating to quantum efficiency, is measured in electrons per photon or amps per watt. Quantum efficiency may be measured over a range of different wavelengths to characterize the image acquisition apparatus's 502 relative efficiency at each wavelength. In an exemplary embodiment of the present invention, we determine the quantum efficiency to calibrate for the proportion of photons that actually record (i.e., be sensed), out of all the photons delivered to the apparatus at different detection wavelengths. Thus, a user may make corrections to the data based on the quantum efficiency so that differences between instruments or sensors can be reconciled. In one embodiment, adjustments may be made by computational scaling of intensity values in a spectral cube to correct for differences of QE using different optics. In another embodiment, the exposure time for capture of different wavelength ranges can be changed to compensate for differences in QE. In another embodiment, the QE information can be used to increase or decrease the illumination level to compensate for differences in QE.

To determine a wavelength-dependent response of the imaging system 500, according to an embodiment of the invention several illumination (emission) filters are selected, for example, filters that have substantially equal bandwidths corresponding to, for example, a stain or label, such as dye analyte (e.g. DAPI) and/or quantum dot emission wavelengths (for example, a filter with a pass band of about 20 nm centered at about 460 nm, which is denoted, for simplicity, as 20/460; or a 20/525 filter; or a 20/565 filter, or at least one of 20/585, 20/605, 20/625, 20/655, 20/710 filters). The emission filter(s) having, for example, equal or substantially equal bandwidths to cover the entire wavelength range of the system 500, are individually placed in the imaging path shown in FIG. 4A. A power meter or sensor positioned at the object plane, for example, a surface of the object/sample is used to calibrate the spectrum source (e.g., a light source), such that the spectrum out may be standardized to output a standardized amount illumination at each wavelength or band being measured. As a result, the amount and/or power of spectrum (e.g., light) may be delivered to or within the system 500, or components thereof, and such amount and/or power of spectrum may be reproduced or substantially reproduced at a surface of the object and/or sample plane to ensure that an equal amount of light is gathered by the imaging optics and guided to the sensor at each wavelength band of interest A partially reflective sample (for example, a glass slide 436 as discussed in reference to FIGS. 4A, 4B) may be used to provide a reflective surface, alternatively a transmitted spectrum source 530 (e.g., light source) may be used as long as the output can be carefully adjusted and any reflective surface is equally reflective for all the wavelengths of interest. The image acquisition apparatus 502 (e.g., spectral camera, spectrometer, etc.) is used, for example, with standardized spectral resolution setting (e.g., 5 nm) and with standardized exposure time (e.g., 30 ms) during the acquisition of all of the quantum efficiency images. Generally, the standardized exposure time is determined to reach approximately 80% of the saturation level of the detector receiving light from the filtered band which has the greatest efficiency of detection. As with all data acquired and analyzed, the images are bias corrected and the mean value is determined for each peak wavelength image.

Figure 9A:
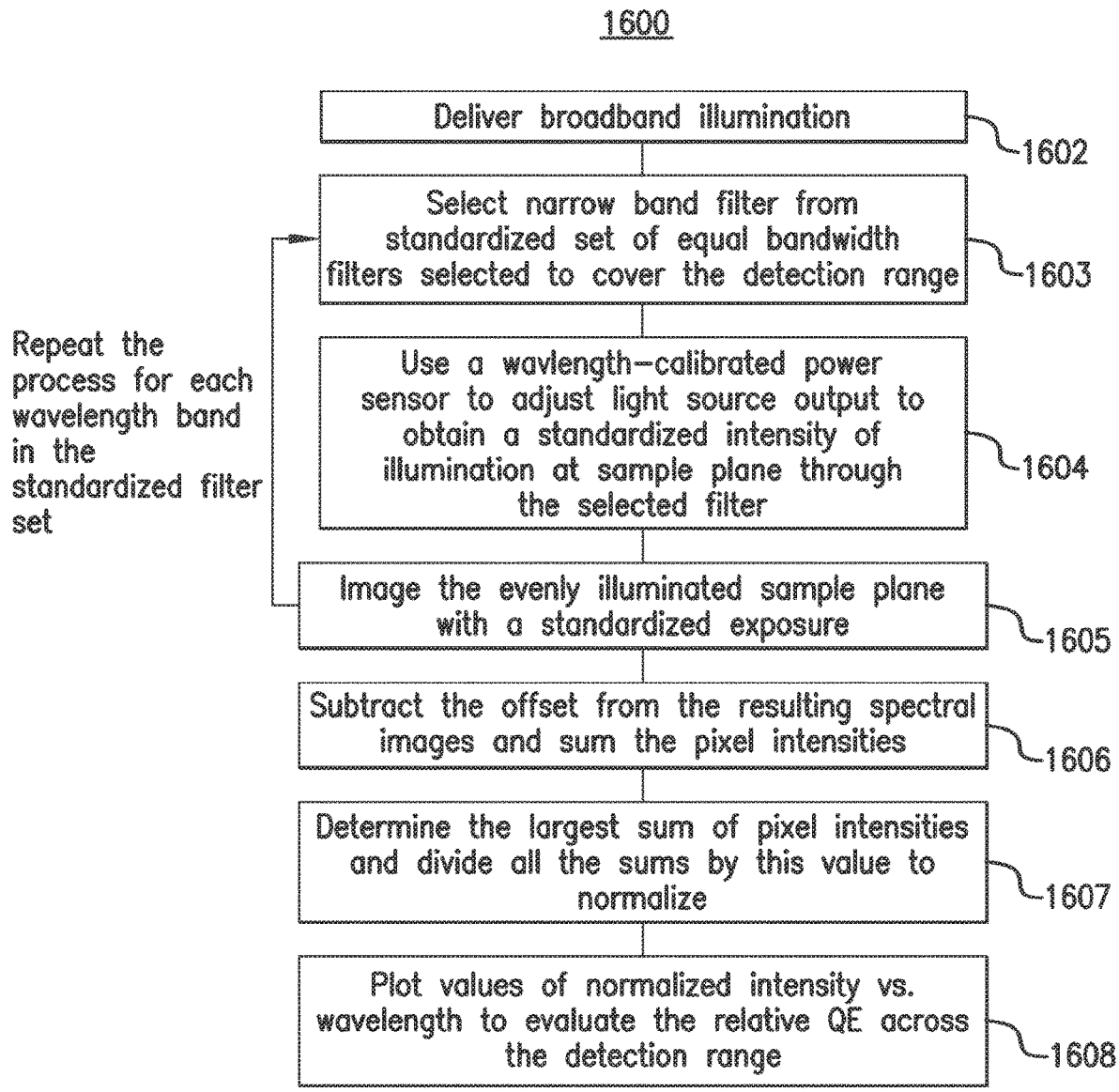
FIG. 9A is an exemplary method of determining the quantum efficiency of spectral detection, in accordance with the present invention.

Shown in FIG. 9A is an exemplary method 1600 of determining the quantum efficiency. In step 1602, the spectrum source 522 (e.g., a broadband light source) is activated and spectrum (e.g., illumination) is output, and is measurable by a standardized unit (e.g., watts). In step 1603, a narrow band filter from a standardized set of equal bandwidth filters covering the detection wavelength range of the instrument is selected. In step 1604 the power is measured after light passes through the selected filter and the light source is adjusted to provide a standardized level of light to the object plane. In step 1605, an evenly illuminated sample plane is imaged by the spectral imaging device. In step 1606, the spectral image is corrected by subtracting the offset and the pixel intensities for the entire image are summed to measure the total amount of light collected in the spectral image. In step 1607, after all the spectral images have been collected (one for each filter), each pixel-intensity-sum value is divided by the largest sum to normalize all the sums to a decimal fraction of the largest value. The largest sum value represents the wavelength of highest quantum efficiency, and the other values are some fraction of the highest quantum efficiency. In step 1608, these values may be plotted to visualize the quantum efficiency curve across the wavelength range. Alternatively, the values can be used to generate a calibration curve used to adjust spectral images to negate the different QE of the imaging system at different wavelengths. In an exemplary embodiment of the present invention, the relative quantum efficiency data generated is utilized to correct recorded intensity values for different wavelengths acquired with given settings. In an exemplary embodiment of the present invention, a quantum efficiency curve is generated and an uncorrected dataset is divided by the quantum efficiency curve to adjust recorded intensity values for differences in relative detection efficiency at different wavelengths. This process corrects the numerical intensity values at each wavelength. In an exemplary embodiment of the present invention, such corrected data is utilized to compare data acquired using different lens systems, which have different wavelength dependent transmission properties. In this manner, the imaging system is used to measure known amounts of spectrum, for example, light at different wavelengths/bands, to determine the relative percent efficiency of detection at different wavelengths across the spectrum. Such measurement produces a system-level wavelength dependent efficiency measurement that includes both the optics transmission and sensor quantum efficiency. For instance, a system may have peak efficiency of detection at wavelength 500-nm, with 30% of peak efficiency at wavelength 400-nm and 30% efficiency at wavelength 600-nm. If these values of detection efficiency are known, then the measurement of analyte intensities taken at different wavelengths (e.g. intensity of light of quantum dot 565 and that of and quantum dot 655) can be corrected to take this different efficiency of detection due to the instrument into consideration. This characterization method permits calibration to enable comparison of measurements taken at different wavelengths and for datasets taken using different components with different transmission efficiencies.

The percentage difference in values measured at different wavelengths can be compared between instruments or between optical configurations to provide a comparison of instrument response to wavelength, given standardized input (large disparities in wavelength response should become apparent between devices using this approach). The ability to correct for differences in quantum efficiency at different wavelengths permits accurate interpretation of samples without the potential for misinterpretation of analyte concentration due to the wavelength efficiency of a given instrument.

Calibration of an MSI according to embodiments of methods and algorithms of the invention described ensures accurate imaging results in substantial operational isolation and decoupling of the performance of the imaging instrument from variability of fluorescent samples and yet still provides an integrated system level performance. According to these embodiments, a calibrated light source and durable physical standards can be built in the imaging system and combined with software tools to permit routine and, optionally, automated, check and self-calibration procedures and troubleshooting procedures to be performed.

Once an MSI and optical acquisition system has been calibrated according to the methods described above (or to other related methods), it becomes possible for the user of such imaging system to test computer program products used in conjunction with the MSI acquisition (such as, for example, the algorithms embodying the spectral unmixing data processing and algorithms related to data normalization choices such as, for example, peak normalization, vector normalization, area normalization) that increase fidelity of the data processing. At least for the same reason, the MSI system calibrated independently from a fluorescent standard is configured to permit a sample-independent verification of whether the unmixed spectral data correctly represents the contributions of multiple fluorescent species. Indeed, by first validating the instrumental performance and calibration, the user can isolate and identify other sources of errors that may be related to sample preparation and/or the software processing algorithms. If the data processing algorithms have been calibrated and/or verified independently from a particular fluorescent standard and shown to deliver physically accurate results, then the deviation of the results of spectral unmixing of multispectral images from what is physically accurate is indicative of changes of or deviations in operational performance of the MSI system itself.

Embodiments of methods permitting such sample-independent imaging data verification are further discussed below.

Verification of a Quantitative Multiplex Spectral-Unmixing

For a fluorophore standard such as a wet mount of fluorescent dye in known concentration, or fluorescent polystyrene beads, the relative signal contribution of an analyte depends on the relative output of the spectrum source, for example, a light source, at different wavelengths and the optical properties of the image forming apparatus 508 and/or image acquisition apparatus 502, (e.g., microscope); however, this is not widely appreciated. For this reason, a fluorophore standard validated using one instrument may be completely useless as a reference on a different instrument. Moreover, fluorophore standards are not useful for spectral instrument calibration when other reporters, such as quantum dots, are used because the excitation wavelengths and filters used are completely different. In the novel method described here, the impact of sample properties is almost non-existent, and the instrument is measured against reproducible illumination. Instruments that are equipped to identical standards will be expected to perform equivalently, and the impact of changing different components on the expected outcome can be measured.

According to an embodiment of the invention, the verification of methods of spectral unmixing generally makes use of a dual-beam spectrum source and/or illumination geometry (e.g., spectrum sources 522 and 530, as shown in FIG. 5A) configured to deliver spectrum (e.g., illumination) at multiple wavelengths/bands (having various intensity peaks at multiple wavelengths). In an exemplary embodiment of the present invention, a spectrally-selective system 528, for example, as shown in as shown in FIG. 5A, may be placed in the path of spectrum output from each of the spectrum sources 522 and 530. In an exemplary embodiment of the present invention, each spectrally-selective system 528 has different band pass specifications. As a result, two beams of light are generated, with each having its own spectral features, for example, their own distinct spectral features, (such as, wavelength, intensity, etc.).

The two beams mix at, a plane or surface, for example, the object plane 524, where the imaging acquisition apparatus 502 is focused. The object plane 524 corresponds to a plane of a substrate, material, or substance, for example, a clean glass slide, or a stage, for example, a microscope stage. In exemplary embodiments of the present invention, the glass slide is partially reflective and partially transmissive. Thus, part of the incident beam is reflected from the partially reflective surface of the glass slide, and part of the transmitted beam passes through the glass slide and is mixed with the reflected portion of the light. By carefully controlling and standardizing the amount of input light, the two sets of spectral features can be controlled and held to a precise specification.

The relative contributions from the different peaks (i.e., the peaks of the light signal reflected from the sample plane and the peaks of the spectrum signal (e.g., light signal) of the transmitted spectrum (e.g., light)) can be modulated, and thus, the two sets of peaks can be convolved/mixed to test an imaging system and/or instrument's, for example, ability to unmix overlapping spectra. Because each of the two spectrum sources and their output amounts, intensities, and/or wavelengths (e.g., light sources) can be controlled independently, the relative peak contributions to the convolved signal can be unambiguously determined or predetermined before the spectra from the two spectrum sources are mixed.

Also, because each of the two spectrum sources (e.g., light sources) can be controlled independently, the contributing integrated intensity of peaks attributed to particular bandwidths may be attenuated and/or increased and/or decreased to test the unmixing in the context of the entire dynamic range of the imaging system 500 and/or image acquisition apparatus 502, or components thereof (e.g., sensors, detectors, or detection system). Because of the controlled specifications of the spectrum (e.g., illumination) and sensor systems, differences in the unmixing results (i.e., between the expected contributions of spectra from the spectrum sources and the unmixing results from an imaging system's unmixing algorithms) may be indicative of a change to one or more properties of the MSI system or components thereof. The tolerances for instrument performance are thus isolated from samples (e.g., biological specimens and/or tissue slides), and any instrument tolerances may be adjusted to a well-defined specification An example of such system has been shown in FIG. 4A. Generally, the two incident beams 426, 446 overlap at the site of an object, for example, a sample plane provided, for example, by the clean transflective glass slide 430. The relative levels of illumination (for example, irradiance) provided by these beams can generally be varied instrumentally, and thus the spectra of the beams 426, 446 can be mixed to test the ability of the system 500, or component thereof, for example, the image acquisition system 502, to unmix these overlapping spectra across the entire dynamic range of an optical detector (already calibrated according to one or more of embodiments of the invention discussed in reference to FIGS. 5-9). Because each of the two sources of spectrum, for example, light sources (the source 410 and the source of light 448) can be controlled independently, the relative contributions of the beams 426, 446 to the signal, for example, optical signal, received by the image acquisition system can also be unambiguously determined before the spectra of the beams 426, 446 are mixed.

Because the illumination geometry of an embodiment ensures even field illumination, the detection response across the entire aperture of the detector (e.g. image acquisition apparatus 502, or sensors thereof) can be verified and deviation of responses from different pixels of the detector, or from the image acquisition device's expected performance or performance specifications may be determined. In a related embodiment, an object, for example, a sample having non-uniform spatial distribution of reflectance and/or transmittance could be used instead of the glass slide 430 to ensure different ratios of spectral peaks' contribution different spatial coordinates of an image detected by the image acquisition apparatus 502 during a single image and/or data acquisition cycle.

For a single beam of spectrum, for example, a beam illuminating light (for example, the incident beam 426, the spectrum of which is shown in FIG. 4B), each of the n spectral peaks is analogous to the spectra of a single fluorescent marker (for example, a quantum dot) for the purposes of testing the spectral unmixing procedure.

Because the n spectral peaks are defined by physical properties of the chosen spectrally selective system 410a, such as a band-pass filter, the spectral positions of these peaks are expected to remain unchanged unless the alignment of the filter 410a is changed. (It is appreciated that the spectral locations of the transmission peaks of different units of the bandpass filter 410a made to the same specification are subject to a measurable tolerance error.)

In one embodiment, the optical acquisition system is appropriately adapted to ensure that a detector of the system is below saturation level (for example, within 80% of the saturation level) when either the source 410 or both the source 410 and the source of light 446 (i.e., spectrum source 448) are switched on. Such illumination limit is enabled, for example, by using stabilized light source(s) calibrated to reliably reproduce (for example, within E %=1% error) illumination levels in terms of known units (e.g., mW) at the sample plane.

Figure 10:
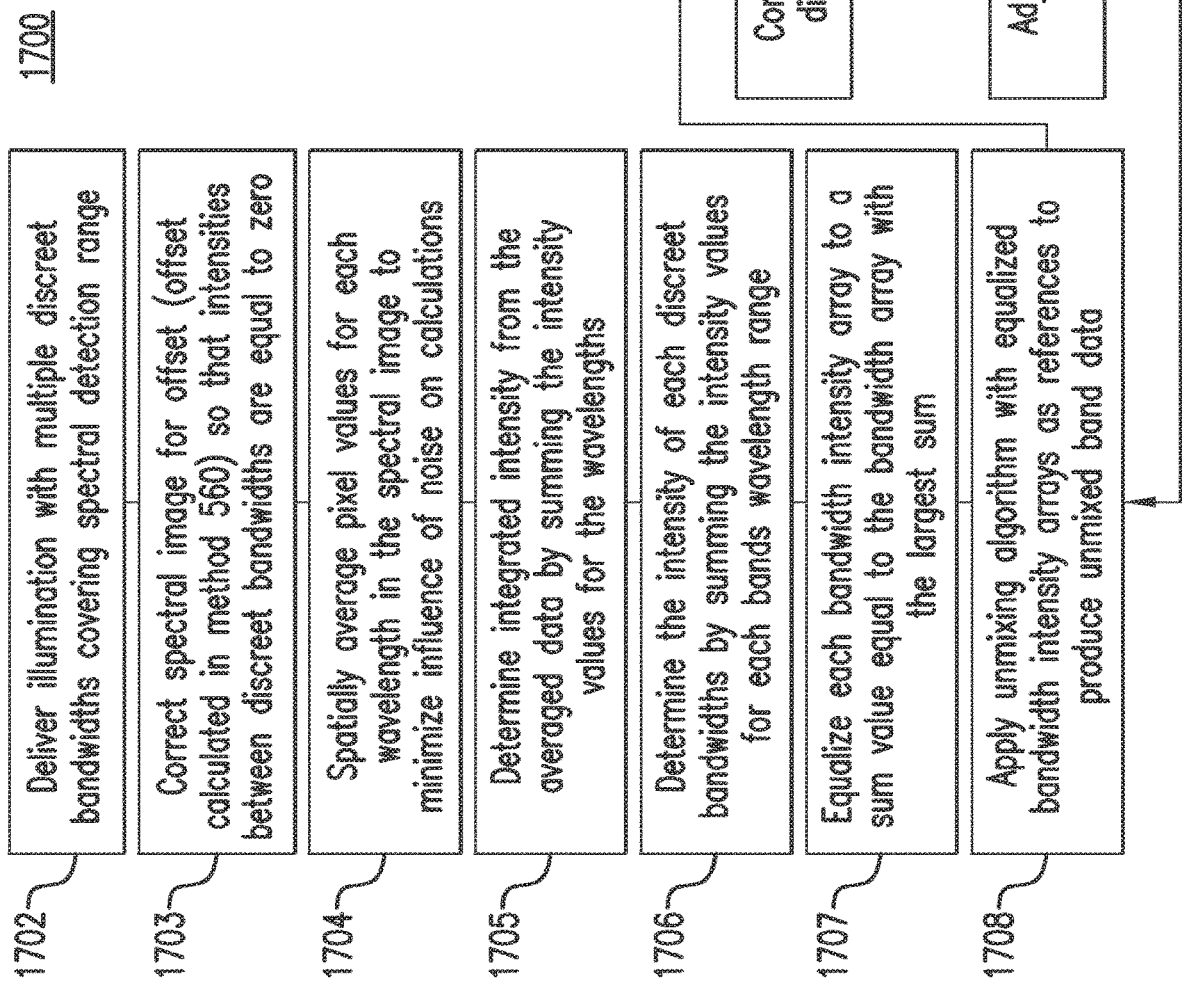
FIG. 10 is a flow-chart representing a method for verification of a process of spectral unmixing of the relative contributions from the multiple spectral peaks of light output from a calibrated source of light.

Referring to FIG. 10, an embodiment 1700 of a method for verification of a process of spectral unmixing of the relative contributions from the multiple spectral peaks of a calibrated light input includes a determination of the overall spectral power, (e.g., optical power) received by the detector or detectors of the image acquisition system 502 and/or image forming apparatus 508s. The overall spectrum power, for example, optical power, is proportional to an area under the spectral curve 422, or to intensity of the source 410 that is spectrally integrated. To determine the integrated intensity, image acquisition system 502 and/or image forming apparatus, for example, a microscope, is first focused on the reflective surface of the slide 430 and a multispectral image of the evenly or substantially even illuminated field of the slide 430 is acquired using a single light path (in this case, the light path in reflection), at step 1010.

The resulting multispectral image is corrected, at step 1020, to take into account the offset of the signal from a baseline intensity value of zero. This offset-correction procedure is carried out in a fashion similar to that described in reference to FIG. 4A and substantially includes a) collecting a multispectral image under the same acquisition conditions but with no light from the spectrum sources 400 and/or 448, for example, optical source(s) delivered to the detector and at a zero exposure time; (b) determining a signal level as an mode intensity; and (c) subtracting the determined signal level that represents a signal offset and/or a pre-determined constant, from the entire multispectral data set corresponding to the earlier acquired multispectral image, on a pixel-by-pixel basis, and at every wavelength used in image acquisition.

Figure 11:
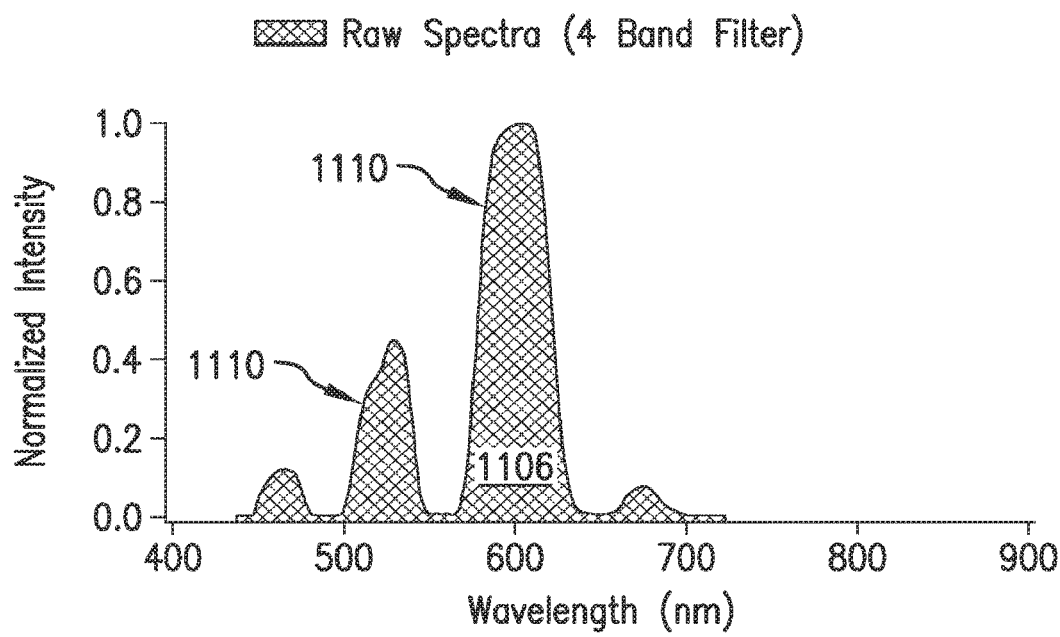
FIGS. 11 and 12 are spectra graphs illustrating the embodiment of the method of FIG. 10.

The mode intensity is derived at every wavelength in a spectral dataset and can be saved as a one-dimensional array (spectral trace) for use in processing all data acquired under given settings. In reference to step 1705 of FIG. 10 and FIG. 11, the integrated intensity corresponding to the area 1106 under the spectral trace envelope 1110 is further determined. The integrated intensity represents the sum wavelength-integrated intensities (of the image) delivered by all spectral bands of the spectrum (e.g., light) beam that has been generated by the source 410 and reflected off of the slide 430 and is utilized to derive a quantity that represents the total amount of light recorded for the multi-band illumination.

Figure 12:
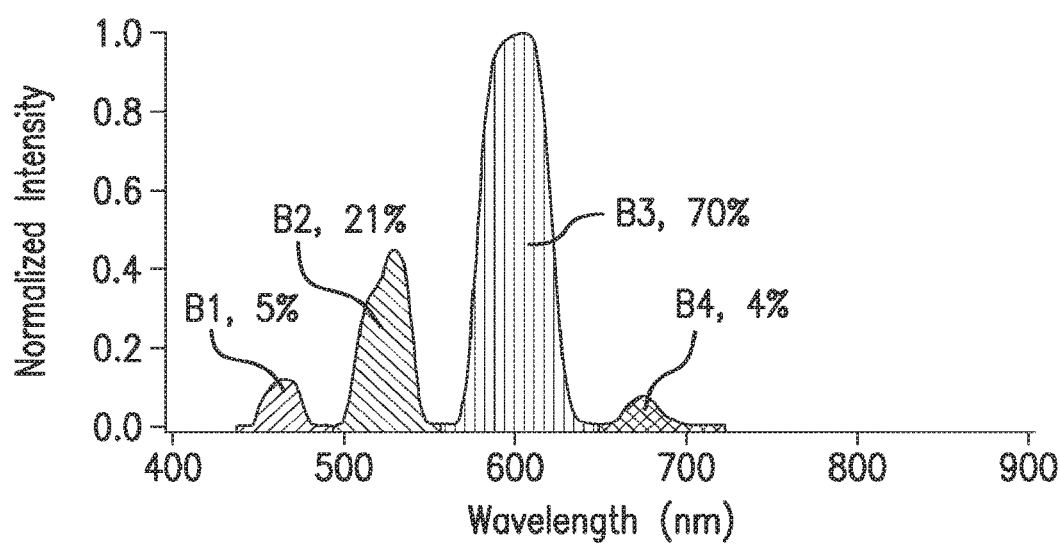

In reference to FIG. 12 and step 1706 of FIG. 10, to determine the relative contribution of each of the spectral bands $B_1$, $B_2$, $B_3$, and $B_4$ to the overall signal, the area under the trace 1110 within each of the bands is calculated and expressed as a percentage of the total area 1106. (Data processing performed at step 1706 is analogous to measuring individual intensity contributions of several distinct fluorophores or quantum dots.) The different relative intensity contributions to the overall signal provide a reproducible (to within E % error, as established by a calibrated light source) and well-characterized standard to test spectral unmixing performance. Accordingly, once the relative contributions of the individual spectral bands of the multiband calibration source and/or spectrum source 410 have been established at step 1706, the information can be used to test an algorithm's ability to reconstruct the measured intensities from subsequent spectral acquisitions using these settings. The optical properties of such standards are known because they are measurable directly, as discussed above.

Figure 13:
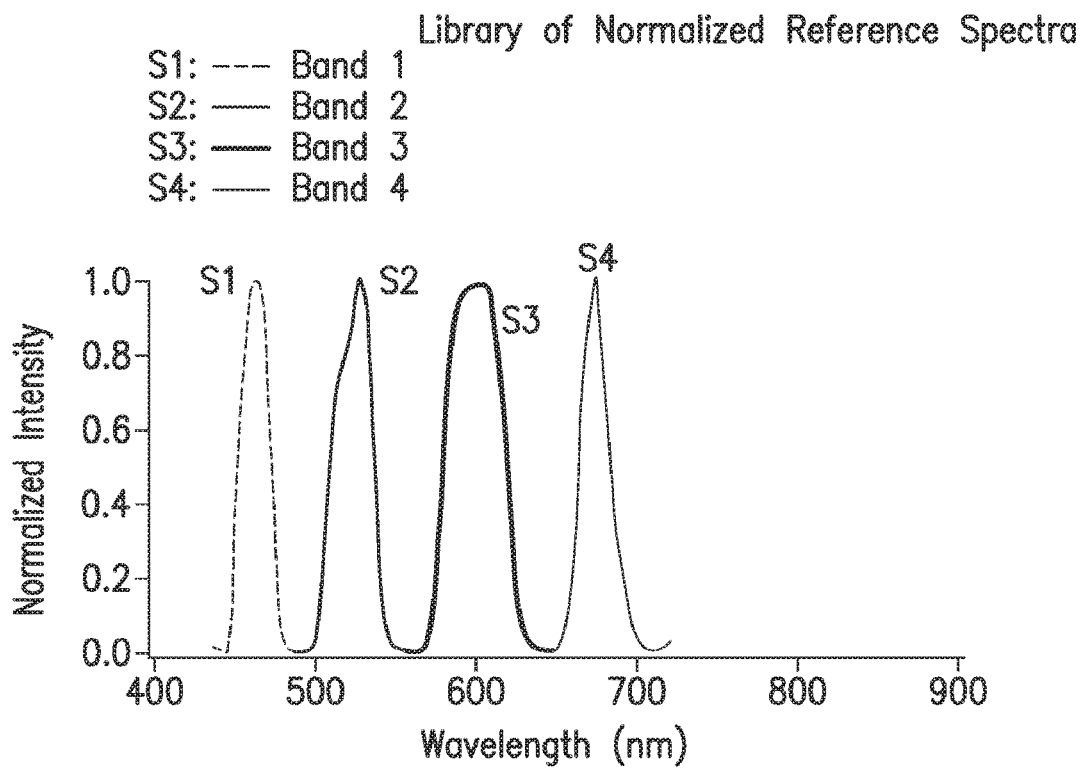
FIG. 13 shows normalized reference spectra for individual spectral bands of the spectrum of FIG. 4B.

In further reference to FIG. 10 and referring now to FIG. 13, data representing the spectral trace 1110 can be optionally processed to form normalized reference spectrum for each of the bands $B_1$, $B_2$, $B_3$, and $B_4$ of the multiband calibration and/or spectrum source 410. To this end, a portion of the data set representing a portion of the spectral trace 1110 that corresponds to a given band is separated or "clipped" at step 1706 from the remaining data (for example, at a point midway between adjacent spectral peaks), and corresponding to the separated band are then normalized at step 1707. Typically in the form of normalization chosen equalizes the integrated area under the curve for each separated band to be the same as the area under the curve for the spectral peak representing the largest contribution to the overall signal. The resulting individual reference spectra $S_1$, $S_2$, $S_3$, and $S_4$ (which in some embodiments is equalized) of the individual bands $B_1$, $B_2$, $B_3$, and $B_4$ can be now used in linear unmixing data processing to separate spectral contributions of different pass bands. The use of these spectra $S_1$, $S_2$, $S_3$, and $S_4$ (e.g., equalized spectra) as reference spectra during the spectral unmixing of spectra, (e.g., light) from a known combination of pass bands facilitates the calculation of the relative contribution of each pass band. This same principle can be employed when tissue labeled with fluorescent analytes is imaged, for example, in quantization of intensity values when ratios of intensity contributions hold important information about underlying protein or gene expression.

Verification of Quantitative Unmixing Algorithm for a Single Light Path.

Figure 14:
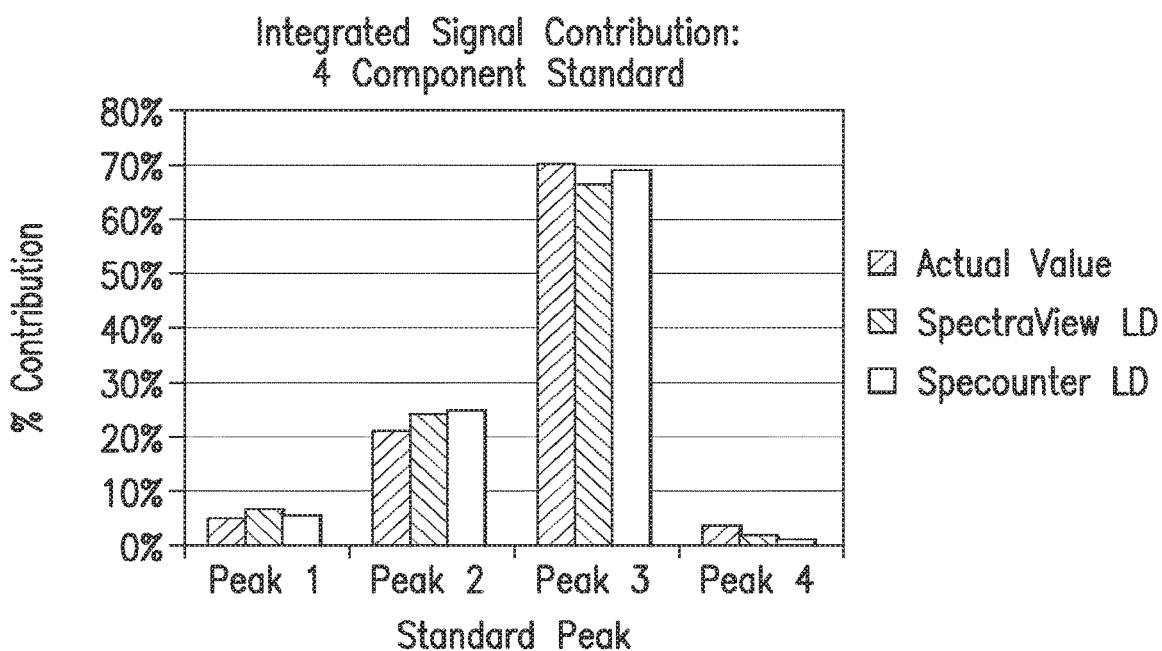
FIG. 14 is a bar-chard showing results of linear unmixing test performed with the use of normalized reference spectra of FIG. 13.

Because, as was discussed above, the relative intensity contributions (shown in FIG. 12) of separate bands $B_1$, $B_2$, $B_3$, and $B_4$ of the calibration light source 410 into the overall spectrum (e.g., light) input received by the image acquisition apparatus 502 have been measured directly, the normalized reference spectra $S_1$, $S_2$, $S_3$, and $S_4$ of FIG. 13 can now be used in linear unmixing to ensure that the linear unmixing algorithm is not erroneous. (In a related embodiment, the proposed methodology is similarly applicable non-linear unmixing.) In particular, if the linear unmixing algorithm is processing data without errors, a relative intensity contribution of a given band determined with the use of the unmixing algorithm would be consistent with the corresponding directly-measured intensity contribution of FIG. 12. Table 1, for example of the application of this method, presents comparison among the results of spectral unmixing performed with two software implemented algorithms, SpectraView and Specounter (both being trademarks of Applied Spectral Imaging, Inc.) which were evaluated for application to multiplex tissue diagnostics using the same standardized imaging instrument hardware, and the directly measured calibrating data of FIG. 12 (referred to as Actual). As shown, the unmixing algorithms ensure substantial accuracy of the calculation to within about 5% of the overall 100% of summed intensities. FIG. 14 provides corresponding illustrations including a bar diagram. In the ideal case, the spectral distribution of spectrum (e.g., light) from a source of spectrum (e.g., light) such as the spectrum and/or calibration source 410 in reflection off of the object/slide 430 should remain unchanged regardless of the power level of the spectrum (e.g., light) output at different spectrum (e.g., light) levels because the spectrum (e.g., light) output from the source 410 is varied by, for example, a chromatically neutral mechanism 416 while keeping the power feed to the source 410 constant. Similarly the spectral distribution of acquired spectrum (e.g., light does not depend on the duration of acquisition time (i.e., exposure time).

TABLE 1

| | SpectraView Unmixed Channels | | | | Specounter Unmixed Channels | | | |
| --- | --- | --- | --- | --- | --- | --- | --- | --- |
| Standard | Average Intensity | Std. Dev. | % Total | Standard | Average Intensity | Std. Dev. | % Total | Actual |
| Peak 1 | 25786 | 1309 | 6.9% | Peak 1 | 4657 | 294 | 5.4% | 5% |
| Peak 2 | 91709 | 3581 | 24.5% | Peak 2 | 21527 | 965 | 24.8% | 21% |
| Peak 3 | 249731 | 10662 | 66.6% | Peak 3 | 59918 | 2687 | 68.9% | 70% |
| Peak 4 | 7519 | 925 | 2.0% | Peak 4 | 820 | 226 | 0.9% | 4% |
| Sum | 374745 | | | Sum | 86922 | | | |

Verification of Quantitative Unmixing Algorithm for Multiple Light Paths.

Figure 15A:
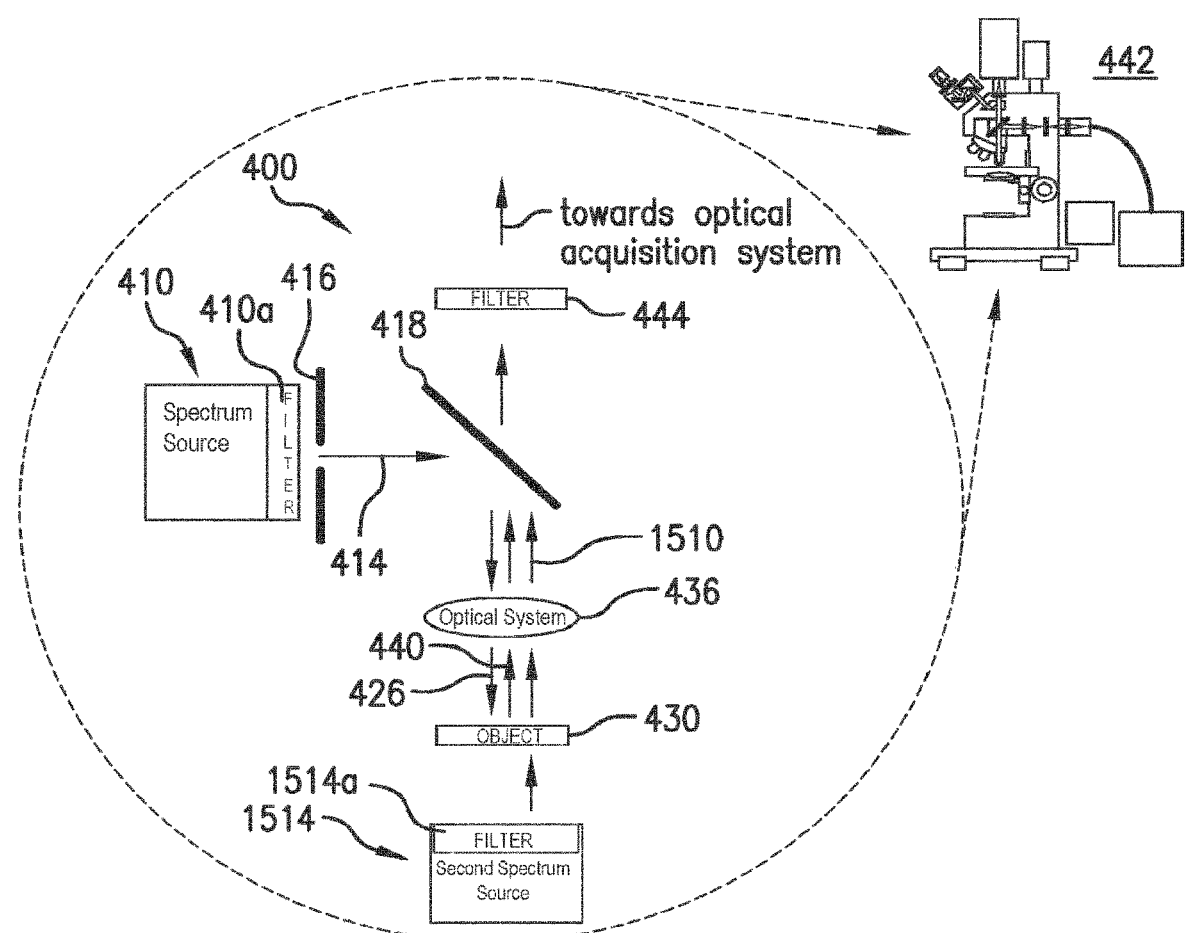
FIG. 15A is a schematic of an embodiment of a two illumination channel MSI system containing first and second calibration sources of light.
Figure 15B:
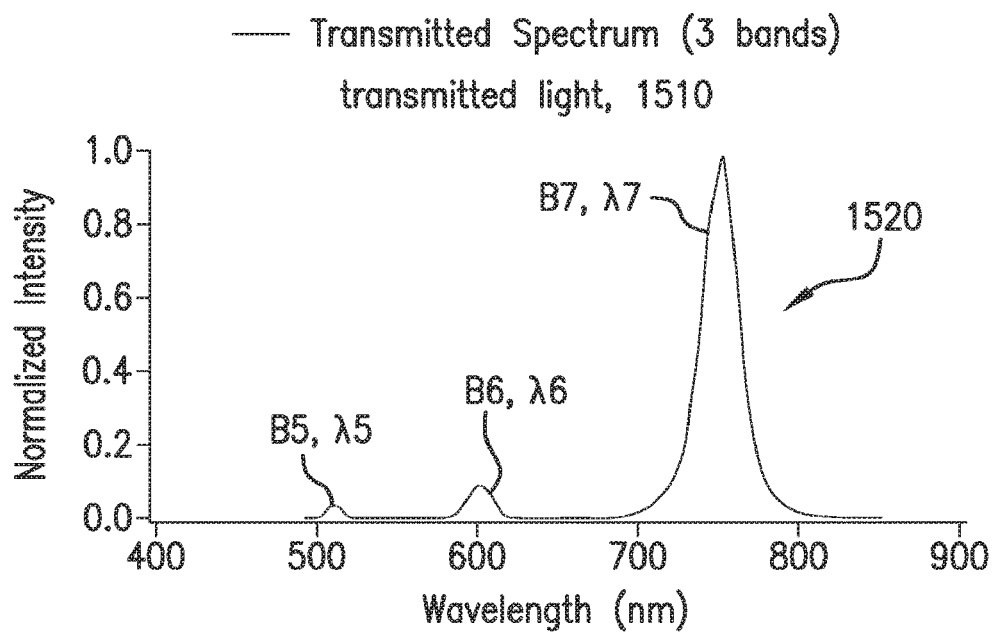
FIGS. 15B and 15C are spectral graphs showing, in comparison, normalized spectra of the first and second source of FIG. 15A.
Figure 15C:
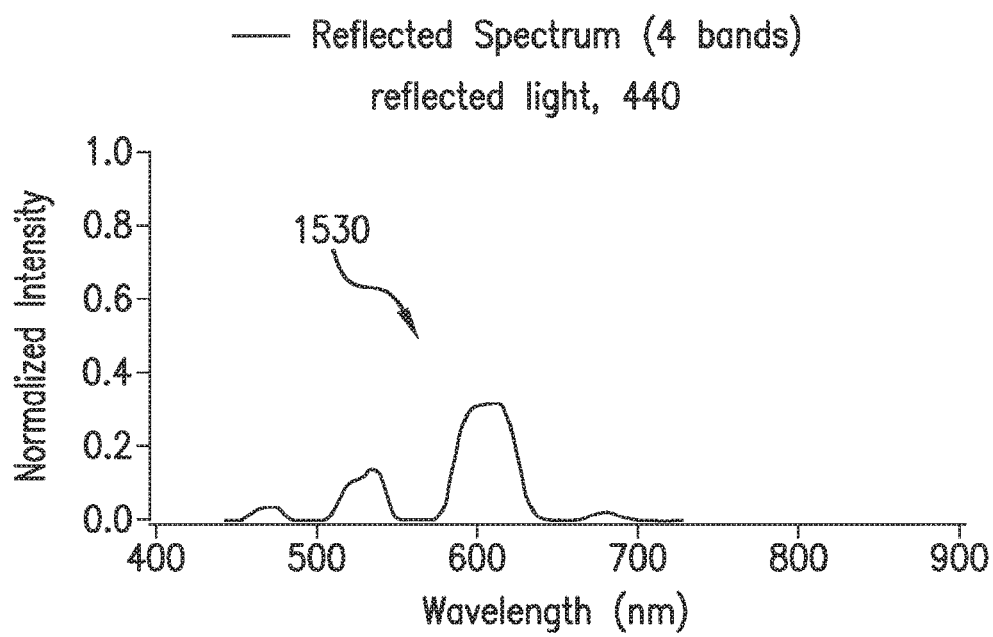

It is understood that verification of accuracy of a spectral-data unmixing algorithm can be similarly carried out when spectrum, e.g., light, is delivered to the image acquisition apparatus 502 along multiple paths. Accordingly, a multi-path verification procedure requires the use of different calibration sources in different paths. Referring to FIG. 15A, 15B, 15C, for example, two light portions that have interacted with the object/slide 430 are received by the optical acquisition system: the beam 440, which is a portion of the beam 426 reflected by the slide 430, and a beam 1510, which is a portion of the beam 446 produced by a second spectrum 1514 and transmitted through slide 430. The second spectrum/calibration source of light 1514 is configured similarly to the source 410 in that it contains a stabilized calibrations spectrum (e.g., light) emitter, a calibration multi-band pass filter 1514a and a diaphragm (not shown) at the output of the source 410 and illuminates the field of view evenly or substantially even. A spectral distribution of spectrum (e.g., light) 446 generally differs from that of spectrum (e.g., light) 414 shown in FIG. 15A. An example of the spectral distribution 1520 of spectrum (e.g., light) 446, shown in FIG. 15B, contains 3 bands: $B_5$, $B_6$, and $B_7$ centered at respectively corresponding wavelengths $\lambda_5$, $\lambda_6$, and $\lambda_7$.

Relative contributions of optical power received in each of the bands $B_5$, $B_6$, and $B_7$ (as compared to the total spectrum (e.g., optical) power of the transmitted beam 446) can be measured directly when only the source 1514 is turned on and the source 410 is turned off. Accordingly, reference spectra for transmitted spectrum (e.g., light) is defined according to a method discussed in relation to FIG. 13.

Figure 16A:
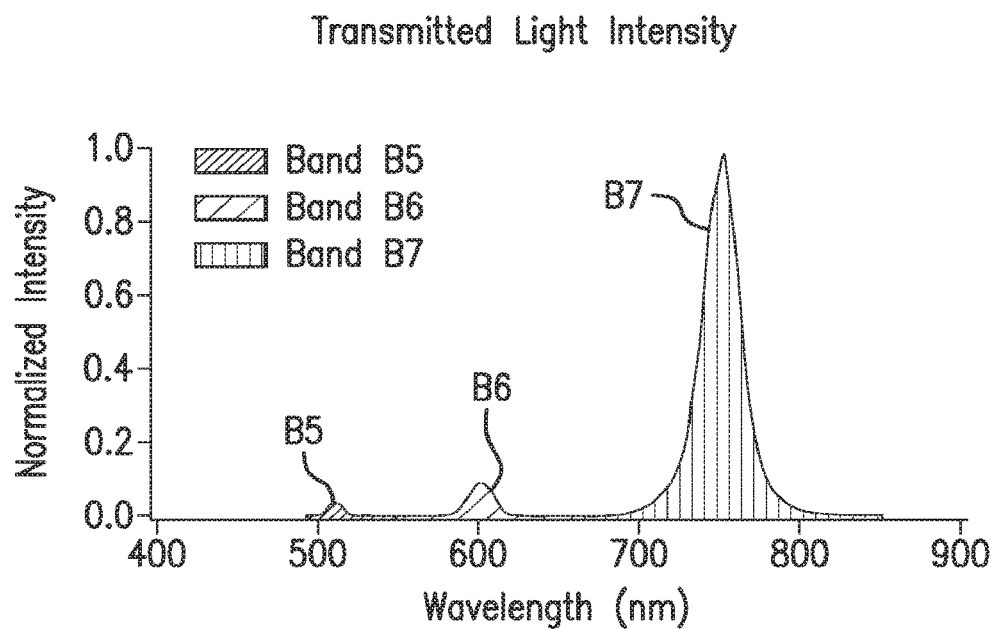
FIGS. 16A and 16B are spectral graphs illustrating a method for verification of a process of spectral unmixing of the relative contributions from the multiple spectral peaks of light output from multiple calibrated sources of light according to an embodiment of the invention.
Figure 16B:
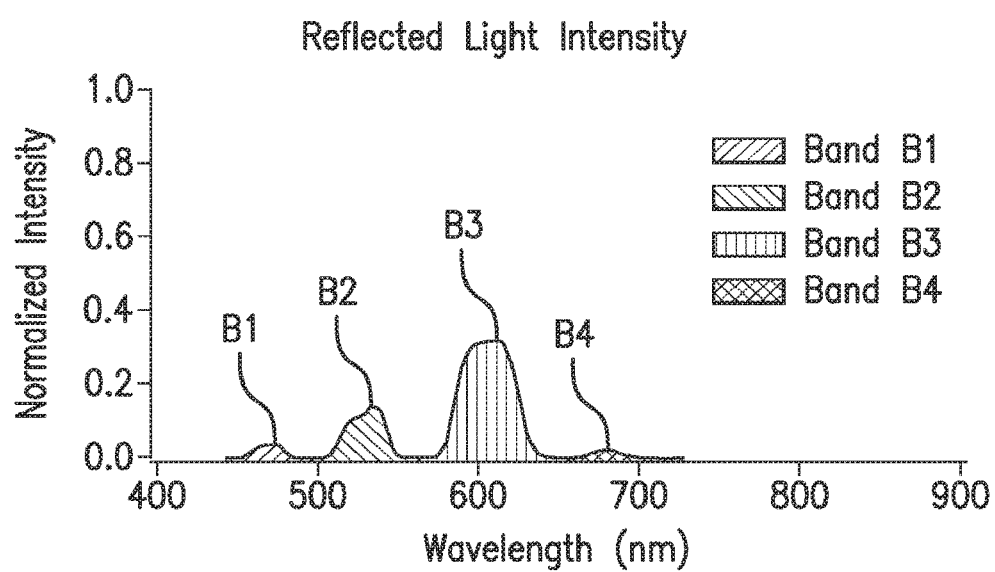
Figure 17:
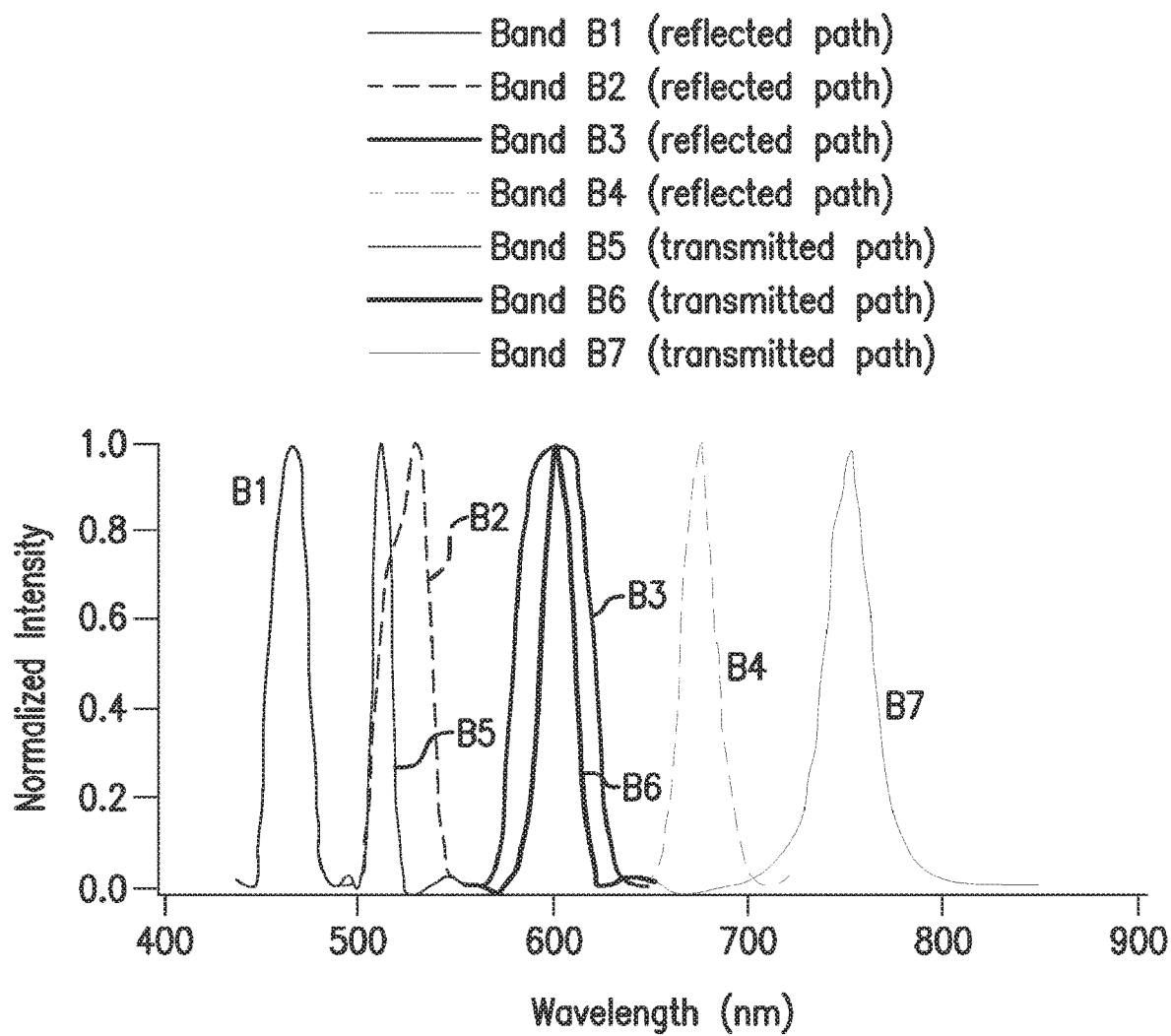
FIG. 17 shows normalized reference spectra for individual spectral bands of the spectra of first and second sources of light of FIG. 15B, 15C.

It is also appreciated that the reflected beam 440 (having spectral bands $B_1$, $B_2$, $B_3$, and $B_4$) and the transmitted beam 1510 (having spectral bands $B_5$, $B_6$, and $B_7$) substantially do not interfere and do overlap linearly at the detector or detectors (e.g., sensors) of the image acquisition system 502. Consequently, when both spectrum (e.g., light) sources 410, 1514 are turned on, spectrum power (e.g., optical power)

delivered to the image acquisition system 502, in each of the abovementioned bands, can be measured directly and independently of that in another band in either reflected or transmitted spectrum (e.g. optical) paths, thereby permitting direct measurement of the contribution of spectrum (e.g., optical) power in each of the spectral bands registered at the detector relative to the total received spectrum (e.g., optical) power. FIGS. 15B and 15C illustrate, for comparison, spectra 1520 and 1530 of spectra (e.g., light) beams 414 and 440, respectively, and, for example, to the area under the strongest peak $B_7, \lambda_7$. Here, the halogen lamp was used as the light source 1514 and the filter 1514a included an optical filter transmitting in near IR. In reference to FIGS. 16A, 16B, spectral characteristics of spectrum, e.g., light, received by the detector from either of the individual optical paths (i.e., in reflection and transmission) are further directly measured as discussed above and used to construct reference spectral calibration standards (similar to those of FIG. 13) for calibration/verification of spectral unmixing system and algorithms Normalized spectra of calibration standards so devised for both reflection and transmission paths (e.g., optical paths) are plotted together in FIG. 17, showing substantial overlap of spectra of the transmission and reflection paths' calibration sources 1514, 410 in the visible portion of the spectrum.

Figure 18:
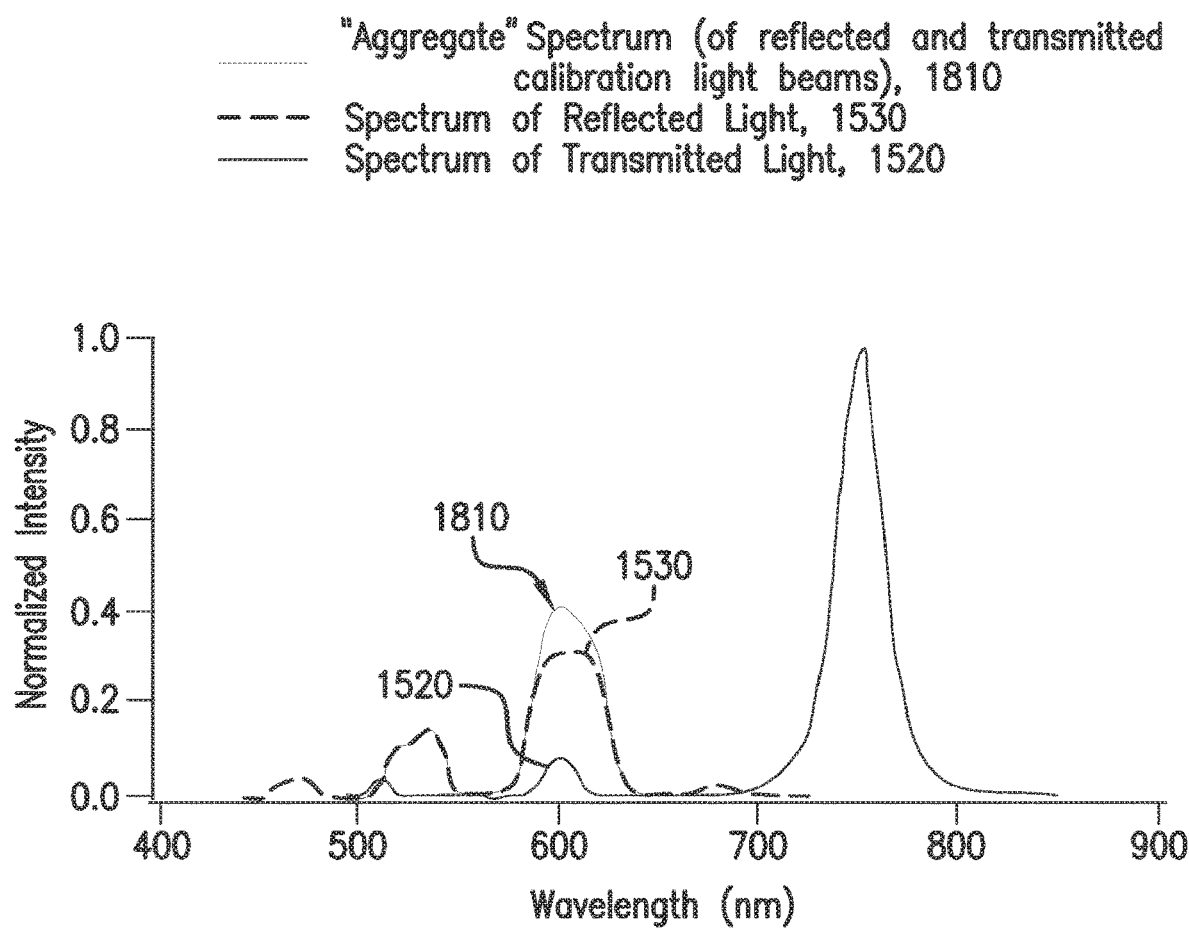
FIG. 18 is a plot representing the spectral trace registered by the detector of the optical acquisition system of the invention employing two calibration/reference light standards.
Figure 19:
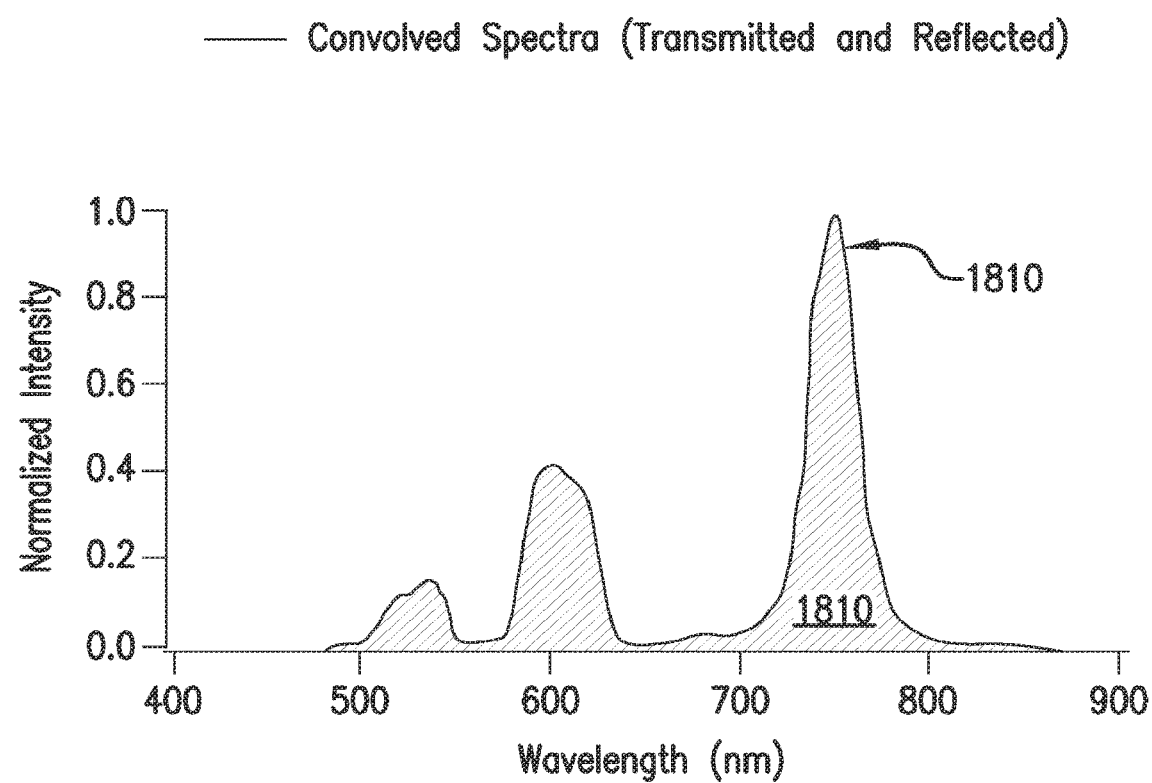
FIG. 19 illustrates the use of area under the aggregate spectral trace of FIG. 18.

The "aggregate" normalized spectral trace 1810 of FIG. 18 represents the spectral trace registered by the detector of the image acquisition system when both individual calibration/reference light standards 410 and 1514 are switched on. The area 1916 under the spectral trace envelope 1810 may be further determined, as shown in FIG. 19, and compared with the sum of the areas under the individual spectral traces of FIGS. 16A and 16B to determine agreement between the individual components' spectral traces and the total. Because the optical acquisition system was earlier referenced to the normalized calibration spectra 1520, 1530, the integrated intensity 1916 remains substantially equal to the sum of intensities of the individual spectrum (e.g., light) standards 410, 414 as long as the overall optical train (including the filters, lenses, and optical acquisition system itself) does not experience any changes such as re-alignment or replacement, for example A substantial deviation from such balance is indicative that the optical train of the MSI system has been changed since the moment of calibration using individually operating sources 410,414.

Figure 20A:
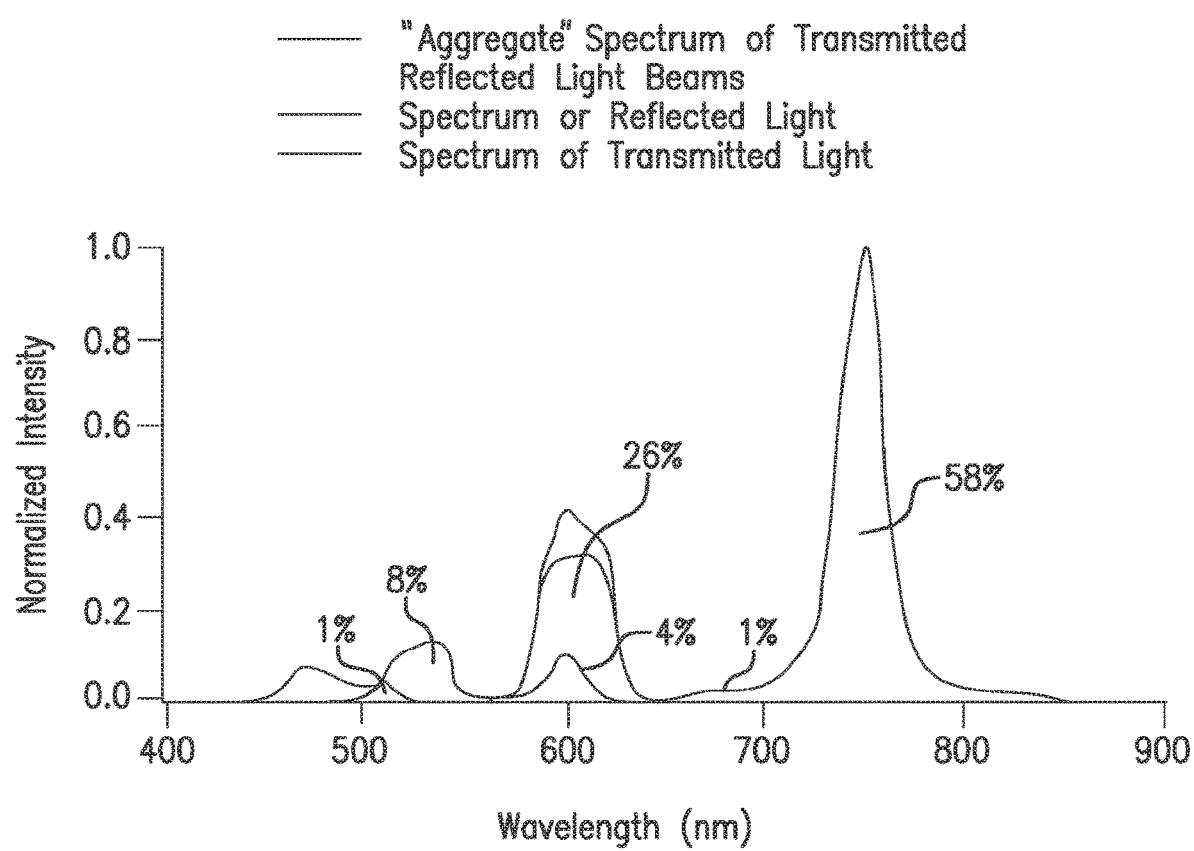
Figure 20B:
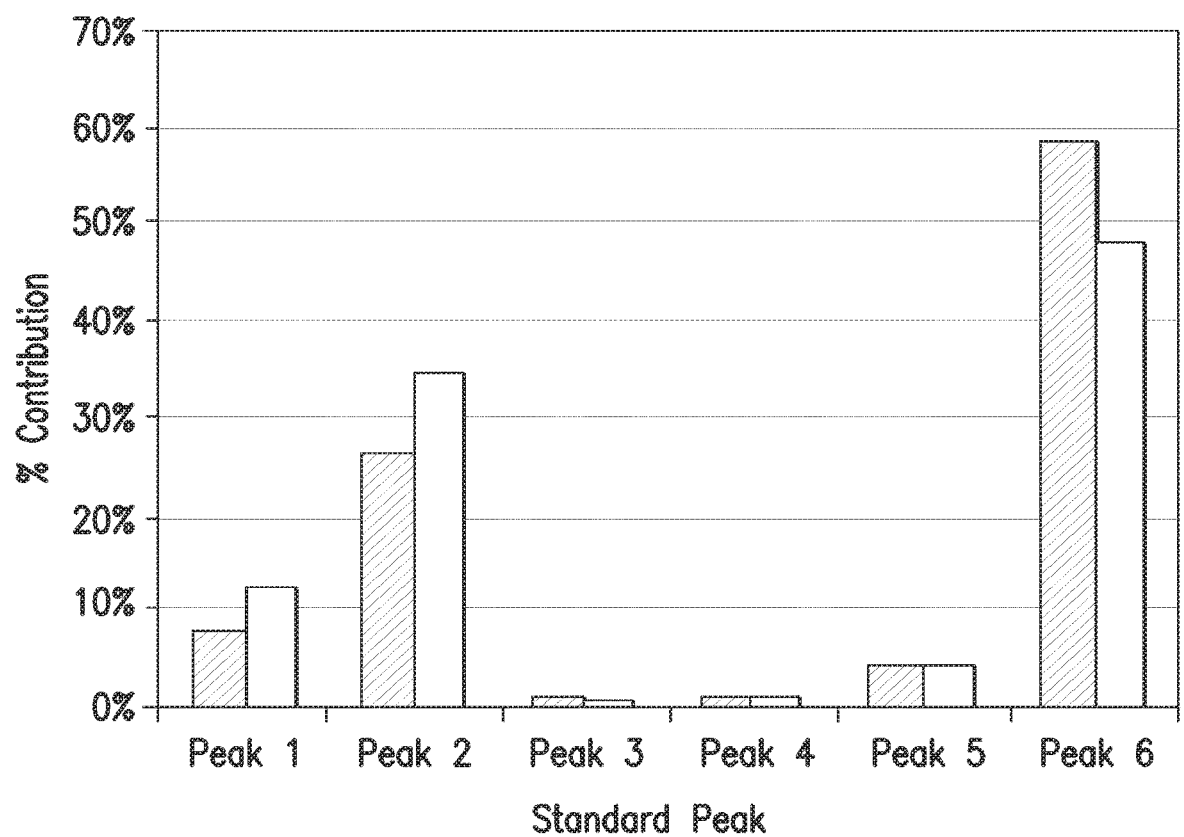

FIG. 20 provides an illustration to a system-level test of a measurement system that is assumed to have been pre-calibrated. In reference to the light received at the detector component of the measurement system represents a mix of six at least partially overlapping spectral bands each of which represents a spectral standard. (Bands of a spectral standard are emulated by using two spectral filters, each in one arm of the measurement system of the invention, with known spectral characteristics.) Therefore, it is known a priori the amount of spectrum (e.g., light) signal present in the mix at each of the spectral bands and/or wavelengths. As can be seen from the inset A of FIG. 20, different spectral bands/channels overlap in different ratios, and the assumption is made that no non-linear effects affect the spectral mixing of spectra, e.g., light, incident onto the detector. An embodiment of a spectral unmixing algorithm is used to determine, via calculation, values representing the amount of spectrum, e.g., light, in each spectral bands (see insets B and C). The comparison between the known actual and calculated values indicates whether the used spectral unmixing algorithm requires a correction and to what degree.

Figures 3, 21B:
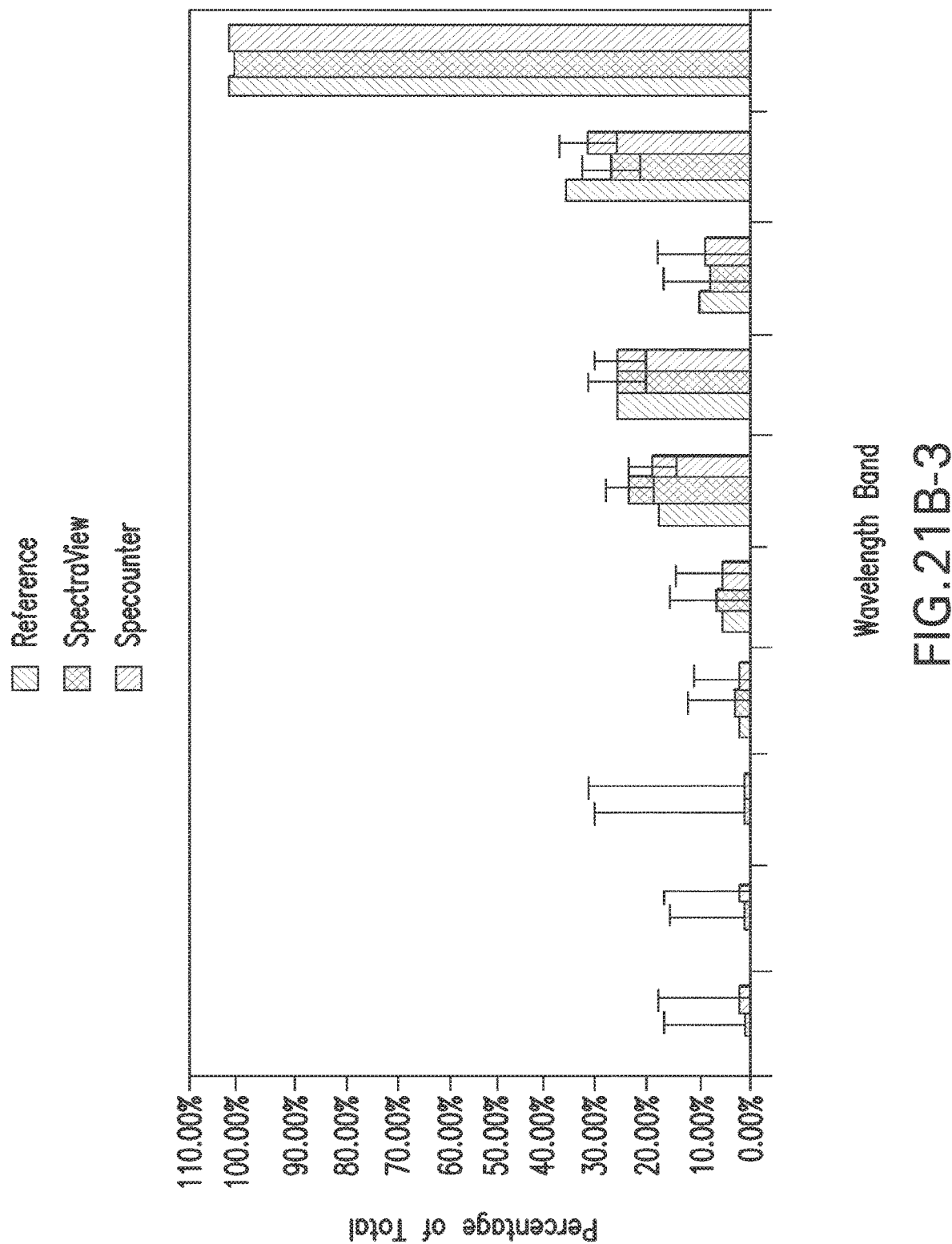

FIGS. 21A and 21B provide plots and related data illustrating a spectral unmixing, according to the method described above, of 9 spectral features with accuracy to within 5%, as measured with respect to the known contribution for individual spectral peaks of a known standard.

Figure 22:
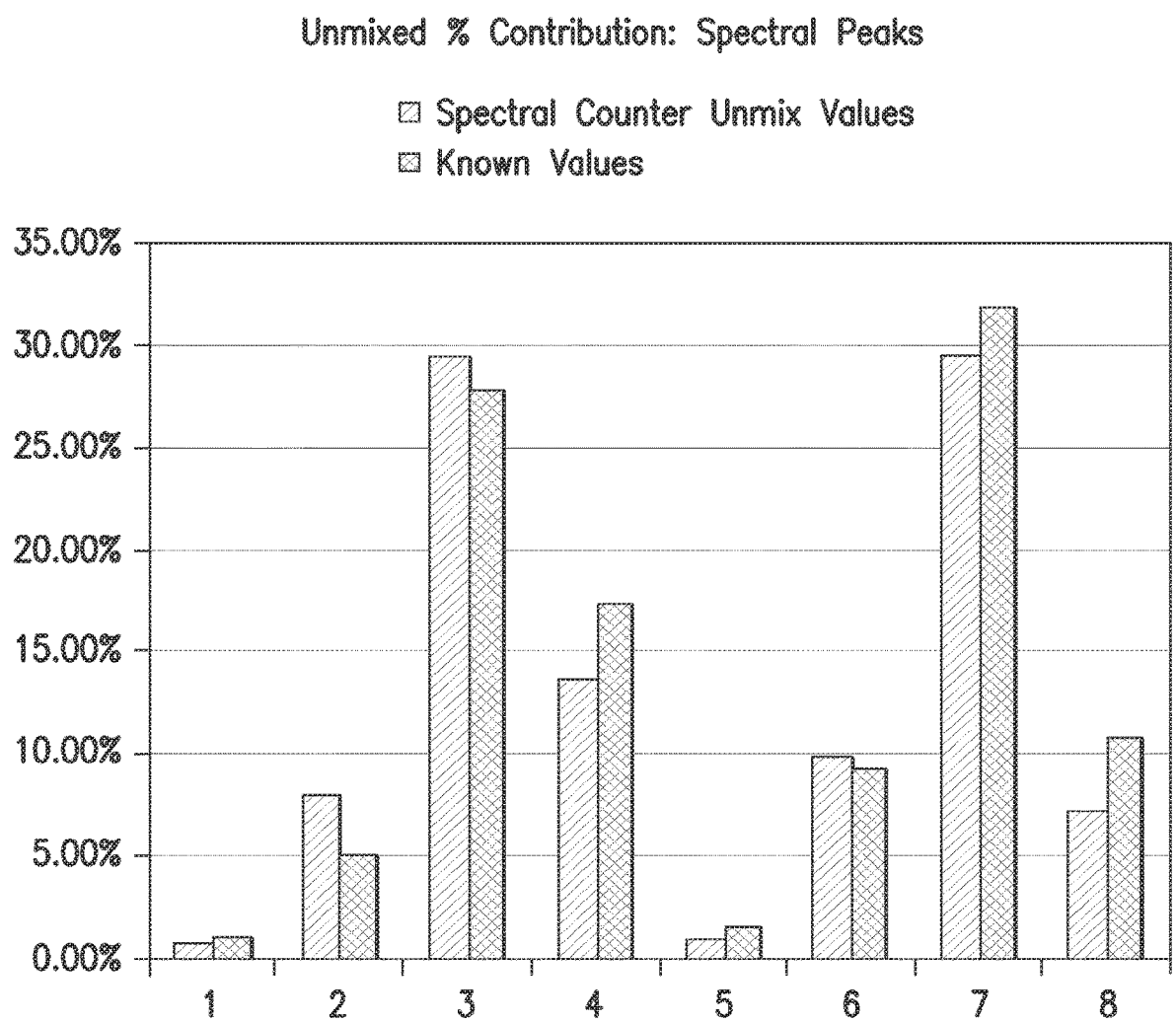
FIG. 22 illustrates the results of operation of a related embodiment of the invention.

FIG. 22 and the related data in Table 2 illustrate efficiency of operation of an embodiment of the invention used for spectral unmixing employing 4-band standard filters (e.g., optical filters) in incident and transmitted beams. Table 2 presents values corresponding to relative intensity contributions for the 8 spectral peaks as percentage of the total intensity of light received by the system in the process of forming a hyperspectral cube of data. As the "Difference" column indicates, the results of linear unmixing obtained with an embodiment of the algorithm of the invention are in good agreement with values measured directly.

TABLE 2

| | ASI Spectral Counter Unmix Layers | | | | | Area Under Curve | |
|---|---|---|---|---|---|---|---|
| | Area | Mean | StdDev | Mode | % total | Measured % | Difference |
| RPeak1 | 898560 | 1643.258 | 119.778 | 1633.832 | 0.83% | 1.10% | 0.27% |
| RPeak2 | 898560 | 15632.04 | 885.115 | 16067.12 | 8.16% | 5.10% | −3.06% |
| RPeak3 | 898560 | 55912.92 | 3144.496 | 58180.38 | 29.56% | 27.80% | −1.76% |
| RPeak4 | 898560 | 26112.59 | 1794.595 | 27189.74 | 13.81% | 17.40% | 3.59% |
| TPeak1 | 898560 | 1985.762 | 199.211 | 1949.101 | 0.99% | 1.60% | 0.61% |
| TPeak2 | 898560 | 20366.96 | 1166.834 | 19537.53 | 9.93% | 9.30% | −0.63% |
| TPeak3 | 898560 | 60849.47 | 2895.438 | 58198.08 | 29.57% | 31.90% | 2.33% |
| TPeak4 | 898560 | 14689.91 | 720.86 | 14087.45 | 7.16% | 10.70% | 3.54% |
| | | | | Total | 196843.2 | 100.00% | |

Figure 23:
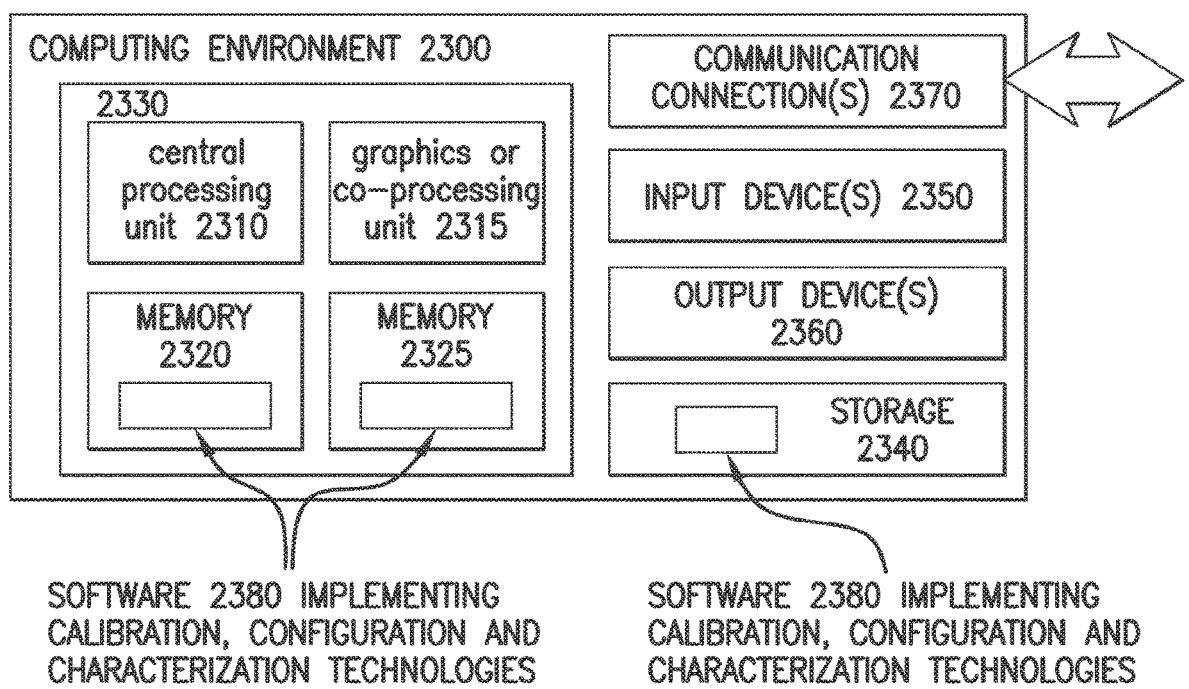
FIG. 23 is a block diagram of an exemplary computing system in which described embodiments can be implemented.

FIG. 23 illustrates a generalized example of a suitable computing system in which several of the described innovations may be implemented. The computing system is not intended to suggest any limitation as to scope of use or functionality, as the innovations may be implemented in diverse general-purpose or special-purpose computing systems.

With reference to FIG. 23, the computing system includes one or more processing units and memory 2320, 2325. The processing units 2315 executes computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 23 shows a central processing unit 2310 as well as a graphics processing unit or co-processing unit 2315. The tangible memory 2320,2325 may be volatile memory (e.g., registers, cache, RAM), non-volatile memory (e.g., ROM, EEPROM, flash memory, etc.), or some combination of the two, accessible by the processing unit(s). The memory 2320,2325 stores software 2380 implementing one or more innovations described herein, in the form of computer-executable instructions suitable for execution by the processing unit(s).

A computing system may have additional features. For example, the computing system includes storage 2340, one or more input devices 2350, one or more output devices 2360, and one or more communication connections 2370. An interconnection mechanism (not shown) such as a bus, controller, or network interconnects the components of the computing system. Typically, operating system software (not shown) provides an operating environment for other software executing in the computing system, and coordinates activities of the components of the computing system.

The tangible storage 2340 may be removable or non-removable, and includes magnetic disks, magnetic tapes or cassettes, CD-ROMs, DVDs, or any other medium which can be used to store information in a non-transitory way and which can be accessed within the computing system. The storage 2340 stores instructions for the software 2380 implementing one or more innovations described herein.

The input device(s) 2350 may be a touch input device such as a keyboard, mouse, pen, or trackball, a voice input device, a scanning device, or another device that provides input to the computing system. For video encoding, the input device(s) 50 may be a camera, video card, TV tuner card, or similar device that accepts video input in analog or digital form, or a CD-ROM or CD-RW that reads video samples into the computing system. The output device(s) 2360 may be a display, printer, speaker, CD-writer, or another device that provides output from the computing system.

The communication connection(s) 2370 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-readable media. Computer-readable media are any available tangible media that can be accessed within a computing environment. By way of example, and not limitation, with the computing system, computer-readable media include memory 2230, 2325, storage 2340, and combinations of any of the above.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

The terms "system" and "device" are used interchangeably herein. Unless the context clearly indicates otherwise, neither term implies any limitation on a type of computing system or computing device. In general, a computing system or computing device can be local or distributed, and can include any combination of special-purpose hardware and/or general-purpose hardware with software implementing the functionality described herein.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Any of the computer-readable media herein can be non-transitory (e.g., memory, magnetic storage, optical storage, or the like).

Any of the storing actions described herein can be implemented by storing in one or more computer-readable media (e.g., computer-readable storage media or other tangible media).

Any of the things described as stored can be stored in one or more computer-readable media (e.g., computer-readable storage media or other tangible media).

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages.

Any of the methods described herein can be implemented by computer-executable instructions stored in one or more computer-readable storage devices (e.g., memory, magnetic storage, optical storage, or the like). Such instructions can cause a computer to perform the method.

While the invention is described through the above-described examples of embodiments, it will be understood by those of ordinary skill in the art that modifications to, and variations of, the illustrated embodiments may be made without departing from the inventive concepts disclosed herein. For example, although some aspects of embodiments have been described with reference to a flowchart, those skilled in the art should readily appreciate that functions, operations, decisions, etc. of all or a portion of each block, or a combination of blocks, of the flowchart may be combined, separated into separate operations or performed in other orders. Moreover, while the embodiments are described in connection with various illustrative data structures, one skilled in the art will recognize that the system may be embodied using a variety of data structures. Furthermore, disclosed aspects, or portions of these aspects, may be combined in ways not listed above. A computer program product effectuating a programmable processor of a system to perform the steps of embodiments of the algorithm described in this application is also within the scope of the invention. Accordingly, the invention should not be viewed as being limited to the disclosed embodiment(s).

The invention claimed is:
1. A method comprising:
acquiring, with a detector, a multispectral (MS) image of a reference sample that is evenly illuminated with light from a light source having spectral output with multiple spectral bands, the light source further including an optical filter having a transmission spectrum that corresponds to a spectrum of a calibrated light standard;

determining an intensity offset by comparing a distribution of intensities corresponding to a baseline image with another distribution of intensities corresponding to the acquired image;

correcting, based on the intensity offset, the acquired image to form a bias-corrected MS image;

generating an average of intensity profile characteristics corresponding to a subset of pixels in the bias-corrected MS image;

determining an integrated intensity value based on an averaged intensity profile; and outputting the integrated intensity value.

2. The method of claim 1, wherein the determining an integrated intensity value includes averaging a spectral profile of intensity of the bias-corrected MS image over chosen pixels of the detector to form a averaged intensity profile.

3. The method of claim 1, wherein the acquiring includes:
receiving, with said detector, first light that has transmitted through said reference sample and second light that has reflected off of said reference sample, each of said first and second light having a corresponding multiband spectrum; and determining a first contribution of light in a first spectral band of said first light relative to light received with the detector, the first contribution independently determined from a second contribution of light in second spectral band of said second light.

4. The method of claim 1, further comprising varying relative contributions of light from different spectral bands to the acquired image without substantially changing spectral content of light received with said detector.

5. The method of claim 1, wherein the light source is calibrated to form a calibrated light source, wherein the method further comprises:
defining relative contributions of light from different spectral bands of an output of the calibrated light source; and individually normalizing averaged intensity profile characteristics corresponding to each of the different spectral bands to define normalized individual-reference spectra corresponding to the multiple spectral bands.

6. The method of claim 5, further comprising determining differences between results of a computational spectral unmixing algorithm and the defined relative contributions of light.

7. The method of claim 1, wherein the integrated intensity value is used to determine accuracy of a computational algorithm for spectral unmixing of the acquired image.

8. A system comprising:
one or more data processors; and
a non-transitory computer readable storage medium containing instructions which, when executed on the one or more data processors, cause the one or more data processors to perform operations including:
acquiring, with a detector, a multispectral (MS) image of a reference sample that is evenly illuminated with light from a light source having spectral output with multiple spectral bands, the light source further including an optical filter having a transmission spectrum that corresponds to a spectrum of a calibrated light standard;

determining an intensity offset by comparing a distribution of intensities corresponding to a baseline image with another distribution of intensities corresponding to the acquired image;

correcting, based on the intensity offset, the acquired image to form a bias-corrected MS image;

generating an average of intensity profile characteristics corresponding to a subset of pixels in the bias-corrected MS image;

determining an integrated intensity value based on an averaged intensity profile; and outputting the integrated intensity value.

9. The system of claim 8, wherein the determining an integrated intensity value includes averaging a spectral profile of intensity of the bias-corrected MS image over chosen pixels of the detector to form a averaged intensity profile.

10. The system of claim 8, wherein the acquiring includes:
receiving, with said detector, first light that has transmitted through said reference sample and second light that has reflected off of said reference sample, each of said first and second light having a corresponding multiband spectrum; and determining a first contribution of light in a first spectral band of said first light relative to light received with the detector, the first contribution independently determined from a second contribution of light in second spectral band of said second light.

11. The system of claim 8, wherein the operations further include varying relative contributions of light from different spectral bands to the acquired image without substantially changing spectral content of light received with said detector.

12. The system of claim 8, wherein the light source is calibrated to form a calibrated light source, wherein the operations further include:
defining relative contributions of light from different spectral bands of an output of the calibrated light source; and individually normalizing averaged intensity profile characteristics corresponding to each of the different spectral bands to define normalized individual-reference spectra corresponding to the multiple spectral bands.

13. The system of claim 12, further comprising determining differences between results of a computational spectral unmixing algorithm and the defined relative contributions of light.

14. A non-transitory computer-readable storage medium storing instructions executable by a processor to perform operations comprising:
acquiring, with a detector, a multispectral (MS) image of a reference sample that is evenly illuminated with light from a light source having spectral output with multiple spectral bands, the light source further including an optical filter having a transmission spectrum that corresponds to a spectrum of a calibrated light standard;

determining an intensity offset by comparing a distribution of intensities corresponding to a baseline image with another distribution of intensities corresponding to the acquired image;

correcting, based on the intensity offset, the acquired image to form a bias-corrected MS image;

generating an average of intensity profile characteristics corresponding to a subset of pixels in the bias-corrected MS image;

determining an integrated intensity value based on an averaged intensity profile; and outputting the integrated intensity value.

15. The non-transitory computer-readable storage medium of claim 14, wherein the determining an integrated intensity value includes averaging a spectral profile of intensity of the bias-corrected MS image over chosen pixels of the detector to form a averaged intensity profile.

16. The non-transitory computer-readable storage medium of claim 14, wherein the acquiring includes:
   receiving, with said detector, first light that has transmitted through said reference sample and second light that has reflected off of said reference sample, each of said first and second light having a corresponding multiband spectrum; and
   determining a first contribution of light in a first spectral band of said first light relative to light received with the detector, the first contribution independently determined from a second contribution of light in second spectral band of said second light.

17. The non-transitory computer-readable storage medium of claim 14, wherein the operations further include varying relative contributions of light from different spectral bands to the acquired image without substantially changing spectral content of light received with said detector.

18. The non-transitory computer-readable storage medium of claim 14, wherein the light source is calibrated to form a calibrated light source, wherein the operations further include:
   defining relative contributions of light from different spectral bands of an output of the calibrated light source; and
   individually normalizing averaged intensity profile characteristics corresponding to each of the different spectral bands to define normalized individual-reference spectra corresponding to the multiple spectral bands.

19. The non-transitory computer-readable storage medium of claim 18, further comprising determining differences between results of a computational spectral unmixing algorithm and the defined relative contributions of light.

20. The non-transitory computer-readable storage medium of claim 14, wherein the integrated intensity value is used to determine accuracy of a computational algorithm for spectral unmixing of the acquired image.

* * * * *